(12) United States Patent
Mandro et al.

(10) Patent No.: US 9,656,031 B2
(45) Date of Patent: *May 23, 2017

(54) INFUSION PUMP METHODS AND SYSTEMS

(75) Inventors: Marc A. Mandro, Bow, NH (US); Geoffrey P. Spencer, Manchester, NH (US); Robert J. Bryant, Jr., Manchester, NH (US); Patricia M. Armstrong, New Boston, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/731,843

(22) Filed: Mar. 25, 2010

(65) Prior Publication Data

US 2011/0047499 A1    Feb. 24, 2011

Related U.S. Application Data

(63) Continuation-in-part of application No. 12/416,662, filed on Apr. 1, 2009.

(Continued)

(51) Int. Cl.
*A61M 5/00* (2006.01)
*A61M 1/00* (2006.01)
(Continued)

(52) U.S. Cl.
CPC .......... *A61M 5/5086* (2013.01); *A61M 5/142* (2013.01); *A61M 5/14244* (2013.01);
(Continued)

(58) Field of Classification Search
CPC ......... A61M 2005/14268; A61M 2005/14296; A61M 2205/0266; A61M 2205/3368; A61M 2205/35; A61M 2205/3569; A61M 2205/3592; A61M 2205/502; A61M 2205/60; A61M 2230/201; A61M 5/142; A61M 5/14244; A61M 5/172; A61M 5/1723; A61M 5/14566; A61M 5/16827;
(Continued)

(56) References Cited

U.S. PATENT DOCUMENTS

2002/0072733 A1    6/2002  Flaherty
2003/0060765 A1    3/2003  Campbell et al.
(Continued)

FOREIGN PATENT DOCUMENTS

EP    177802 A    2/2002
EP    1839694 A    10/2007
(Continued)

OTHER PUBLICATIONS

International Search Report with Written Opinion, dated Mar. 31, 2010, received in international patent application No. PCT/US2009/093169, 23 pages.
(Continued)

*Primary Examiner* — Jason Flick
(74) *Attorney, Agent, or Firm* — Michelle Saquet Temple

(57) ABSTRACT

An infusion pump system is disclosed. The system includes at least one infusion pump, a companion device, the companion device in wireless communication with the infusion pump, and a user interface on the companion device, the user interface adapted to receive textual input.

19 Claims, 60 Drawing Sheets

Related U.S. Application Data

(60) Provisional application No. 61/163,273, filed on Mar. 25, 2009, provisional application No. 61/165,592, filed on Apr. 1, 2009, provisional application No. 61/041,291, filed on Apr. 1, 2008.

(51) Int. Cl.

| | | |
|---|---|---|
| *A61M 5/50* | (2006.01) | |
| *A61M 5/142* | (2006.01) | |
| *A61M 5/172* | (2006.01) | |
| *G05D 7/06* | (2006.01) | |
| *G06F 19/00* | (2011.01) | |
| *G08B 21/18* | (2006.01) | |

(52) U.S. Cl.
CPC .......... *A61M 5/172* (2013.01); *A61M 5/1723* (2013.01); *G05D 7/0676* (2013.01); *G06F 19/3468* (2013.01); *G08B 21/182* (2013.01); *A61M 2005/14268* (2013.01); *A61M 2005/14296* (2013.01); *A61M 2205/0266* (2013.01); *A61M 2205/18* (2013.01); *A61M 2205/3368* (2013.01); *A61M 2205/35* (2013.01); *A61M 2205/3569* (2013.01); *A61M 2205/3592* (2013.01); *A61M 2205/502* (2013.01); *A61M 2205/60* (2013.01); *A61M 2230/201* (2013.01); *G08C 2201/20* (2013.01)

(58) Field of Classification Search
CPC ............ A61M 25/007; A61M 25/0068; A61M 25/0662; G05D 7/0676; G06F 19/3468; G06F 3/04886; G06F 3/04817; G06F 3/0482; G06F 3/0488; G06F 3/041; G06F 3/04883; G08C 2201/20
USPC ........................................................ 604/264
See application file for complete search history.

(56) References Cited

U.S. PATENT DOCUMENTS

| | | |
|---|---|---|
| 2003/0163088 A1 | 8/2003 | Blomquist |
| 2004/0077997 A1 | 4/2004 | Jasperson et al. |
| 2005/0022274 A1* | 1/2005 | Campbell .......... A61B 5/14532 604/131 |
| 2005/0065464 A1 | 3/2005 | Talbot et al. |
| 2007/0016170 A1 | 1/2007 | Kovelman |
| 2007/0112298 A1 | 5/2007 | Mueller et al. |
| 2007/0179549 A1* | 8/2007 | Russie ............................ 607/29 |
| 2007/0233051 A1* | 10/2007 | Hohl .................... A61B 5/1486 604/891.1 |
| 2007/0265533 A1 | 11/2007 | Tran |
| 2008/0125064 A1 | 5/2008 | Das et al. |
| 2009/0221890 A1* | 9/2009 | Saffer ................ A61B 5/14532 600/347 |
| 2009/0228825 A1* | 9/2009 | Van Os ................. G06F 3/0488 715/780 |
| 2011/0009824 A1 | 1/2011 | Yodfat et al. |
| 2011/0144616 A1 | 6/2011 | Michaud et al. |
| 2011/0190694 A1 | 8/2011 | Lanier, Jr. et al. |

FOREIGN PATENT DOCUMENTS

| | | |
|---|---|---|
| WO | WO95/28878 A | 11/1995 |
| WO | WO00/10628 A | 3/2000 |
| WO | WO2007/016145 A | 2/2007 |

OTHER PUBLICATIONS

International Search Report with Written Opinion, dated Sep. 17, 2010, received in international patent application No. PCT/US2010/028689, 17 pages.

International Search Report, dated Jan. 4, 2011, received in International Patent Application No. PCT/US2009/039169.

International Search Report with Written Opinion, dated Mar. 17, 2011, received in international patent application No. PCT/US2009/0396169, 24 pages.

International Preliminary Report on Patentability with Written Opinion, dated Mar. 31, 2011, received in international patent application No. PCT/US2009/0396169, 17 pages.

International Preliminary Report on Patentability with Written Opinion, dated Oct. 6, 2011, received in international patent application No. PCT/US2010/028689, 10 pages.

International Search Report & Written Opinion, dated Mar. 7, 2013, received in International patent application No. PCT/US2012/71280 (K11WO) 13 pgs.

\* cited by examiner

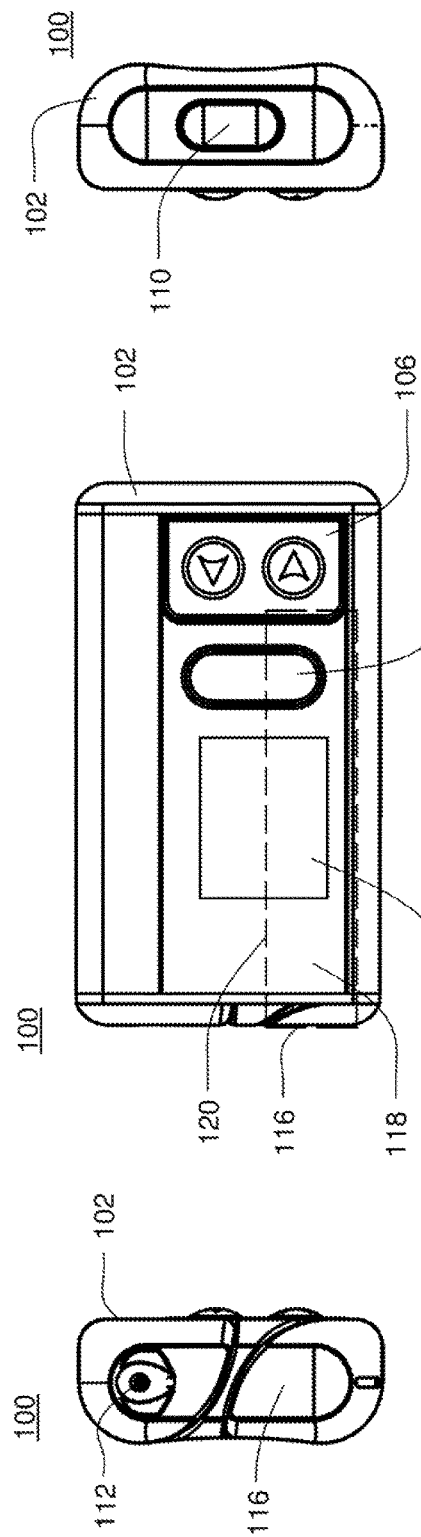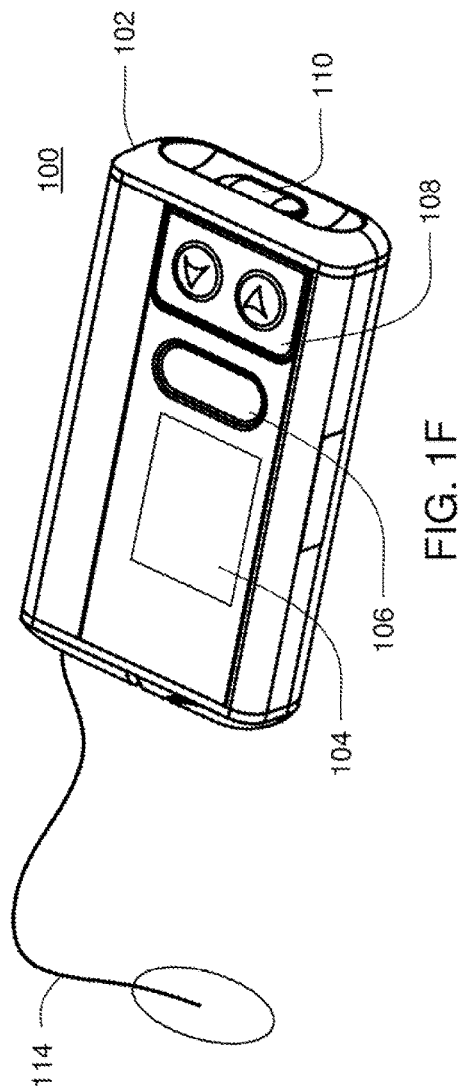

No Companions in
Pairing Mode
Found

Pairing was
Accepted on
Companion

User Interrupted
Pairing with Button
Press

Accept Next when a
Value Is Set To Dashes

SETUP screen
Stop Delivery Warning

Companion not
Communicating with
Pump

Clear the Alarm

Alarm after 15 minutes

STOPPED ALERT
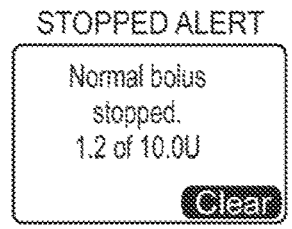
Clear the Alarm
FIG. 20E
CANCELLED ALERT     CANCELLATION ALERT
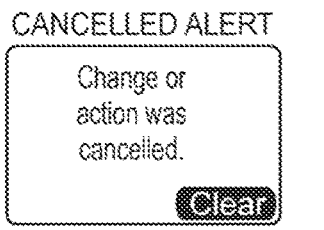 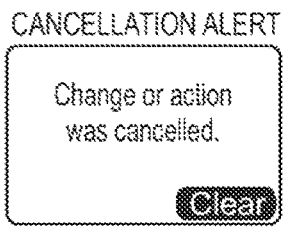
Clear the Alert    Alert Screen Displayed
                   on the Companion
FIG. 20F
CHECK BG ALERT
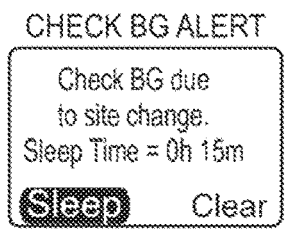
Default Selection
FIG. 20G
SITE CHANGE ALERT
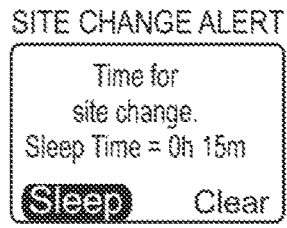
Default Selection
FIG. 20H No Bolus History/More
than 10 Boluses within
the Defined Action
Time

| HISTORY | HISTORY 1 of 3 | HISTORY 2 of 3 | HISTORY 3 of 3 |
|---|---|---|---|
| None | Normal Bolus 0.09 of 0.9U 1h 30m ago | Normal Bolus 0.5 of 0.5U 1h 32m ago | Normal Bolus 0.27 of 0.3U 28h 25m ago |
| Next Done | Next Done | Next Done | Next Done |

Display "None" when no bolus history; Only three boluses in history (1 of 3, 2 of 3, 3 of 3) History includes up to 10 boluses; user interface displays records for most recently completed 10.

| Jun 01, 2008 8:57 AM | May 27, 2008 8:57 AM | May 19, 2008 3:09 PM | May 19, 2008 2:54 PM |
|---|---|---|---|
| STOPPED ALERT  [Next]  Done | Error 0516 Info: 0, 0.0  [Next]  Done | INACTIVITY ALARM  [Next]  Done | INACTIVITY ALERT  [Next]  Done |
| May 9, 2008 7:09 PM | May 9, 2008 7:09 PM | May 9, 2008 7:09 PM | May 9, 2008 7:09 PM |
| BAD BATTERY ALARM  [Next]  Done | NO INSULIN ALARM  [Next]  Done | RESERVOIR ALARM  [Next]  Done | OCCLUSION ALARM  [Next]  Done |
| May 31, 2008 7:20 PM | May 31, 2008 2:29 PM | May 31, 2008 7:20 PM | May 31, 2008 7:20 PM |
| CHECK BG ALERT  [Next]  Done | SITE CHANGE ALERT  [Next]  Done | LOW TEMP ALERT  [Next]  Done | HIGH TEMP ALERT  [Next]  Done |
| Jun 01, 2008 9:00 AM | Jun 01, 2008 9:00 AM | Jun 01, 2008 9:00 AM | Jun 01, 2008 9:00 AM |
| Snack Reminder  [Next]  Done | Pickup Reminder  [Next]  Done | Bolus Reminder  [Next]  Done | Check BG Reminder  [Next]  Done |
| May 9, 2008 7:09 PM | May 9, 2008 7:09 PM | May 9, 2008 7:09 PM | DIARY |
| LOW INSULIN ALERT  [Next]  Done | LOW BATTERY ALERT  [Next]  Done | PUMP IDLE ALERT  [Next]  Done | None  [Next]  Done |

0 Alarms Logged

FIG. 30

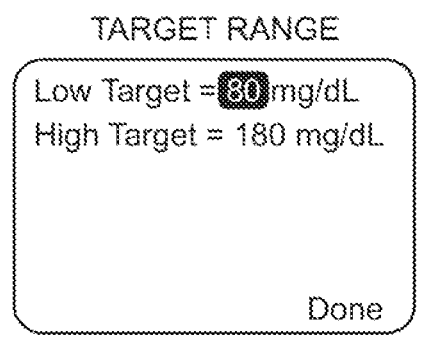
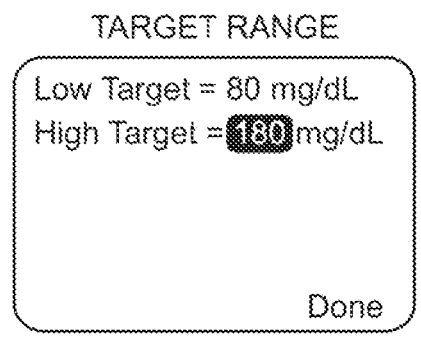
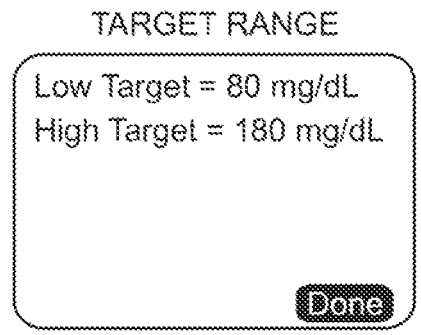
FIG. 37A

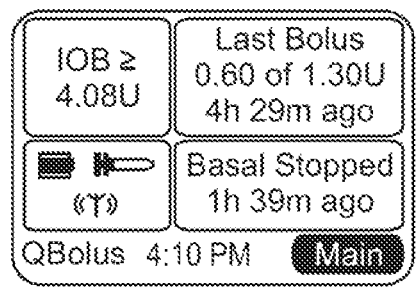
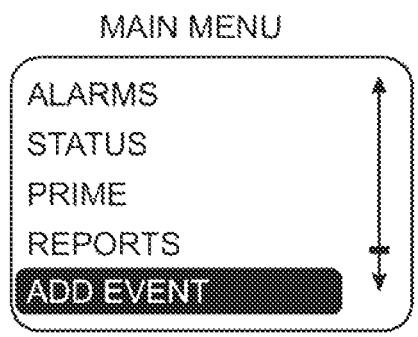
FIG. 41

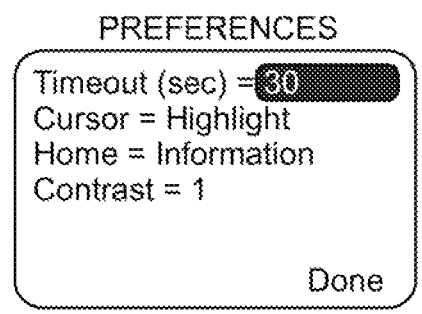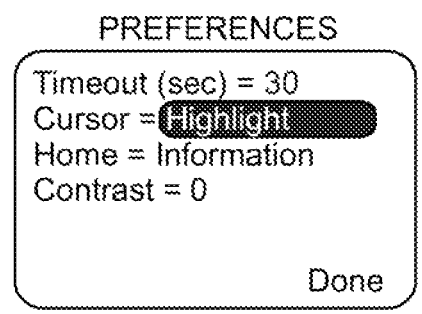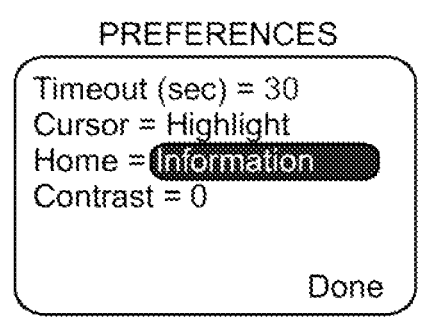
FIG. 44

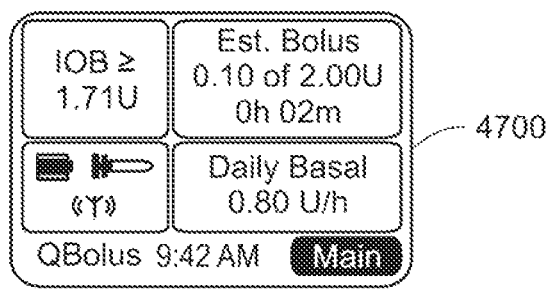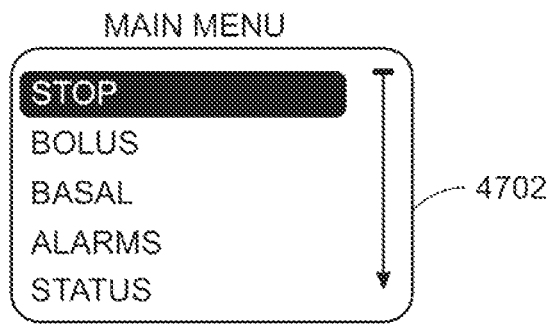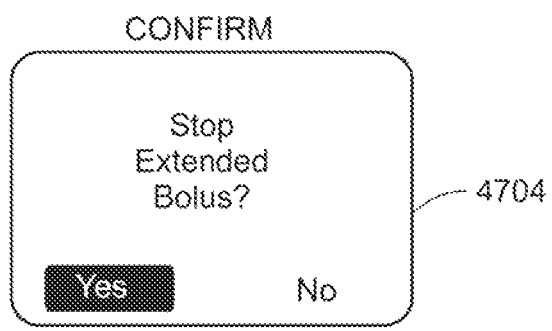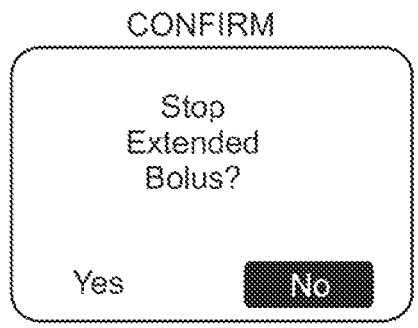
FIG. 47

INFUSION PUMP METHODS AND SYSTEMS

CROSS REFERENCE TO RELATED APPLICATIONS

The present application is a Non-Provisional Application which claims priority from U.S. Provisional Patent Application Ser. No. 61/163,273, filed Mar. 25, 2009 and entitled Medical Devices and Systems, Apparatus and Methods Thereof, (H21) which is hereby incorporated herein by reference in its entirety.

The present application is also a Continuation-In-Part Application of U.S. patent application Ser. No. 12/416,662, filed Apr. 1, 2009 and entitled Methods and Systems for Controlling an Infusion Pump, now U.S. Publication No. US-2009-0254037, published Oct. 8, 2009 (G98) which claims priority from U.S. Provisional Patent Application 61/165,592, filed Apr. 1, 2009 and entitled Methods and Systems for Controlling a Medical Device, (H24) and U.S. Patent Application Ser. No. 61/041,291 filed Apr. 1, 2008 and entitled Methods and Systems for Controlling a Medical Device, (F76), all of which are hereby incorporated herein by reference in their entireties.

TECHNICAL FIELD

The present invention relates to infusion pumps and more particularly, to infusion pump methods and systems.

BACKGROUND INFORMATION

Many potentially valuable medicines or compounds, including biologicals, are not orally active due to poor absorption, hepatic metabolism or other pharmacokinetic factors. Additionally, some therapeutic compounds, although they may be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of people living with diabetes. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks. Reducing the size, weight and cost of these devices is also an ongoing challenge.

Additionally, many of these devices require frequent and direct interaction between the device and the user, or the device and a caregiver. Thus, in these cases, it is often desired that the device be worn clipped to clothing or a belt, or in a pocket, thus being accessible in any situation. However, this is not always practical or possible. Thus, there is a desire for a device that may be controlled by a remote device such that the user or caregiver does not require frequent direct interaction.

Further, safety is an ongoing concern with any medical device. Thus, systems and methods that impart added safety to the user are desired.

SUMMARY

In accordance with one aspect of the present invention, an infusion pump system is disclosed. The system includes at least one infusion pump, a companion device, the companion device in wireless communication with the infusion pump, and a user interface on the companion device, the user interface adapted to receive textual input.

Some embodiments of this aspect of the present invention may include one or more of the following. Wherein the textual input comprising customized names for at least one basal profile. Wherein the textual input includes at least one customized comment. Wherein the textual input includes at least one customized events. Wherein the system further includes a pairing mode for pairing the companion device with the at least one infusion pump, the pairing mode enabling wireless communication between one infusion pump and the controller device, wherein the user interface requires both the infusion pump and the controller to be in the pairing mode simultaneously. Where the companion includes a display. Wherein the at least one infusion pump includes a display. Wherein the user interface includes at least one alarm setting for the infusion pump and the companion device, the at least one alarm setting may be selected using the user interface and wherein the at least one alarm setting for the infusion pump and the companion device may be different. Wherein the user interface residing on the at least one infusion pump. Wherein the user interface user interface comprising visual indication of a bolus delivery in progress comprising an amount delivered and a total amount requested. Wherein the when the bolus delivery is stopped, the user interface further comprising a visual indication of delivery stopped comprising indication of the amount delivered and the total amount requested. Wherein the user interface further includes a home screen comprising visual indication of insulin on board and last bolus delivered, the last bolus delivered comprising the time elapsed since delivery completed and the amount delivered.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIGS. 1C-1E are side and front views of one embodiment of an infusion pump assembly of FIG. 1;

FIG. 1F is a front isometric view of one embodiment of an infusion pump assembly of FIG. 1;

FIGS. 11A-11B shows an exemplary embodiment of at least a selection of 1 U DROP screens;

FIGS. 20A-20I shows exemplary embodiments of at least a selection of ALERT screens;

FIG. 25 shows an exemplary embodiment of at least a selection of HISTORY screens;

FIGS. 29A-29B shows an exemplary embodiment of at least a selection of EVENT SUMMARY screens;

FIG. 30 shows an exemplary embodiment of at least a selection of ALARM SUMMARY screens;

FIG. 37A-37B show an embodiment of target screens;

FIG. 41 shows an embodiment of add event screens;

FIG. 44 shows an embodiment of a preference screens;

FIG. 47 shows an embodiment of stop extended bolus screens;

DETAILED DESCRIPTION OF THE PREFERRED EMBODIMENTS

Definitions

Figure 1A:
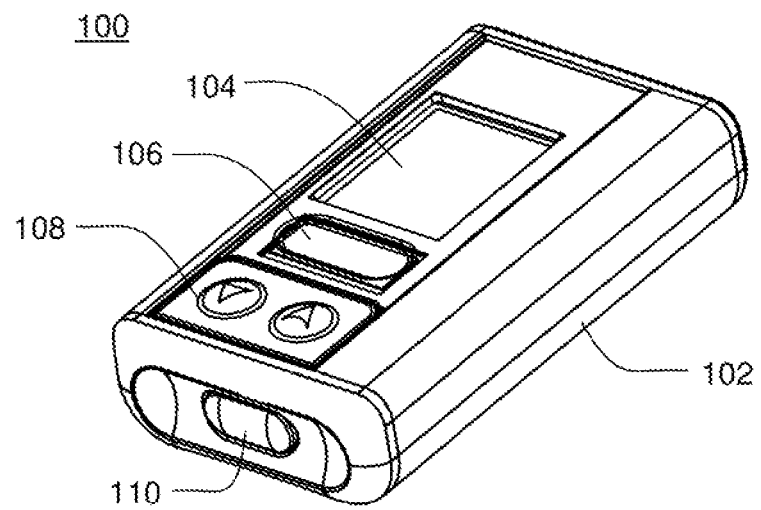
FIGS. 1A-1B are front and back isometric views of one embodiment of an infusion pump assembly.
Figure 1B:
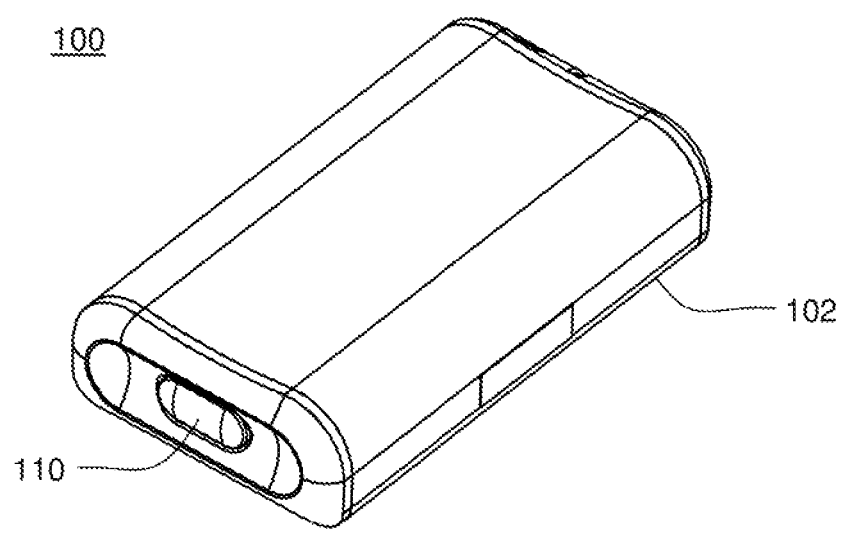

As used in this description and the accompanying claims, the following terms shall have the meanings indicated, unless the context otherwise requires:

A "device" shall mean a medical device, which includes, but is not limited to, an infusion pump and/or a controller, i.e., a device for wireless control of another medical device. In some embodiments, the word "device" is used interchangeably with "pump", "infusion pump" and/or "controller" and/or "Companion" and/or "remote controller device" and/or "remote controller assembly".

A "Companion" shall mean a device for wireless control of another medical device. In the exemplary embodiments, the Companion may also include a glucose meter/strip reader. In some embodiments, the Companion may include a receiver for receiving continuous glucose monitor signals from at least one continuous glucose monitor sensor.

An "input" of a device includes any mechanism by which a user of the device or other operator/caregiver may control a function of the device. User inputs may include mechanical arrangements (e.g., switches, pushbuttons, jogwheel(s)), electrical arrangements (e.g., a slider, touch screen), wireless interfaces for communication with a remote controller (e.g., RF, infrared), acoustic interfaces (e.g., with speech recognition), computer network interfaces (e.g., USB port), and other types of interfaces.

A "button" in the context of an input such as the so-called "bolus button" discussed below may be any type of user input capable of performing a desired function, and is not limited to a pushbutton, a slider, switch, touch screen or a jog wheel.

An "alarm" includes any mechanism by which an alert may be generated to a user or third party. Alarms may include audible alarms (e.g., a speaker, a buzzer, a speech generator), visual alarms (e.g., an LED, an LCD screen), tactile alarms (e.g., a vibrating element), wireless signals (e.g., a wireless transmission to a remote controller or caretaker), or other mechanism. Alarms may be generated using multiple mechanisms simultaneously, concurrently, or in a sequence, including redundant mechanisms (e.g., two different audio alarms) or complementary mechanisms (e.g., an audio alarm, a tactile alarm, and a wireless alarm).

"Fluid" shall mean a substance, a liquid for example, that is capable of flowing through a flow line.

A "user" includes a person or animal who receives fluid from a fluid delivery device, whether as part of a medical treatment or otherwise, or a caregiver or third party involved in programming the device or otherwise interacting with the device to infuse fluid to another.

"Cannula" shall mean a disposable device capable of infusing fluid to a user. A cannula as used herein may refer to a traditional cannula or to a needle.

"Disposable" refers to a part, device, portion or other that is intended to be used for a fixed duration of time, then discarded and replaced.

"Reusable" refers to a portion that is intended to have an open-ended duration of use.

"Acoustic volume measurement" shall mean quantitative measurement of a relevant volume using acoustical techniques such as described in U.S. Pat. Nos. 5,349,852 and 5,641,892 (both of which are herein incorporated by reference in their entireties) as well as other techniques incorporated by reference herein.

A "temperature sensor" includes any mechanism for measuring temperature and communicating temperature information to a controller or to a pump processor. The devices described herein may include one or more temperature sensors for measuring such things as including, but not limited to, one or more of the following: skin temperature, AVS temperature, ambient temperature, internal temperature and fluid temperatures.

An exemplary use of embodiments of the devices, methods and systems described here is for the delivery of insulin to people living with diabetes, but other uses include delivery of any fluid, as described above. Fluids include analgesics to those in pain, chemotherapy to cancer patients and enzymes to patients with metabolic disorders. Various therapeutic fluids may include small molecules, natural products, peptide, proteins, nucleic acids, carbohydrates, nanoparticulate suspensions, and associated pharmaceutically acceptable carrier molecules. Therapeutically active molecules may be modified to improve stability in the device (e.g., by pegylation of peptides or proteins). Although illustrative embodiments herein describe drug-delivery applications, embodiments may be used for other applications including liquid dispensing of reagents for high throughput analytical measurements such as lab-on-chip applications and capillary chromatography. For purposes of description below, terms "therapeutic", "insulin" or "fluid" are used interchangeably, however, in other embodiments, any fluid, as described above, may be used. Thus, the device and description included herein are not limited to use with therapeutics.

Some embodiments of the fluid delivery device are adapted for use by people living with diabetes and/or their caregivers. Thus, in these embodiments, the devices, methods and systems work to delivers insulin which supplements or replaces the action of the person living with diabetes' (referred to as the user) pancreatic islet beta cells. Embodiments adapted for insulin delivery seek to mimic the action of the pancreas by providing both a basal level of fluid delivery as well as bolus levels of delivery. Basal levels, bolus levels and timing may be set by the user or a caregiver by using a wireless handheld user interface or directly by using a pump. Additionally, basal and/or bolus levels may be triggered or adjusted in response to the output of a glucose meter and/or signals from a continuous glucose monitor, one or more of which, in the exemplary embodiments, may be integral to the controller. Thus, in some embodiments, the controller additionally includes a glucose monitoring device which may receive data from a blood glucose sensor and/or from an interstitial glucose sensor. In some embodiments, a bolus may be triggered by a user using a designated button or other input means located on a device, i.e., on the controller and/or on an infusion pump. In still other embodiments, the bolus or basal may be programmed or administered through a user interface located either on the fluid delivery device/infusion pump and/or on the controller.

With respect to the names given to screens and types of screens, as well as proper names given to various features, throughout various embodiments, these terms may vary.

The systems and methods described herein may be used to control an infusion pump. For purposes of this description, the various embodiments of the user interface and the infusion pump may be described with reference to an insulin pump, or a pump which infuses insulin. However, it should be understood that the user interface may be on any infusion pump and/or on a controller. Additionally, where the description pertains to an infusion pump "screen", this "screen" may also appear on a controller, or may appear on a controller in lieu of a pump, and/or, in some embodiments, the screen may appear on the infusion pump.

Infusion pumps contemplated by this description include a pump which may pump any fluid, including, but not limited to, a therapeutic fluid, which includes, but is not limited to, insulin. Thus, where this description describes the exemplary embodiment as pertaining to insulin, this is meant merely for descriptive purpose only as the device is not intended to be limited to insulin. Other fluids are also contemplated.

The infusion pump may be any infusion pump, for example, but not limited to, the pump devices shown and described with respect to FIGS. 1A-1F and 2A-2D, and include, but are not limited to, those described in U.S. patent application Ser. No. 11/704,899, filed Feb. 9, 2007 and entitled Fluid Delivery Systems and Method, now U.S. Publication No. US-2007-0228071, published on Oct. 4, 2007 (E70); U.S. patent application Ser. No. 11/704,896, filed Feb. 9, 2007 and entitled Pumping Fluid Delivery Systems and Methods Using Force Application Assembly, now U.S. Publication No. US-2007-0219496, published on Sep. 20, 2007 (E71); U.S. patent application Ser. No. 11/704,886, filed Feb. 9, 2007 and entitled Patch-Sized Fluid Delivery Systems and Methods, now U.S. Publication No. US-2007-0219480, published on Sep. 20, 2007 (E72); U.S. patent application Ser. No. 11/704,897, filed Feb. 9, 2007 and entitled Adhesive and Peripheral Systems and Methods for Medical Devices, now U.S. Publication No. US-2007-0219597, published on Sep. 20, 2007 (E73); U.S. patent application Ser. No. 12/347,985, filed Dec. 31, 2008 and entitled Infusion Pump Assembly, now U.S. Publication No. US-2009-0299277, published Dec. 3, 2009 (G75); U.S. patent application Ser. No. 12/347,982, filed Dec. 31, 2008 and entitled Wearable Pump Assembly, now U.S. Publication No. US 2009-0281497, published Nov. 12, 2009 (G76); U.S. patent application Ser. No. 12/347,981, filed Dec. 31, 2008 and entitled Infusion Pump Assembly, now U.S. Publication No. US-2009-0275896, published Nov. 5, 2009 (G77); U.S. patent application Ser. No. 10/037,614, filed Jan. 4, 2002 and entitled Loading Mechanism for Infusion Pump, now U.S. Pat. No. 7,306,578, issued on Dec. 11, 2007 (C54); U.S. patent application Ser. No. 12/249,891, filed Oct. 10, 2008 and entitled Infusion Pump Assembly, now U.S. Publication No. US-2009-0099523, published Apr. 16, 2009 (G46); U.S. patent application Ser. No. 12/249,882, filed Oct. 10, 2008 and entitled Infusion Pump Assembly (F51); U.S. patent application Ser. No. 12/249,636, filed Oct. 10, 2008 and entitled System and Method for Administering an Infusible Fluid (F52); U.S. patent application Ser. No. 12/249,621, filed Oct. 10, 2008 and entitled Occlusion Detection System and Method (F53); U.S. patent application Ser. No. 12/249,600, filed Oct. 10, 2008 and entitled Multi-Language/Multi-Processor Infusion Pump Assembly (F54);

U.S. patent application Ser. No. 12/249,540, filed Oct. 10, 2008 and entitled An Infusion Pump Assembly with a Backup Power Supply (F55); and U.S. patent application Ser. No. 12/249,496, filed Oct. 10, 2008 and entitled Pump Assembly with a Removable Cover Assembly (F56), all of which are herein incorporated by reference in their entireties. In the exemplary embodiment, the infusion pump includes hardware for wireless RF communication with a controller. However, in various embodiments, the infusion pump may be any infusion pump. Referring to FIGS. 1A-1F and 2A-2D, in some exemplary embodiments, the infusion pump may include a display assembly 104, however, in other exemplary embodiments, such as those shown in FIGS. 2A-2D, the infusion pump may not include a display assembly. In these embodiments, a display assembly which may be similar to the one shown in FIGS. 1A, 1D and 1F, or may be larger or smaller, is included on a controller or companion device. An embodiment of the controller or companion device is shown in FIG. 3.

Referring to FIGS. 1A-1F, an embodiment of an infusion pump assembly 100 that may be housed within enclosure assembly 102 is shown. Infusion pump assembly 100 may include a display system 104 that may be visible through the enclosure assembly 102. One or more switch assemblies/input devices 106, 108, 110 may be positioned about various portions of the enclosure assembly 102. The enclosure assembly 102 may include infusion port assembly 112 to which cannula assembly 114 may be releasably coupled. A removable cover assembly 116 may allow access to a power supply cavity 118 (shown in phantom on FIG. 1D).

Figure 4:
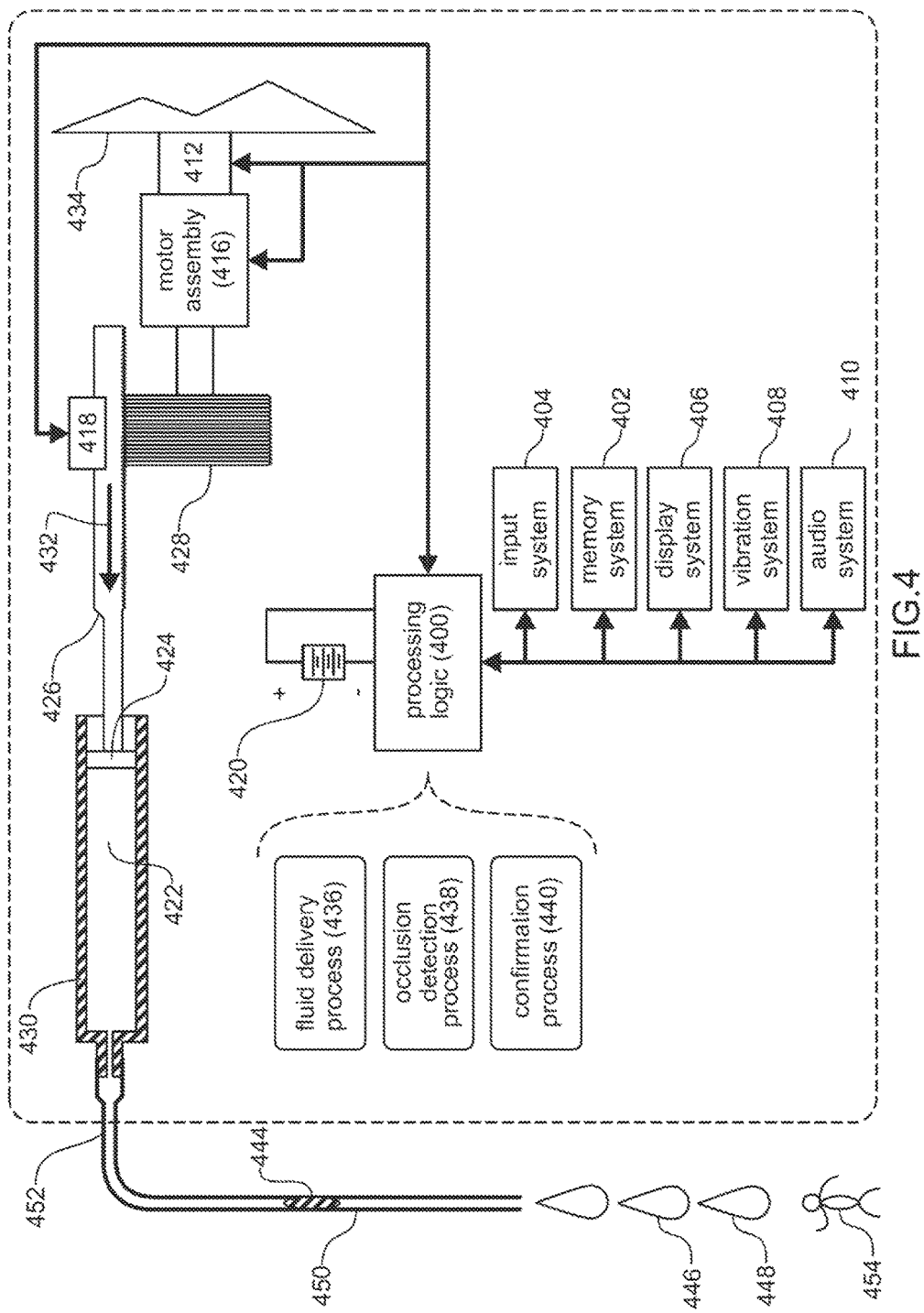
FIG. 4 is a diagrammatic view of the infusion pump assembly of FIG. 1.

Referring to the infusion pump assemblies shown in FIG. 1A-1F, infusion pump assembly 100 may include processing logic (not shown) that executes one or more processes that may be required for infusion pump assembly 100 to operate properly. Processing logic may include one or more microprocessors (not shown), one or more input/output controllers (not shown), and cache memory devices (not shown). One or more data buses and/or memory buses may be used to interconnect processing logic with one or more subsystems. In some embodiments, at least one of the subsystems shown in FIG. 4 is also included in the embodiment of the infusion pump assembly 200 shown in FIGS. 2A-2D.

The various embodiment of the infusion pump shown in FIGS. 2A-2D include those described in U.S. Pat. No. 5,575,310, issued Nov. 19, 1996 and entitled Flow Control System with Volume-Measuring System Using a Resonatable Mass (B28); and U.S. Pat. No. 5,755,683, issued May 26, 1998 and entitled Cassette for Intravenous-Line Flow-Control System (B13), both of which are assigned to DEKA Products Limited Partnership, as well as U.S. patent application Ser. No. 11/704,899, filed Feb. 9, 2007 and entitled Fluid Delivery Systems and Methods, now U.S. Publication No. US-2007-0228071, published on Oct. 4, 2007 (E70); U.S. patent application Ser. No. 11/704,896, filed Feb. 9, 2007 and entitled Pumping Fluid Delivery Systems and Methods Using Force Application Assembly, now U.S. Publication No. US-2007-0219496, published on Sep. 20, 2007 (E71); U.S. patent application Ser. No. 11/704,886, filed Feb. 9, 2007 and entitled Patch-Sized Fluid Delivery Systems and Methods, now U.S. Publication No. US-2007-0219480, published on Sep. 20, 2007 (E72); U.S. patent application Ser. No. 11/704,897, filed Feb. 9, 2007 and entitled Adhesive and Peripheral Systems and Methods for Medical Devices, now U.S. Publication No. US-2007-0219597, published on Sep. 20, 2007 (E73); and U.S. patent application Ser. No. 12/347,985, filed Dec. 31, 2008 and entitled Infusion Pump Assembly, now U.S. Publication No. US-2009-0299277, published Dec. 3, 2009 (G75).

Referring to FIGS. 2A-2D, infusion pump assembly 200 may include a reusable housing assembly 202. Reusable housing assembly 204 may be constructed from any suitable material, such as a hard or rigid plastic, that will resist compression. For example, use of durable materials and parts may improve quality and reduce costs by providing a reusable portion that lasts longer and is more durable, providing greater protection to components disposed therein.

Reusable housing assembly 204 may include a mechanical control assembly (not shown) having a pump assembly and at least one valve assembly. The reusable housing assembly 204 may also include an electrical control assembly configured to provide one or more control signals to the mechanical control assembly and effectuate the basal and/or bolus delivery of an infusible fluid to a user. Disposable housing assembly 202 may include at least one valve assembly which may be configured to control the flow of the infusible fluid through a fluid path. Reusable housing assembly 204 may also include a pump assembly which may be configured to pump the infusible fluid from the fluid path to the user.

An electrical control assembly may be housed in the reusable housing assembly 204 and may monitor and control the amount of infusible fluid that has been and/or is being pumped. For example, electrical control assembly may receive signals from a volume sensor assembly and calculate the amount of infusible fluid that has just been dispensed and determine, based upon the dosage required by the user, whether enough infusible fluid has been dispensed. If enough infusible fluid has not been dispensed, electrical control assembly may determine that more infusible fluid should be pumped. Electrical control assembly may provide the appropriate signal to mechanical control assembly so that any additional necessary dosage may be pumped or electrical control assembly may provide the appropriate signal to mechanical control assembly so that the additional dosage may be dispensed with the next dosage. Alternatively, if too much infusible fluid has been dispensed, electrical control assembly may provide the appropriate signal to mechanical control assembly so that less infusible fluid may be dispensed in the next dosage.

The mechanical control assembly may include at least one shape-memory actuator. The pump assembly and/or valve assembly of the mechanical control assembly may be actuated by at least one shape-memory actuator, e.g., shape-memory actuator, which may be a shape-memory wire in wire or spring configuration. Shape memory actuator may be operably connected to and activated by an electrical control assembly, which may control the timing and the amount of heat and/or electrical energy used to actuate mechanical control assembly. Shape memory actuator may be, for example, a conductive shape-memory alloy wire that changes shape with temperature. The temperature of shape-memory actuator may be changed with a heater, or more conveniently, by application of electrical energy. Shape memory actuator may be a shape memory wire constructed of nickel/titanium alloy, such as NITINOL™ or FLEXINOL®.

Infusion pump assembly 200 may include a volume sensor assembly configured to monitor the amount of fluid infused by infusion pump assembly. For example, the volume sensor assembly may employ, for example, acoustic volume sensing using acoustic volume measurement technology, including, but not limited to, technologies described in the following references: U.S. Pat. No. 5,575,310 entitled Flow Control System With Volume-Measuring System Using a Resonatable Mass (B28) and U.S. Pat. No. 5,755,683 entitled Cassette for Intravenous-Line Flow-Control System (B13), both assigned to DEKA Products Limited Partnership, as well as U.S. patent application Ser. No. 11/704,899, filed Feb. 9, 2007 and entitled Fluid Delivery Systems and Methods, now U.S. Publication No. US-2007-0228071, published Oct. 4, 2007 (E70); U.S. patent application Ser. No. 11/704,896, filed Feb. 9, 2007 and entitled. Pumping Fluid Delivery Systems and Methods Using Force Application Assembly, now U.S. Publication No. US-2007-0219496, published Sep. 20, 2007 (E71); U.S. patent application Ser. No. 11/704,886, filed Feb. 9, 2007 and entitled Patch-Sized Fluid Delivery Systems and Methods, now U.S. Publication No. US-2007-0219480, published Sep. 20, 2007 (E72); and U.S. patent application Ser. No. 11/704,897, filed Sep. 9, 2007 and entitled Adhesive and Peripheral Systems and Methods for Medical Devices, now U.S. Publication No. US-2007-0219597, published Sep. 20, 2007 (E73), all of which are incorporated herein by reference in their entirety. Other alternative techniques for measuring fluid flow may also be used; for example, Doppler-based methods; the use of Hall-effect sensors in combination with a vane or flapper valve; the use of a strain beam (for example, related to a flexible member over a fluid reservoir to sense deflection of the flexible member); the use of capacitive sensing with plates; or thermal time of flight methods. One such alternative technique is disclosed in U.S. patent application Ser. No. 11/704,899, filed Feb. 9, 2007 and entitled Fluid Delivery Systems and Methods, now Publication No. US-2007-0228071, published on Oct. 4, 2007 E70), of which is incorporated herein by reference in its entirety. Infusion pump assembly 200 may be configured so that the volume measurements produced by the volume sensor assembly may be used to control, through a feedback loop, the amount of infusible fluid that is infused into the user.

Infusion pump assembly 200 may further include a disposable housing assembly 202. For example, disposable housing assembly 202 may be configured for a single use or for use for a specified period of time, e.g., three days or any other amount of time. Disposable housing assembly 202 may be configured such that any components in infusion pump assembly 200 that come in contact with the infusible fluid are disposed on and/or within disposable housing assembly 202. For example, a fluid path or channel including a reservoir, may be positioned within disposable housing assembly 202 and may be configured for a single use or for a specified number of uses before disposal. The disposable nature of disposable housing assembly 202 may improve sanitation of infusion pump assembly 200.

The disposable housing assembly 202 may be configured to releasably engage reusable housing assembly 204, and includes a cavity that has a reservoir for receiving an infusible fluid (not shown), e.g., insulin. Such releasable engagement may be accomplished by a screw-on, a twist-lock or a compression fit configuration, for example. Disposable housing assembly 202 and/or reusable housing assembly 204 may include an alignment assembly configured to assist in aligning disposable housing assembly 202 and reusable housing assembly 204 for engagement in a specific orientation. Similarly, base nub 206 and top nub 208 may be used as indicators of alignment and complete engagement.

Figure 2A:
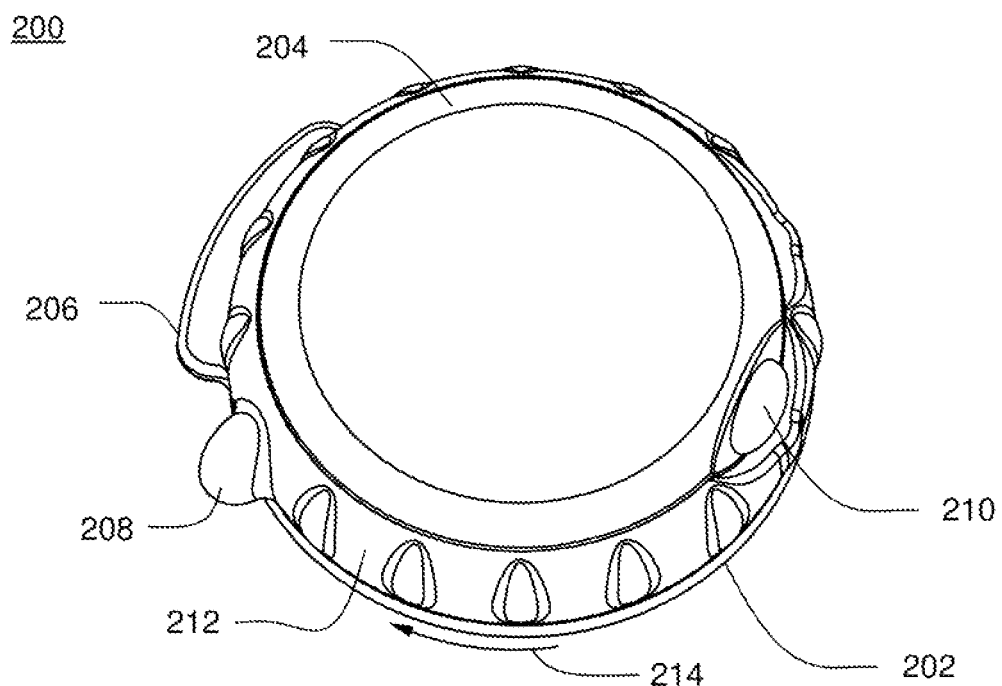
FIGS. 2A-2D are various view of an exemplary embodiment of an infusion pump assembly.
Figure 2B:
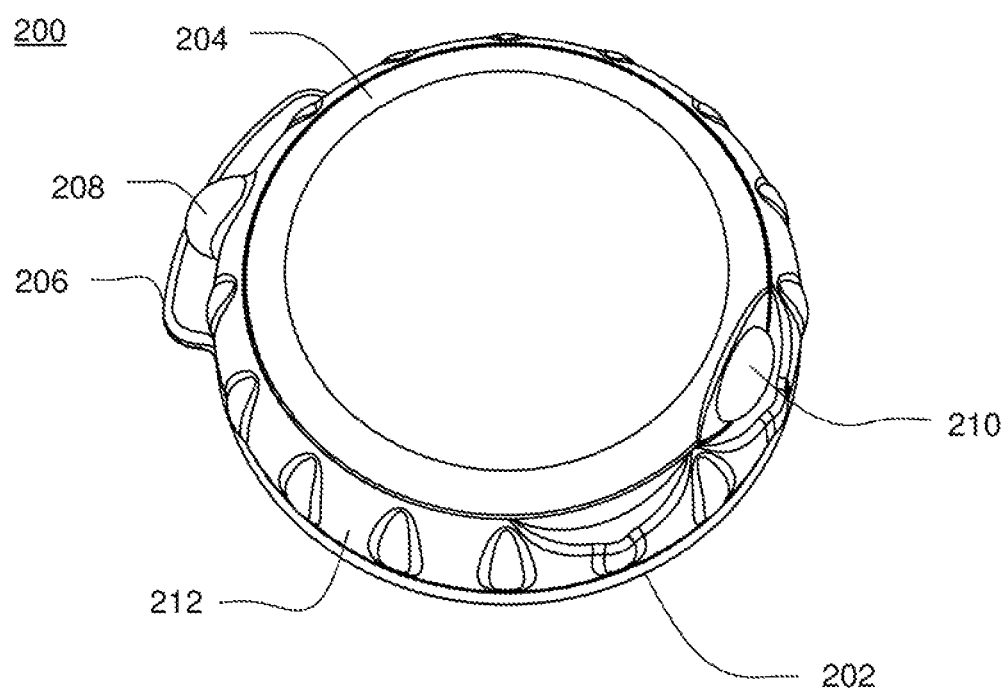
Figure 2C:
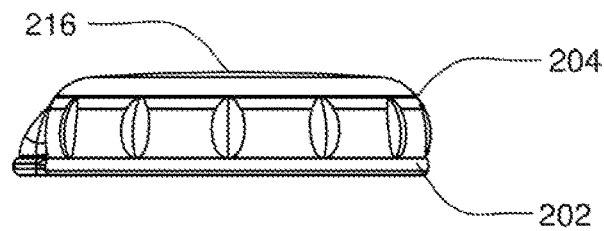
Figure 2D:
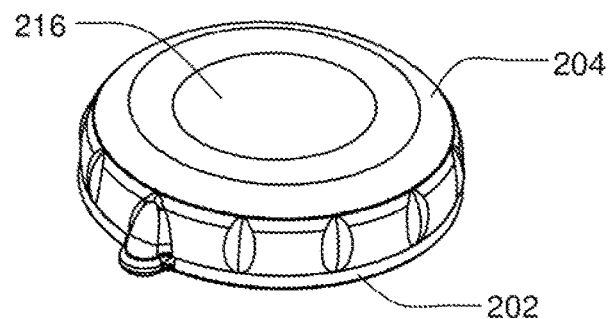
Figure 3:
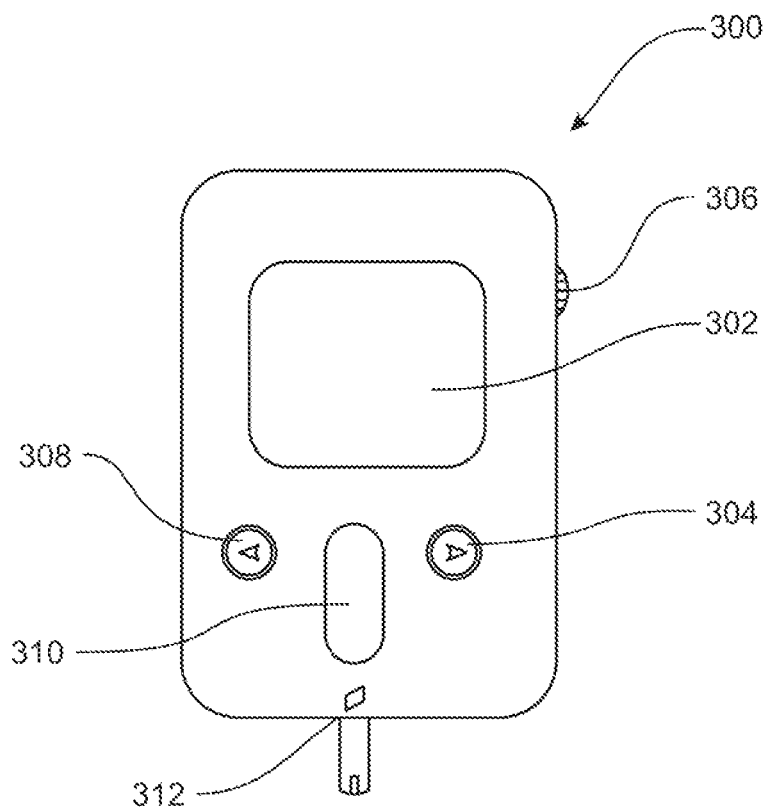
FIG. 3 is an illustrative view of one embodiment of a remote controller or companion assembly.

Referring now to FIGS. 2A-2B, in this particular embodiment of the infusion pump assembly 200, infusion pump assembly 200 may include switch assembly 210 positioned about the periphery of infusion pump assembly 200. In other embodiments, for example, those shown in FIGS. 2C-2D, the switch assembly 216 may be positioned elsewhere on the reusable housing assembly 204, including but not limited to, on the top surface. Referring back to FIGS. 2A-2B, in the exemplary embodiment shown, switch assembly 210 may be positioned along a radial edge of infusion pump assembly 200, which may allow for easier use by a user. Switch assembly 210 may be covered with a waterproof membrane configured to prevent the infiltration of water into infusion pump assembly 200. Reusable housing assembly 204 may include main body portion (housing the above-described mechanical and electrical control assemblies) and locking ring assembly 212 that may be configured to rotate about main body portion (in the direction of arrow 214).

In a fashion similar to reusable housing assembly 204 and disposable housing assembly 202, reusable housing assembly 204 may be configured to releasably engage disposable housing assembly 202. Such releasable engagement may be accomplished by a screw-on, a twist-lock or a compression fit configuration, for example. In an embodiment in which a twist-lock configuration is utilized, the user of infusion pump assembly 200 may first properly position reusable housing assembly 204 with respect to disposable housing assembly 202 and may then rotate locking ring assembly 212 (in the direction of arrow 214) to releasably engage reusable housing assembly 204 with disposable housing assembly 202.

Through the use of locking ring assembly 212, reusable housing assembly 204 may be properly positioned with respect to disposable housing assembly 202 and then releasably engaged by rotating locking ring assembly 212, thus eliminating the need to rotate reusable housing assembly 204 with respect to disposable housing assembly 202. Accordingly, reusable housing assembly 204 may be properly aligned with disposable housing assembly 202 prior to engagement, and such alignment may not be disturbed during the engagement process. Locking ring assembly 212 may include a latching mechanism (not shown) that may prevent the rotation of locking ring assembly 212 until reusable housing assembly 204 and disposable housing assembly 202 are properly positioned with respect to each other.

Referring now to FIGS. 1A-1F and FIG. 4, examples of the subsystems interconnected with processing logic 400 may include but are not limited to memory system 402, input system 404, display system 406, vibration system 408, audio system 410 motor assembly 416, force sensor 412, temperature sensor (not shown) and displacement detection device 418. Infusion pump assembly 100 may include primary power supply 420 (e.g. a battery) configured to be removable installable within power supply cavity 118 and to provide electrical power to at least a portion of processing logic 400 and one or more of the subsystems (e.g., memory system 402, input system 404, display system 406, vibration system 408, audio system 410, motor assembly 416, force sensor 412, and displacement detection device 418).

Infusion pump assembly 100 may include reservoir assembly 430 configured to contain infusible fluid 422. In some embodiments, reservoir assembly 430 may be a reservoir assembly similar to that described in U.S. Pat. No. 7,498,563, issued Mar. 3, 2009 and entitled Optical Displacement Sensor for Infusion Devices (D78), which is herein incorporated by reference in its entirety, and/or as described in U.S. Pat. No. 7,306,578, issued Dec. 11, 2007 and entitled Loading Mechanism for Infusion Pump (C54); U.S. patent application Ser. No. 12/249,882, filed Oct. 10, 2008 and entitled Infusion Pump Assembly (F51); and U.S. patent application Ser. No. 12/249,891, filed Oct. 10, 2008 and entitled Infusion Pump Assembly, now U.S. Publication No US-2009-0099523, published Apr. 16, 2009 (G46), all of which are herein incorporated by reference in their entireties. In other embodiments, the reservoir assembly may be any assembly in which fluid may be acted upon such that at least a portion of the fluid may flow out of the reservoir assembly, for example, the reservoir assembly, in various embodiments, may include but is not limited to: a barrel with a plunger, a cassette or a container at least partially constructed of a flexible membrane.

Plunger assembly 424 may be configured to displace infusible fluid 422 from reservoir assembly 430 through cannula assembly 450 (which may be coupled to infusion pump assembly 100 via infusion port assembly 424) so that infusible fluid 422 may be delivered to user 454. In this particular embodiment, plunger assembly 424 is shown to be displaceable by partial nut assembly 426, which may engage lead screw assembly 428 that may be rotatable by motor assembly 416 in response to signals received from processing logic 400. In this particular embodiment, the combination of motor assembly 416, plunger assembly 424, partial nut assembly 426, and lead screw assembly 428 may form a pump assembly that effectuates the dispensing of infusible fluid 422 contained within reservoir assembly 430. An example of partial nut assembly 426 may include but is not limited to a nut assembly that is configured to wrap around lead screw assembly 426 by e.g., 30 degrees. In some embodiments, the pump assembly may be similar to one described in U.S. Pat. No. 7,306,578, issued Dec. 11, 2007 and entitled Loading Mechanism for Infusion Pump (C54); U.S. patent application Ser. No. 12/249,882, filed Oct. 10, 2008 and entitled Infusion Pump Assembly (F51); and U.S. patent application Ser. No. 12/249,891, filed Oct. 10, 2008 and entitled Infusion Pump Assembly, now U.S. Publication No. US-2009-0099523, published Apr. 16, 2009 (G46) all of which are herein incorporated by reference in their entireties.

User Interface

Throughout this description, screens may be referenced with respect to the "pump" or "Companion" or "Controller". However, in various embodiments, a similar screen or a similar method may be accomplished on another device. For example, where the screen or method is referenced with respect to the "pump", a similarly functional screen or method may be used on the "Companion" in other embodiments. As this description includes embodiments related to both pumps having displays and pumps having no displays, it should be evident that where the embodiment includes an infusion pump without a display, any screens will be visible on at least one Companion. Similarly, where a method requires an interaction between the user and the pump, the interaction may be accomplished via a switch assembly on the pump where the pump is an infusion pump without a display.

Processing logic which in some embodiments, includes at least one element as shown and described with respect to FIG. 4, is used to receive inputs from a user or caregiver. The user or caregiver uses one or more input devices or assemblies, including but not limited to, one or more of the following: button/switch assembly, slider (for example, including but not limited to any slider described in U.S. patent application Ser. No. 11/999,268, filed Dec. 4, 2007 and entitled Medical Device Including a Slider Assembly, now U.S. Publication No. US-2008-0177900, published Jul. 24, 2008, which is herein incorporated by reference in its entirety), jog wheel or touch screen. The infusion device additionally received inputs from internal systems, including but not limited to occlusion detection process 438, confirmation process 440, volume measurement technology (e.g., acoustic volume sensing). Using these inputs, the infusion device produces outputs, for example including, but not limited to, infusion fluid delivery to the user or comments, alerts, alarms or warnings to the user. The inputs are thus either directly from the user to the pump, directly from the pump systems to the processing logic, or from another device, e.g., a remote controller device (described in more detail below), to the pump. The user or caregiver interaction experience thus includes, but is not limited to, one or more of the following: interaction with a display (either on the infusion pump device itself or a remote controller device or both), which includes but is not limited to, reading/seeing text and/or graphics on a display, direct interaction with a display, for example, through a touch screen, interaction with one or more buttons, sliders, jog wheels, one or more glucose strip readers, and sensing either through touch sensation or audio, one or more vibration motors, and/or an audio system. Thus, the term "user interface" is used to encompass all of the systems and methods a user or caregiver uses to interact with the infusion pump, to control the infusion pump and/or to make therapy decisions.

Referring now to FIG. 3, in some embodiments of the infusion pump system, the infusion pump may be remotely controlled using a remote controller assembly 300, also referred to as a controller or a Companion. Remote control assembly 300 may include all, or a portion of, the functionality of the infusion pump assembly shown in FIGS. 1A-1F, itself. Thus, in some exemplary embodiments of the above-described infusion pump assembly, the infusion pump assembly (not shown, see FIGS. 1A-1F, amongst other FIGS.) may be configured via remote control assembly 300. In these particular embodiments, the infusion pump assembly may include telemetry circuitry (not shown) that allows for communication (e.g., wired or wireless) between the infusion pump assembly and e.g., remote control assembly 300, thus allowing remote control assembly 300 to remotely control infusion pump assembly 100. Remote control assembly 300 (which may also include telemetry circuitry (not shown) and may be capable of communicating with infusion pump assembly) may include display assembly 302 and an input assembly, which may include one or more of the following: an input control device (such as jog wheel 306, slider assembly 310, or another conventional mode for input into a device), and switch assemblies 304, 308. Thus, although remote control assembly 300 as shown in FIG. 3 includes jog wheel 306 and slider assembly 310, some embodiments may include only one of either jog wheel 306 or slider assembly 310, or another conventional mode for input into a device. In embodiments having jog wheel 306, jog wheel 306 may include a wheel, ring, knob, or the like, that may be coupled to a rotary encoder, or other rotary transducer, for providing a control signal based upon, at least in part, movement of the wheel, ring, knob, or the like. In some embodiments, the user may specify/indicate as a preference the count-up and/or count-down speed for one or more of the input devices as well as the entry command for a speed change, e.g., the switch device must be depressed for 3 seconds before the count-up/count-down speed changes to 4 values second. However, in various embodiments, each input device may include a separate entry for user preference and/or in some embodiments, the user may indicate a preference and apply the same preference to all input devices. In some embodiments, the count-up/count-down speed may be a preprogrammed rate until and unless the user changes the speed.

Remote control assembly 300 may include the ability to pre-program basal rates, bolus alarms, delivery limitations, and allow the user to view history and to establish user preferences. Remote control assembly 300 may also include a glucose strip reader 312.

During use, remote control assembly 300 may provide instructions to the infusion pump assembly via a wireless communication channel established between remote control assembly 300 and the infusion pump assembly. Accordingly, the user may use remote control assembly 300 to program/configure the infusion pump assembly. Some or all of the communication between remote control assembly 300 and the infusion pump assembly may be encrypted to provide an enhanced level of security. As discussed above, in some embodiments, the remote control assembly 300 additionally receives signals from at least one continuous glucose monitor.

Figure 6:
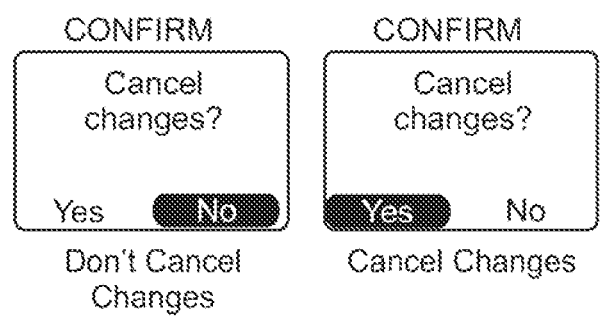
FIG. 6 shows an exemplary embodiment of the Cancel Changes Confirmation Screen.

In the exemplary embodiments of the user interface, the user interface requires user confirmation and user input. The exemplary embodiments of the user interface are centered on ensuring the user knows the effect of various interactions on the pump. Many examples will be presented throughout this description of the pump communicating the result of the user's actions to the user. These features ensure the user understands their actions and therefore, imparts greater safety onto the user. One such example is throughout the exemplary embodiment of the user interface, where the user presses the back button on a screen after a value has been changed, the user interface displays the Cancel Changes confirmation screen, as shown in FIG. 6. If the user selects "Yes", the user interface discards any pending changes, closes the confirmation screen and goes back to the previous screen (i.e., the screen previous to the screen where the user pressed the Back button). When the action selection is "No", on the "Cancel Changes?" confirmation screen, the user presses the enter button or other depending on the embodiment, and the user interface closes the confirmation screen and returns to the screen with pending changes.

This feature prevents the outcome where the user assumes the changes have been implemented, but in fact, they have not been. Thus, this feature prevents that circumstance and ensures the user understands that the changes have not been implemented.

Power Up

Generally, an infusion pump is used for therapy by a user almost continuously, with some exceptions. Thus, from the time an infusion pump is "powered up", i.e., a battery is inserted into the pump and the pump is "Setup" for use for therapy, the infusion pump remains on and in many cases, connected to the user by way of a cannula. Oftentimes, a user will "disconnect", i.e., disrupt the fluid connection of the tubing to the cannula, for short and predicted periods of time. For example, users often disconnect while changing the cannula, changing the infusion set, changing the reservoir, priming the tubing, bathing/showering, undergoing tests such as an MRI, or otherwise being exposed to harmful forces, for example, electromagnetic forces, or, in some circumstances, while exercising or being exposed to potentially corrosive water, for example, salt water. There are many additional circumstances where users may disconnect. However, generally, these disconnection events are planned and the user understands they will not receive therapy from the infusion pump while disconnected from the pump.

Thus, once infusion pump therapy has begun with a given pump, the user will remain connected and will likely receive their therapy from the infusion pump until and unless the infusion pump is replaced by another form of therapy, for example, another pump or multiple daily injections.

The power up user interface is visible when a battery is inserted into the infusion pump. If the infusion pump has been in use by the user prior to the battery change, then the pump will initialize. If the pump had not been previously used by the user (i.e., the pump is new to the user), on first use of the pump, the user interface automatically guides the user through programmable settings that must be initialized before insulin delivery or other fluid therapeutic delivery may occur.

Figure 5A:
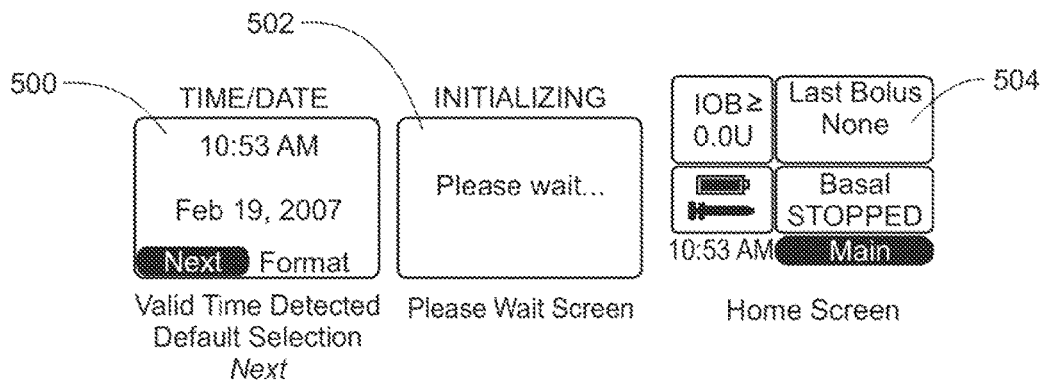
FIGS. 5A-5C shows exemplary embodiments of select Time and Date Wizard screens according to one embodiment.

Referring now to FIG. 5A, after the initialization period, the user interface advances to Time and Date Wizard, which takes the user through the TIME/DATE, SET TIME and SET DATE screens, and then advances to the Home screen (as also discussed with respect to FIGS. 10A-10E). As shown in FIG. 5A, if a valid time is detected, the default selection for the user is "next" on the TIME/DATE screen 500, wherein the user interface proceeds to an initializing screen 502 then to the Home Screen 504.

Figure 5B:
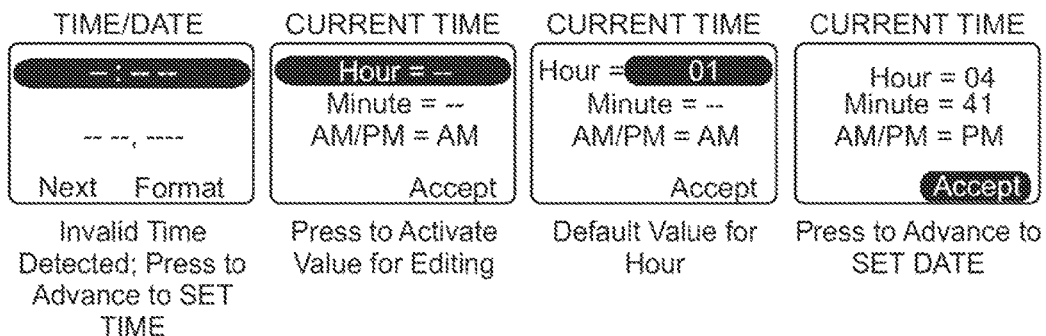
Figure 5C:
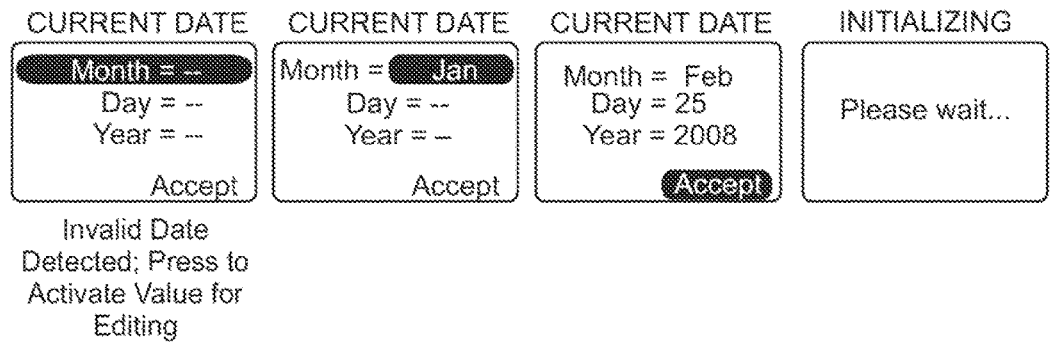

However, referring now to FIGS. 5B-5C, if the system does not detect a valid time and date, the Time and Date Wizard shall display the TIME/DATE screen with the Time values set to dashes (--) to indicate that no values are currently set. The Date value is not displayed until a valid time has been set.

Amongst other advantages, where the system detects a valid TIME/DATE, the Time and Date Wizard automatically fills the TIME/DATE with the detected valid TIME/DATE. However, the system still ensures that the user reviews the detected TIME/DATE and presents an opportunity for the user to change the TIME/DATE if the TIME/DATE on the screen is incorrect. In fact, in the exemplary embodiment shown, the system will not complete initializing and will not advance to the Home Screen until the user has selected "next", i.e., affirming the TIME/DATE is acceptable.

Conversely, where an invalid date is detected, the system does not automatically fill the TIME/DATE but rather requires the user to do so. Thus, the user interface system, in the exemplary embodiment, requires the user to always review the TIME/DATE.

Some embodiments of the user interface include a Trainer Mode. This mode is generally used when a user or caregiver is initially using the pump and thus may take additional time to review and enter information into the user interface. The Trainer Mode allows for the user to select a duration that the user interface will disable timeouts. In normal mode, the user interface otherwise includes timeouts as a power conservation measure, where the screen will timeout at a preset interval of user inactivity. However, in this embodiment, the timeouts are disabled. In the exemplary embodiment, when the Trainer Mode is initialized, a "duration" is set by the user or caregiver, for example, 2 hours, and during this duration, timeouts are disabled.

User Setup

User Setup includes many features to the user and those used by the pump for therapy. These include but are not limited to setting the: pairing with a companion, time, date, time/date format, time format, glucose units (mg/dl vs. mmol/L), language, blood glucose targets by time of day, basal rate by time of day or preprogrammed title, insulin type, duration of action of insulin, cursor preference, magnify preference, bolus button, bolus and basal limits, "1 U Drop" (one unit drop), display/button side, carbohydrate to insulin ratio, alarm features including alarm types where options exist, sensitivity to occlusion, inactivity alarm, therapy lockouts, care comments and reminders.

As discussed above, in the exemplary embodiments, the infusion pump system includes a controller or companion device, for example, similar to one described above. In these embodiments, at Power Up, if the pump is not currently paired and not fully initialized the user is first prompted to pair the pump with a remote control device, i.e., a controller or Companion, as discussed above. The user may choose to skip this option, for example, where the user does not desire to pair with a companion device. In this case, the user interface advances the user to other Setup screens.

Figure 7A:
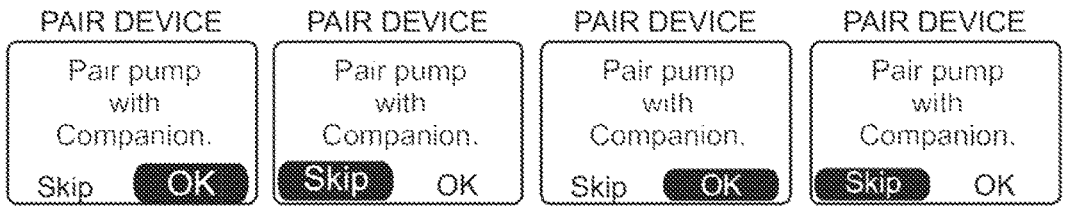
FIGS. 7A-7F shows an exemplary embodiment of at least a selection of the pair device screens.

Referring to FIG. 7A, if the user chooses to initiate the pairing (by selecting OK); the user interface displays the PUMP Searching for Companions screen (it should be noted that where the pump is an embodiment that does not include a display, the Companion will be the only screens during the pairing process. Thus, similar screens will appear on the Companion only). The remote Companion must be in pairing mode for the pairing to be completed. Thus, for pairing an infusion pump with a Companion, both devices must be in pairing mode. This feature serves as one of many safety features during the pairing process. Requiring both devices to be in pairing mode ensures an infusion pump is not "hijacked" by a non-intended Companion. If the pairing fails or is cancelled, when the user selects OK on the Pairing Failed or Pairing Cancelled warning screen, the user interface displaces the STEP 1 screen on the Setup Wizard and sets the Radio setting to "Off". Thus, where the system is not paired, the pump user interface automatically turns the radio off and proceeds to continue Setup Wizard.

Figure 7B:
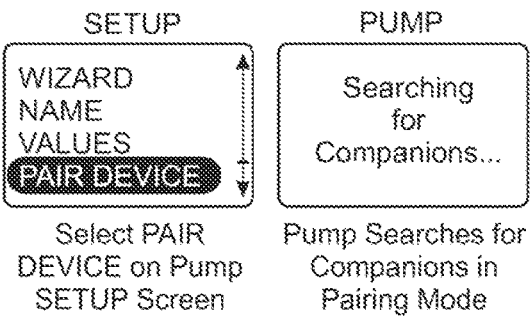

Referring now to FIG. 7B, to pair a pump and Companion device for remote communications, the pairing process requires user interaction on both the pump and Companion. In the exemplary embodiment, the user interface displays the PUMP "Searching for Companions" screen on the pump when the user selects and accepts the "PAIR DEVICE" item on the "SETUP" screen. The user selects the "PAIR DEVICE" item to initiate the pairing process with and begin searching for a remote control Companion device in pairing mode. On the Companion, the user selects "PAIR PUMP" on the "SETUP" screen, then selects the "Yes" action selection on the "Is pump ready?" confirmation screen. Before selecting "Yes", the user needs to start the search on the pump. Thus, in pairing mode, both the infusion pump and the Companion must be in pairing mode, simultaneously, for the pairing mode to commence.

When the user selects the "PAIR DEVICE" item on the pump "SETUP" screen and presses the enter button, the user interface: 1) turns on the radio if it is turned off; 2) initiates a search for Companion devices that are in pairing mode (where pairing has been initiated on the Companion); and 3) displays the "Searching for Companions" pairing screen.

Figure 7C:
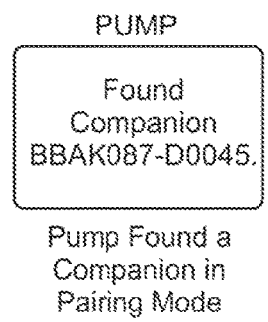

Referring now to FIG. 7C, the user interface displays the PUMP "Found Companion "{Companion Serial #}" screen on the pump following the PUMP "Searching for Companions" screen, when a Companion in pairing mode has been found. The serial number of the Companion is displayed on the screen in place of the "{Companion Serial #}". This screen indicates a Companion in pairing mode has been found, but the pairing has not been completed. The user must confirm the pairing on the Companion device for the pairing process to be complete. This feature ensures the user has an opportunity to confirm that the pump found is indeed the pump in which the user intends to pair with the Companion device.

Figure 7D:

The user interface displays "No Companions Found" warning screen on the pump when the user initiated pairing, and the search for Companions in pairing mode failed after searching for approximately 1 minute. In other embodiments, the amount of searching time may vary. The pump user interface, in the exemplary embodiment, turns off the radio and warns the user when no Companions were found after searching for Companions for a defined time period without button press interruptions (See FIG. 7D). This ensures that where pairing mode has commenced on one side, for example, on the Companion but not the pump, a timeout period will end the pairing mode.

Figure 7E:
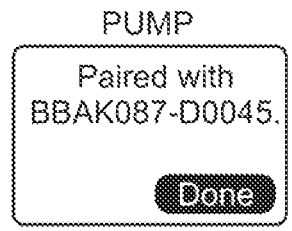

Referring to FIG. 7E, the user interface displays the PUMP "Paired with{Companion Serial #}" screen on the pump when the pairing has been confirmed on the Companion device. In the exemplary embodiment, the user interface displays an indication to the user of the Companion device serial number to which a pump is paired when a pump and. Companion have been successfully paired. This feature allows the user opportunity to confirm the Companion serial number indicates the intended Companion is paired with the pump.

Once the "Done" is selected, where the pump is fully initialized, the pump will proceed to the Home screen. Where the pump is not fully initialized, the user interface will display the Setup Wizard Step 1 screen.

Although the above embodiments are described with reference to the PUMP screens, similar screens are displayed on the Companion throughout the pairing process.

During pairing, the user interface displays the "Pairing cancelled" warning screen on either the pump or the Companion device, when the user presses a button on the pump while displaying the PUMP "Searching for Companion" screen, or on the Companion while displaying the COMPANION "Searching for Pumps" screen. If the pump or Companion were paired before attempting to pair them again, and the user cancelled the pairing, the existing pairing is not lost.

Figure 7F:

Pairing may be cancelled where the user presses a button on the pump or the Companion while the "Searching for . . ." screen is displayed. Referring now to FIG. 7F, the user interface displays an indication to the user that the pairing process was cancelled before the pump and Companion were successfully pairing. Thus, the user will be aware that the pump and Companion may not be paired (in the exemplary embodiment, if the pump and Companion were paired, a screen or audio signal will indicate same).

In the exemplary embodiment, the user interface displays the "Incompatible pump found. Pairing failed" WARNING screen on the Companion during the pairing process, when a pump in pairing mode is found that has a serial number that indicates different glucose units than the units configured on the Companion (i.e., mg/dL vs. mmol/L). As a safety feature, the user interface considers a pump and Companion with different glucose units incompatible and disallows pairing the two devices. When the user attempts to pair the pump and Companion with different glucose units, any previous pairing is lost.

Either after pairing is completed or once pairing has been skipped, the user completes the "Setup Wizard", setting various features of the user interface.

As discussed above with respect to FIGS. 5B-5C, because the infusion pump delivers insulin (or another fluid) based on time of day (in the exemplary embodiment, however, in other embodiments, the pump may deliver based on another criteria, for example, every "2 hours", or "once daily"), it is important that the time settings are accurate. Also, in the exemplary embodiment, the pump device logs a history of insulin (or other fluid) delivery. Therefore, it is important that the date settings are accurate. When the user first initializes the pump, or when the system does not detect a valid time, the Current Time settings have no default values, and the user interface requires the user to set the current time. Additionally, when the user changes the battery in the pump, the user interface requires the user to review the settings for the current time to ensure that they are accurate.

After the user has set a valid time, the time is continuously updated by the device's real-time clock. After the device has fully initialized, the user may change the current time by entering either the Setup Wizard or the Time and Date Wizard through the SETUP screen.

If the user changes the time and/or date on the pump and then accesses the user interface on the Companion device, the time and date on the Companion is synchronized with the pump's time and date, and a warning screen is displayed on the Companion to indicate the time on the Companion has been changed to the pump time.

When the user first initializes the pump, or when the system does not detect a valid date, the Current Date settings have no default values, and the user interface requires the user to set the current date. Additionally, when the user changes the battery in the pump, the user interface requires the user to review the settings for the current date to ensure that they are accurate.

After the user has set a legal date value, the date is maintained and updated by the pump's real-time clock. If the user enters a non-legal date, then the pump will indicate same with an audio and/or visual indication that the date is not accepted. After the device has fully initialized, the user may change the current date by entering either the Setup Wizard or the Time and Date Wizard through the SETUP screen.

The user interface includes a preprogrammed list of "legal dates". These may be based on the Gregorian calendar, or within any other pre-definable parameters. These may include, for example, but not limited to, the number of days for particular months, the years in which a date of February 29 is a legal date. In the exemplary embodiment, the user interface may only allow these parameters to be changed at a system level, i.e., not by the user. However, in other embodiments, the user interface may allow the user to change the parameters.

In the exemplary embodiment of the pump, as discussed above, the pump is an insulin pump. The insulin concentration value (Units/mL) is preprogrammed to be "U100" and cannot be changed by the user. This is a safety measure, as generally, a user on insulin therapy uses U100 insulin. However, in various embodiments where either a different insulin therapy is contemplated, or, if a different fluid is infused, this feature may require user input to specify the concentration of the fluid.

Related settings that the user may specify include the insulin type and action time. The user interface uses these settings to determine the amount of Insulin on Board or "IOB". IOB refers to a number which serves as a gauge to the "action" of the insulin currently in the user. The gauge is comparing the action available to a quantitative "amount of insulin" currently in the user. Thus, as the Action Time and Insulin Type are used to calculate IOB, which is used, as described later, in bolus calculations, it is critical this information be entered.

Figure 8A:
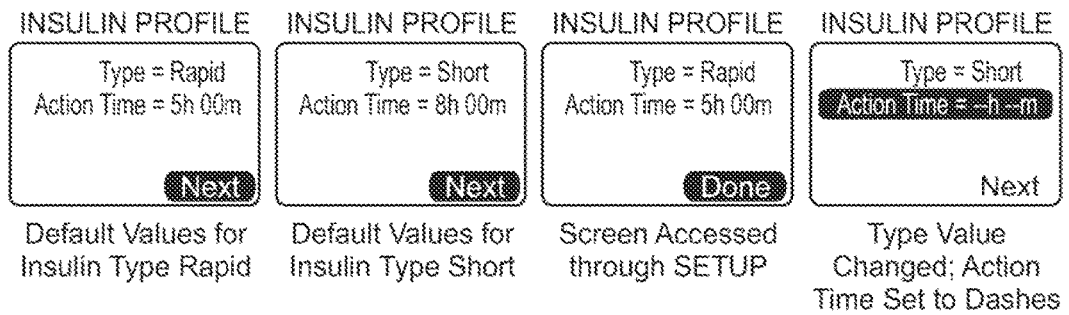
FIGS. 8A-8B shows an exemplary embodiment of at least a selection of the insulin profile screens.

When the pump is fully initialized, the user may change the insulin settings by entering the Setup Wizard through the SETUP screen, or by selecting INSULIN on the SETUP screen. Referring to FIG. 8A, the exemplary embodiment of these screens are shown.

Figure 8B:
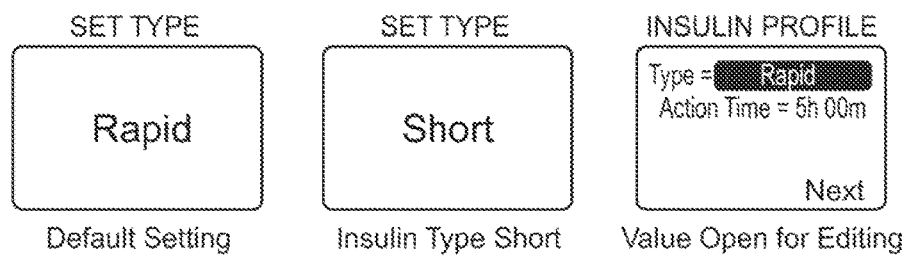

Referring now to FIG. 8B, the user interface opens the SET TYPE edit item screen when the user accepts the Type item on the Insulin Profile select item for edit screen, and Magnify is set to On. "Magnify" refers to an option in the exemplary embodiment of the'user interface, where the user may prefer that the text in the curser and in various screens, be "magnified" so as to be better visible. Various embodiments of this feature may be used in the user interface, including those described in pending U.S. Publication No. US-2008-0177900, published Jul. 24, 2008 and entitled Medical Device Including a Slider Assembly, which is herein incorporated by reference in its entirety.

When Magnify is "Off", or when the user accesses the screen on the Companion device, the user interface opens the Type item for editing. The Type value identifies the type of insulin being used. Two options are available in the exemplary embodiment, either Rapid or Short. In various other embodiments, additional options may be pre-programmable and selectable options.

The exemplary embodiment of the user interface includes various safety features related to the INSULIN PROFILE screens. For example, when the Type item on the INSULIN PROFILE screen is open for editing and the user presses a soft-key button for "Next" or "Done" action selection, the user interface will either: 1) accept and close the selected value; or if the user changed the Type value, the user interface will change the Action Time value to dashes and display a warning message in language dependant text: "Dashed items must be set". This is to prompt the user that an Action Value must be entered; or, 3) if the user did not change the Type value, select the action selection, save any pending changes and advance to the next screen.

Figure 9A:
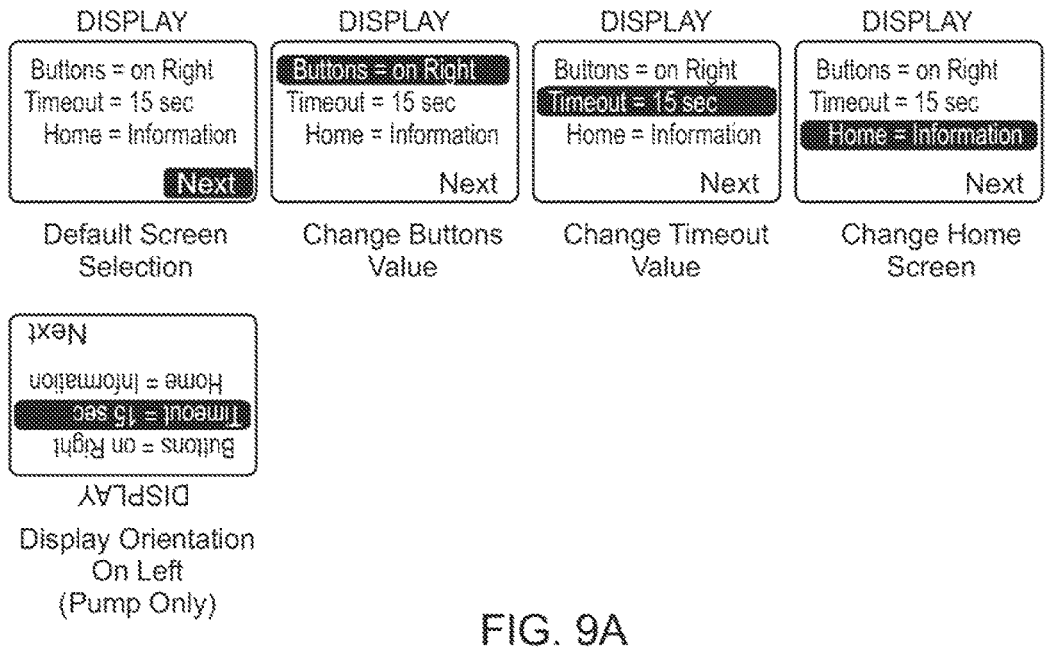
FIGS. 9A-9B shows an exemplary embodiment of at least a selection of the display screens.
Figure 9B:
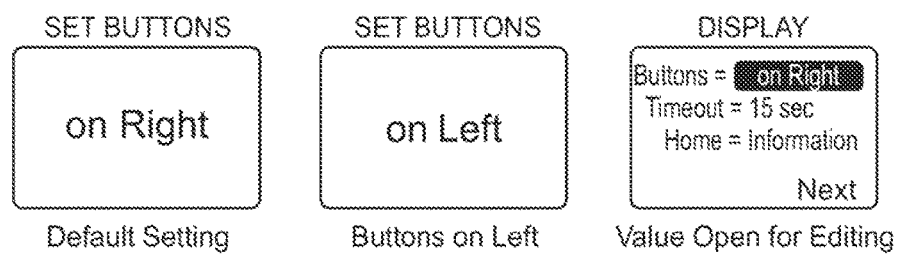
Figure 10A:
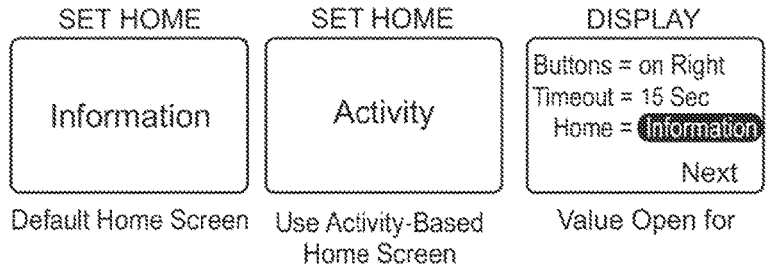
FIGS. 10A-10E shows an exemplary embodiment of at least a selection of the home screens.
Figure 10B:
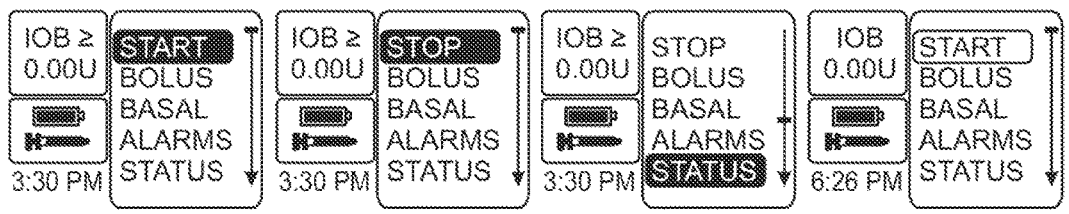
Figure 10C:
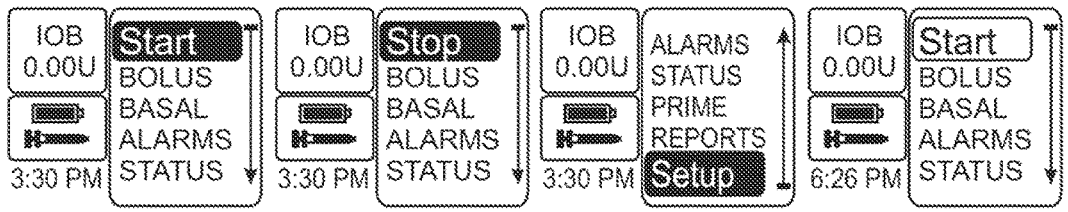
Figure 10D:
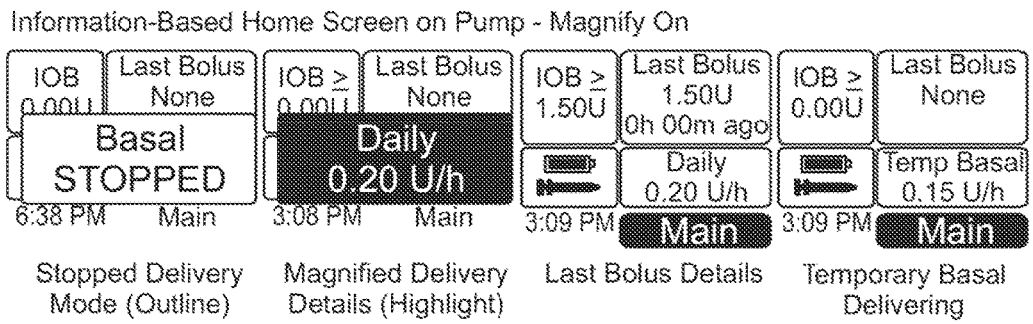
Figure 10E:
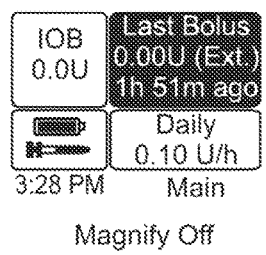

Referring to FIGS. 9A-9B, in the exemplary embodiment of the user interface, the user may configure display settings for the pump to have the user interface screens oriented such that the enter and back buttons, for example, are either on the right side of the LCD display, or the left side. Additionally, the device uses screen timeouts to conserve energy by turning off the display and entering into a low-power sleep state when the user has stopped interacting with the device within a period of time. The user configures this timeout value as part of the display settings. Screen timeouts are not in effect until after the pump is fully initialized.

Another display setting that the user may configure is the whether to display an activity-based home screen or an information-based home screen. The Home screen is further described below with reference to FIGS. 10A-10E. In the exemplary embodiment, the user interface allows the user to access the display settings for the pump through the Setup Wizard STEP 2 screen, by advancing the DISPLAY screen. The display settings that also apply to the Companion are accessible on the Companion by selecting REFERENCES on the SETUP screen.

Referring to FIG. 9A, the user interface allows the user to set a duration value for the timeout feature of the display. Additionally, the user may select the home screen feature using the DISPLAY screens.

Referring now to FIG. 9B, the user interface includes a feature which allows the user to configure the display orientation of the user interface screen on the pump as it relates to the position of the buttons (i.e., referring to FIG. 1A, the switch assemblies 108). For example, the user interface allows the user to designate whether the buttons are on the left of the display, or the right. In the exemplary embodiment, the user interface may have a default setting, for example, buttons on right or buttons on left.

Referring now to FIG. 9A, the user interface opens the SET BUTTONS edit item screen when the user accepts the Buttons item on the DISPLAY select item for edit screen, and the user-programmable settings for Magnify is set to "On". When Magnify is "Off", or when the user accesses the screen on the Companion device, in the exemplary embodiment, the user interface opens the Buttons item for editing. The user accept the Buttons item to configure the device to orient the user interface screens such that the buttons are either on the right of the LCD display, or on the left. An exemplary embodiment of the BUTTON screens are shown in FIG. 9B.

The ability of the user to set the side of the buttons allows the user to customize the pump to their preferred hand. Thus, this is an advantage for ease of use to the user. Additionally, in some embodiments of the infusion pump, as shown in FIGS. 1A-1F, where a slider 106 may be used as input device, the ability of the user to set the user interface such that they are free to use their preferred hand in all inputs is an advantage and may allow the user to be more efficient and safe in the handling of inputs to the pump.

In the exemplary embodiment, the user interface includes a bolus calculator. The user must provide particular input information regarding their therapy into the user interface while using the bolus calculator option. However, in some cases, the user may choose to enter this information in advance through Setup screens. The information entered in advance may then be used in any calculators requiring this information. However, the information may be entered at the time of the use of the calculator.

The information used by the calculator is typically based on a user's medical team's recommendation. The bolus calculator requires this information. In addition to the INSULIN screens discussed above, the user may also enter information regarding "1 U DROP", carbohydrate ratios and Blood Glucose targets.

Figures 11A, 11B:
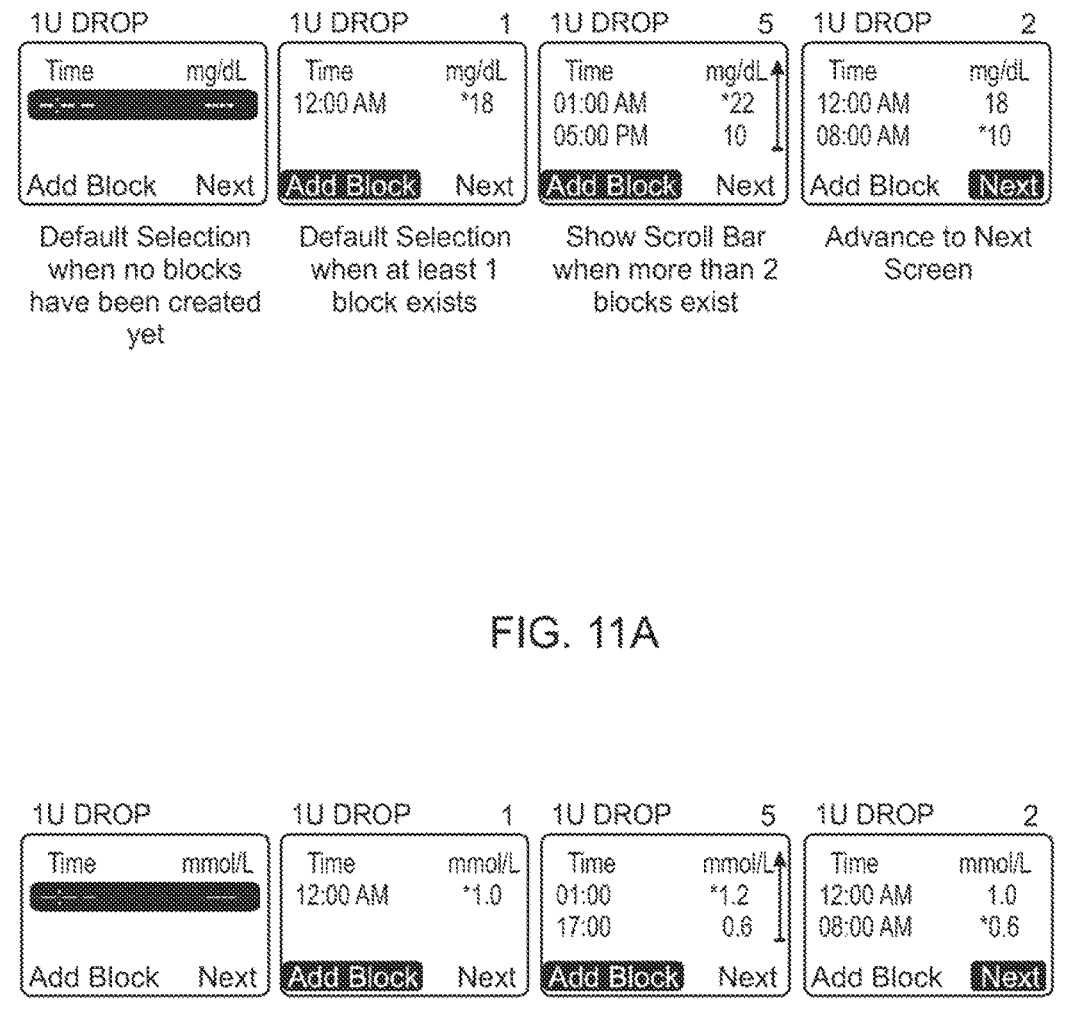

Referring now to FIGS. 11A-11B, various 1 U DROP screens are shown according to an exemplary embodiment. In the exemplary embodiment, the user may set from 1 to 24 1 U DROP values based on the time of day. In addition, the user may set from 1 to 24 insulin to carbohydrate ratios (i.e., I:CHO) based on the time of day. However, in various other embodiments, the user may set more than 24 1 U DROP values (and/or I:CHO values), and may also specify the day of the month or the day of the week, amongst many additional factors that may be specified. The 1 U DROP values are known insulin sensitivity values (i.e., how much insulin causes how much change) for the user. The I:CHO value defines the default ratio of carbohydrate grams to 1 Unit of insulin for a specified time period. The 1 U DROP value is used to calculate how much insulin the pump may recommend the user deliver to bring the user's blood glucose value to a desired level. The 1 U DROP values may be programmed on the hour. In some instances, the 1 U DROP value may not have been previously set by the user. In these cases, while using the bolus calculator option, the user may specify the 1 U DROP value when programming a correction bolus.

In the exemplary embodiment, and as may be seen in FIGS. 11A-11B, the user interface may allow the user to program 1 to 24 correction factor values, based on the time of day, that estimates how much change to a user's blood glucose level is effected by 1 unit of insulin.

The I:CHO value may be used in bolus calculations where the user enters an amount of carbohydrates and the bolus calculator suggests an insulin dosage. Further, the I:CHO may be used during a correction and food bolus calculation.

In the exemplary embodiment of the user interface, the user interface allows the user to define the Increment of insulin Units that will be used for each click of the slider when delivering either a normal bolus or an extended bolus through the user interface bolus screens. Additionally, in the exemplary embodiment, the user interface allows the user to define the Increment of insulin Units that will be used for each click of the slider when setting or editing a Rate value for a Basal program. In various embodiments, in addition to the slider, the Increment may be used to define the Increment of insulin Units used for each press of a button or each step movement of a jog wheel, for example. However, the Increment function may be used in various embodiments to apply to any input device or assembly desired.

The Increment item allows the user to customize the user interface for their general therapy needs. For example, the user interface may allow the user to select an increment of "0.10 U", "0.05 U", or "1.00 U" for example. Thus, a user having a therapy that typically includes bolus or basal program amounts of "0.30 U" may select the "0.10 U" Increment, whereas a user having a therapy that typically includes bolus or basal program amounts of "10.0 U" may select the "1.00 U" Increment. Thus, this allows for more efficient use by the user in delivering their therapy.

The user interface includes an option for SET TEMP, i.e., setting a temporary basal. In the exemplary embodiment, the SET TEMP option includes the option of the user setting or configuring the temporary basal amount in terms of delivery rate (i.e., Units/hour), or in terms of a percentage of the active basal program rate. Thus, in the exemplary embodiment a user may define the temporary basal rate or may request a temporary basal reduction, based on the current basal program.

Figure 12:
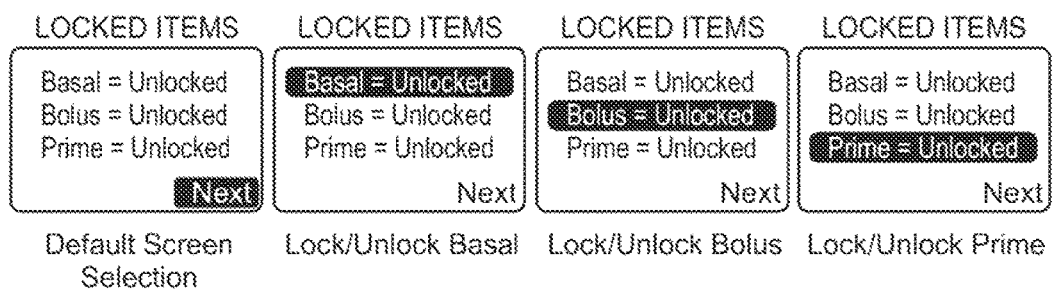
FIG. 12 shows an exemplary embodiment of at least a selection of LOCKED ITEMS screens.

Referring now to FIG. 12, the user interface additionally includes, in the exemplary embodiment, a LOCKED ITEMS settings feature which allows the user to lock or unlock certain features of the device to restrict access to those features. These features include, but may not be limited to:
1) the basal menu features that allow the user to activate an existing basal program, start temporary bases, edit, delete or rename an existing basal program;
2) the bolus features that allow the user to deliver one-button, normal, extended, and dual boluses;
3) the prime feature allowing the user to prime the pump.

Thus, in the exemplary embodiment, the user interface allows flexibility by allowing the user to lockout features separately, rather than either locking the whole pump, or unlocking the whole pump. This feature may be advantageous with respect to child users or other users that may not be capable of making therapy decision, but may, when necessary, need access to priming or basal changes.

Figure 13A:
FIGS. 13A-13B shows an exemplary embodiment of at least a selection of WARNING screens.

In the exemplary embodiment, the user interface includes various features that inform the user when various screens are exited or information is missing. These features ensure the user knows the impact of their actions. For example, referring now to FIG. 13A, in the exemplary embodiment, when initializing the device settings, the user must set values for any default settings that have no initial value, i.e., in the exemplary embodiment, those settings displayed as dashes, before advancing to the next screen. The user interface displays the Warning screen "Dashed items must be set" when the user fails to complete these settings. In particular, in the exemplary embodiment, this Warning screen will appear where the user:

1) when initializing device setting values through the Setup Wizard and the user presses the back button the STEP 1 screen;
2) when programming a temporary basal or a bolus, when any items are set to dashes on the screen and the user accepts the "Activate" or "Deliver" action selection;
3) when initializing device setting values in the Setup Wizard for the following when the user accepts the "Next", "Accept" or "Done" action selection:
   The TIME/DATE screen when either a time or date has not been set.
   The CURRENT TIME screen when all fields of the time value have hot been set.
   The CURRENT DATE screen when all fields of the date value have not been set.
   The INSULIN PROFILE screen when a value has not been set for the Time item.
   The CARB RATIOS BLOCK n screen when a value has not been set for one or more items.
   The 1 U DROP BLOCK n screen when a value has not been set for one or more items.
   The BG TARGET BLOCK n screen when a value has not been set for one or more items.
   The DAILY basal program BLOCK n screen when a value has not been set for one or more items.

Figure 13B:

Referring now to FIG. 13B, while the device is in a delivery mode, the user interface, in the exemplary embodiment, prevents the user from changing certain settings. For example, when the user selects and accepts the BASAL LIMITS or WIZARD item on the SETUP screen, if the basal is currently running, the user interface displays the warning "Stop delivery before using this function". Additionally, when the user selects either the Time or the Date values on the TIME/DATE screen when basal delivery is in progress, the user interface will display this Warning. This is a safety feature in the exemplary embodiment of the user interface. Where a user change or edit may cause confusion during delivery, for example, a rate change of a basal profile while that basal profile is delivering, or changing the TIME/DATE while in delivery, the user interface may use the Warning screen shown in FIG. 13B. In the exemplary embodiments, additional features may not be changed during delivery. These include but are not limited to lockout features.

Figure 14A:
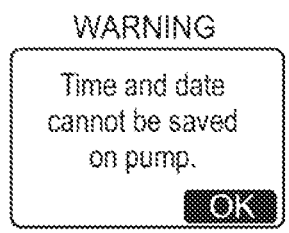
FIGS. 14A-14B shows an exemplary embodiment of at least a selection of Companion WARNING screens.

Referring now to FIG. 14A, in embodiments where a pump and Companion are paired, there are various changes that, made on the Companion, may not be accepted by the pump. For example, when the user sets the time and date through the Companion-specific time/date screen, if the Companion is paired with the pump and the pump is delivering basal, in the exemplary embodiment, the pump cannot accept a new time, and the Companion displays the warning "Time and date cannot be saved on pump". Once the pump and Companion are communicating, upon background synchronization, the pump time will be sent to the Companion, and the Companion will display the warning "Companion time changed to pump time". This warning screen may be used in many different like scenarios to inform the user both that their requested changes have not been made, and when the change has been made. Thus, the user is informed of the outcome of their actions and thus is regularly aware of the impact on the pump.

Figure 14B:
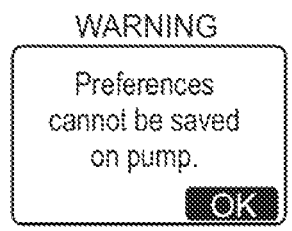

Referring now to FIG. 14B, in the exemplary embodiment, the user interface may display a warning on the Companion when the user exits the Companion PREFERENCES screen, and the pump is either busy or communication with the pump is down. Thus, the user is aware that their preferences have not been saved onto the pump, and thus, know that they should re-enter those preferences at a time when communications are restored.

Figure 15:
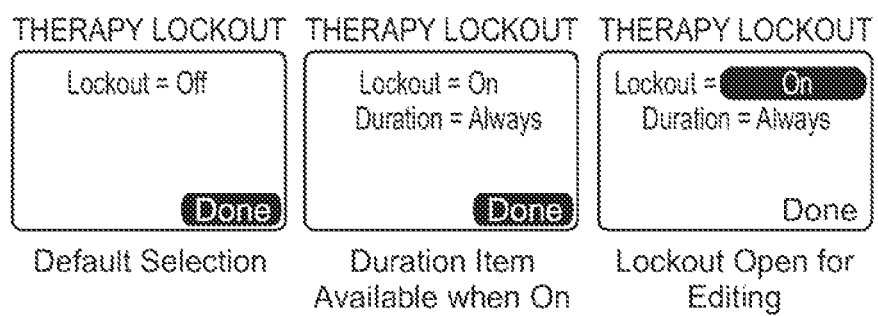
FIG. 15 shows an exemplary embodiment of at least a selection of Companion Temporary Lockout.

Referring now to FIG. 15, in the exemplary embodiment, the Companion may be configured to enable a temporary lockout from certain functions, for example, functions that affect starting and stopping delivery on the pump. However, additional functions may also be locked out temporarily in some embodiments. The THERAPY LOCKOUT settings screen, shown in FIG. 15, allows the user to turn the lockout on, and to specify a duration for the lockout to be in effect. If the user chooses a duration of "Once", the lockout is in effect until the user selects Unlock on the THERAPY LOCKOUT Unlock screen.

Figure 16:
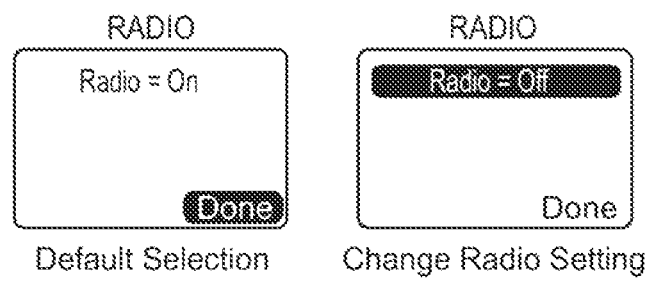
FIG. 16 shows an exemplary embodiment of at least a selection of Radio screens.

Referring now to FIG. 16, the user interface allows a user to turn the radio off when the pump is paired with a Companion. Changing the setting on the pump turns off the radio only on the pump; similarly, changing the setting on the Companion turns off the radio only on the Companion. This feature allows a user to turn the radio off in cases where radio communication when desired, for example, when radio communication between devices is not advisable, allowed or safe.

Home Screen

Referring now to FIGS. 10A-10E, in the exemplary embodiment, the user interface opens the SET HOME edit item screen when the user accepts the Home item on the DISPLAY select item for edit screen, and the user-programmable setting for Magnify is set to "On". When Magnify is "Off", or when the user accesses the screen on the Companion device, the user interface opens the Home item for editing. The user accepts the Home item to specify the content of the Home screen as either information-based or activity-based.

The Home screen provides access to device features and displays information about the status of the pump and the delivery. The Home screen may be configured to display an activity-based menu (i.e., Activity-Based home screen), or to display information about the current delivery status and last bolus information (i.e., Information-Based Home screen). The Home screen is configured through the PREFERENCES option on the SETUP screen.

Still referring to FIGS. 10A-10E, in the exemplary embodiment, for both the Information-Based and Activity-Based Home screens, the user interface displays the current time as maintained by the device's real-time clock, icons that provide an indication of the remaining battery capacity and insulin volume (or reservoir volume), and the amount of IOB. In some instances, a greater-than or equal to symbol may be displayed next to the IOB label. Specifically, if the bolus log contains a corrupt record, or if the time has been lost and needs to be set at powerup, the bolus log is reinitialized. However, simply replacing the battery does not erase the bolus log when there is a valid time and date at powerup. Thus, the IOB is not lost due to a battery being replaced and in the exemplary embodiment, on the Activity-Based Home screen is indicated to the user each instance the pump display is shown. This feature in the exemplary embodiment imparts to the user clearly and efficiently the amount of IOB such that the user may use this information in their therapy. Additionally, as the IOB is not lost when the battery is replaced, the user may rely on bolus calculators and other indications on the display by the user interface, for their therapy, without interruption. However, in some embodiments, the IOB may timeout in certain situations, for example, where the pump determines that power was lost for more than a threshold time or if the pump is unable to determine the date and time, or the amount of time in which the pump did not have power. Thus, a correct or true determination of the IOB may not be possible in these circumstances. However, in the exemplary embodiment of the infusion pump, the safety processor maintains the date and time of the devices. Thus, IOB recovery is possible because of the internal clock.

Additionally, in the exemplary embodiment, the IOB may also be recovered after a reservoir change.

Still referring to FIGS. 10A-10E, in the exemplary embodiment, when the magnify setting is "Off" on the pump, the cursor type on the Information-based Home screen always is displayed as Highlight regardless of the Cursor setting. This allows for the screen selection to always be distinguishable.

In the exemplary embodiment, when delivering an extended bolus, the bolus section of the Information-Based Home screen displays the details of the running extended bolus, including the amount that has been delivered, the full programmed amount, and how much time has elapsed since the start of the extended bolus. If an extended bolus is stopped before any of the extended bolus insulin has been delivered, the Last Bolus information on the Home screen may be updated to reflect the previous bolus that delivered greater than 0.0 U. However, in the exemplary embodiment, where the user power cycles the pump (i.e., the power supply is removed and replaced, this may occur when the user is changing the battery, i.e., removing the first power supply and replacing the first power supply with a second power supply, or removing the first power supply and replacing it back into the pump), and an extended bolus that was stopped before any insulin was delivered is the last bolus in the history, the Last Bolus details on the Home screen reflect that extended bolus.

Additionally, in the exemplary embodiment, the user interface displays the last bolus details on the Information-Based Home screen as follows:
1) The last non-zero bolus is displayed in the history if that bolus occurred after the most recent power cycle. If there are no boluses in the history other than a zero extended bolus, the user interface with display "None".
2) The most recent bolus in the history is displayed which may be an extended bolus of 0.0 U, if a power cycle occurred more recently than the last bolus.
3) If there are no boluses in the history, the user interface displays "None".

Thus, in the exemplary embodiment, the user interface proves quick access to starting and stopping basal delivery, starting a temporary basal, and switching basla programs on the Information-Based Home Screen. Additionally, using the Information-Based Home screen, the user the user interface provides quick access to bolus features (when in delivery mode). Also, the user interface displays may display a greater-than or equal to symbol to the right of the IOB label on the Home screen when any of the following are true:
1) The Bolus date for the entire action time period is not available;
2) More than a predefined number, e.g., 10, boluses were given within the action time;
3) There is no bolus history, and less time than the duration specified by the user-programmable action time has passed since the bolus log was initialized;
4) The IOB amount is great than a predefined number, e.g., 300.

Thus, in the exemplary embodiment, the user interface provides information regarding IOB where that information is safe to provide within a predetermined threshold. That is, the user interface ensures the user has access only to information on which may be correct and safe for the user to base therapy decisions.

Alert and Recoverable Alarm Notification

For purposes of the current description and in the exemplary embodiments described herein, notifications include alarms, alerts and reminders. Alarms are either recoverable or non-recoverable. Alerts, reminders and recoverable alarms notify the user of conditions that may affect normal operation of the pump that the user may need to address. For alerts, the user generally has some period of time in which to address the condition; whereas recoverable alarms stop delivery and should be addressed as soon as possible.

Non-recoverable alarms may also be referred to herein as system alarms. For recoverable alarms, the user may physically correct the problem (i.e., change the battery, replace the reservoir, etc.), and through the features of the user interface, the pump may resume delivery. System alarms are no recoverable via the user interface. System alarms stop all processes, including delivery, and render the user interface unusable.

When the user interface is displaying a screen other than the Home screen, or when a normal bolus or device prime is in progress, in the exemplary embodiments, alert and alarm notifications generated on the pump are suspended. If a normal bolus or device prime is in progress, the user interface presents the notification after the prime or normal bolus completes or is stopped, either by the user, or in the case of a recoverable alarm, the alarm condition itself stops delivery. If the user interface is displaying a screen other than the Home screen, the notification is suspended until the user interface transitions to the Home screen. When a recoverable alarm that stops delivery is suspended, the user interface suspends just the notification; the delivery is stopped as soon as the alarm condition is detected.

In the exemplary embodiment, when more than one notification is pending, the notifications are presented in order of priority. Also, in the exemplary embodiment, where a Companion is used with an infusion pump, all of the alerts, alarms, and reminder screen described herein are generated on the pump. If an alert or recoverable alarm condition occurs when the user interface is displaying the Home screen, the user interface produces the attention sequence on the pump and displays a notification screen that described the condition. If the pump is asleep, it wakes up to display the notification. If the pump is not fully configured, notifications are suspended on the pump and are not sent to the Companion. When the Companion is awake and displaying the Home screen, if there is a notification being displayed on the pump, the notification also is displayed on the Companion. The user may silence the notification on either the pump or the Companion.

In the exemplary embodiment, when the Companion is displaying a screen other than the Home screen and the Companion receives a notification from the pump, the Companion displays a flashing notification bar at the top of the screen that indicates there is a pending notification. When the user interface returns to the Home screen, if the user has not already silenced the notification on the pump, the notification is displayed on the Companion.

Alert and recoverable alarm notifications are accompanied by audio or vibratory feedback on the pump, referred to herein as the attention sequence. In the exemplary embodiment, the sequence starts as a single tone (sounded from the safety processor speaker), pause, triple tone (sounded from the H8 processor speaker) sequence (or three vibrations when feedback is set to vibration). The sequence repeats every 15 second, in the exemplary embodiment, but in some embodiments, may repeat more regularly or less often, until the device times out or until the user interacts with the device. After a device time out, if there is no user interaction within 1 minute (in other embodiments, this duration may be longer or shorter), the user interface wakes up the pump and repeats the notification using an escalated attention sequence: when the feedback is set to vibration, feedback switches to audio; if the feedback was audio, the audio sequence escalates to a single short ton (from the safety processor speaker), pause, single long (siren) tone (from the H8 processor speaker) sequence. The siren tonie is an uninterrupted succession of tones of increasing frequency. Once the feedback has been escalated to siren, subsequent sounding of the attention sequence rotates from vibration, to audio, to siren. If the user interacts with the device after the attention sequence has been escalated, the next time the attention sequence is sounded, it reverts to the original attention sequence feedback. If the notification is sounded for 15 minutes without user interaction while the pump is in a delivery mode, delivery is stopped and the Inactivity Alarm notification is generated.

In the exemplary embodiments, when the user accepts the "Clear" action selection on a notification screen, the notification is cleared and the user interface closes the notification screen. When the pump checks again for the alert or alarm condition, if the alert or alarm condition still exists, the notification is repeated.

When the user accepts the "Sleep Time" item on a notification screen, the user interface displays the SET SLEEP TIME or opens the Sleep Time item for editing where the user may program the sleep time value. Accepting the "Sleep" action selection on the notification screen dismisses the notification for that user-programmable amount of time (15 minutes to up to 12 hours, depending on the notification). The user interface postpones checking for the condition or presenting the reminder alert again until the amount of time specified in Sleep Time has passed. If the user changes the clock time during the sleep period of an alert, the alert expiration time is adjusted accordingly, so that the alert (or check for the alert condition) is repeated when the amount of time is adjusted accordingly, so that the alert (or check for the alert condition) is repeated when the amount of time specified in the Sleep Time has elapsed, regardless of the clock time. In the exemplary embodiment, a date change has no effect on the expiration time of a reminder that has been slept.

With respect to clock time and date adjustments, in the exemplary embodiment, when the user changes the pump clock time or the date, the pump user interface adjusts the expiration time for all sleeping alerts, except the low insulin alert, to a time equal to the current expiration time plus (if time or date was adjusted forward) or minus (if time or date was adjusted backwards) the time or date adjustment. However, in the exemplary embodiment, as discussed herein, to change the clock time, basal delivery must first be stopped. When basal delivery is again started, both sleeping pump idle and low insulin alerts are reset.

With respect to the date, when the user changes the pump date forward in time, the pump user interface generates a reminder alert for all user programmable reminders that either have been cleared or have not yet expired (excluding reminders that have been slept). When the user changes the pump clock time only (no date change) to a time earlier than the time of a cleared user-programmable reminder alert, the pump user interface shall reset the reminder alert.

Figure 17:
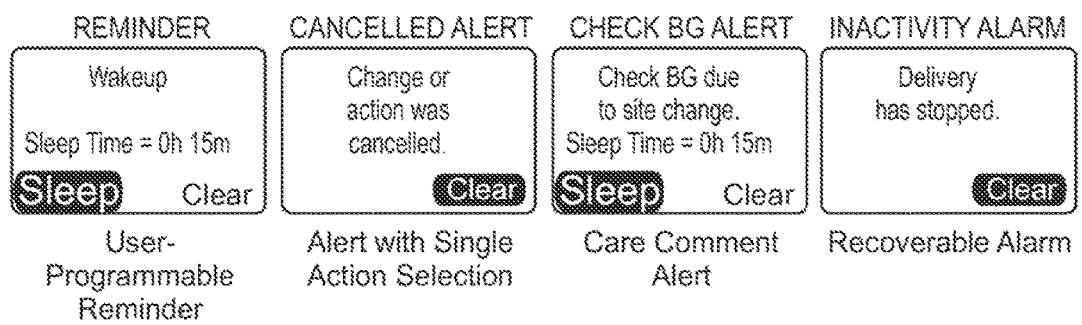
FIG. 17 shows an exemplary embodiment of at least one alert, reminder and recoverable screens.

In the exemplary embodiment, when the pump clock time is changed to a time later than the user-programmed times of a user-programmable reminder alert that has not yet expired (i.e., has neither been cleared nor slept) the user interface generates a reminder alert notification.

Where an alert, reminder or recoverable alarm condition occurs on the pump when the user interface is displaying the Home screen, the user interface produces the attention sequence on the pump and displays the notification screen that describes the condition. Referring now to FIG. 17, examples of alert, reminder and recoverable alarm screens are shown. If the pump is in a sleep state, the user interface wakes up the pump to present the notification. With respect to embodiments including a Companion, in the exemplary embodiment, on the Companion, if the Companion is awake and displaying the Home screen, the notification screen also is displayed on the Companion. If the Companion screen is asleep and the user wakes it up when the pump is displaying a notification, when communication with the pump resumes, the notification also is displayed on the Companion. The user interface allows the user to dismiss an alert or reminder for a programmable amount of time, which the user selects on the notification screen itself. There may be a few exceptions, in the exemplary embodiment, of alert screen that cannot be dismissed, but only cleared.

Figure 18A:
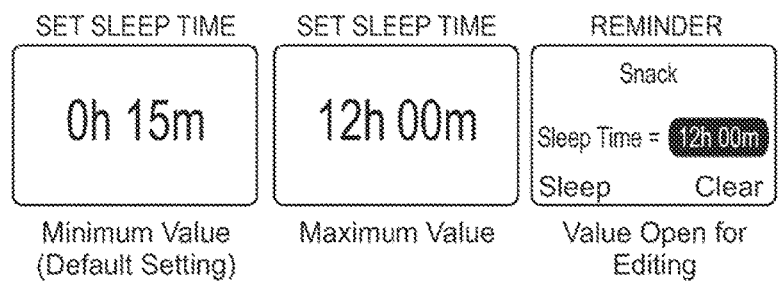
FIGS. 18A-18B shows an exemplary embodiment of at least a selection of REMINDER and SET SLEEP TIME screens according to an exemplary embodiment.
Figure 18B:
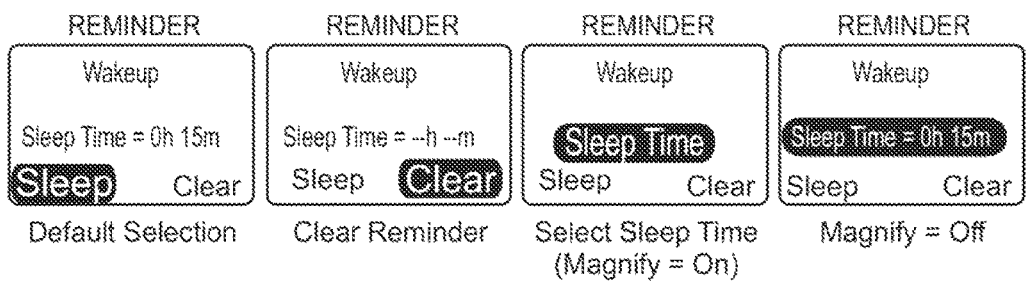
Figure 19A:
FIGS. 19A-19E shows exemplary embodiments of at least a selection of ALARM screens.
Figure 19B:
Figure 19C:
Figure 19D:
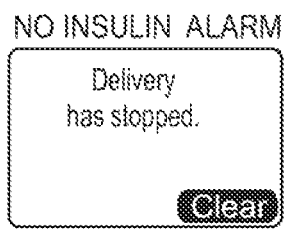
Figure 19E:
Figure 20A:
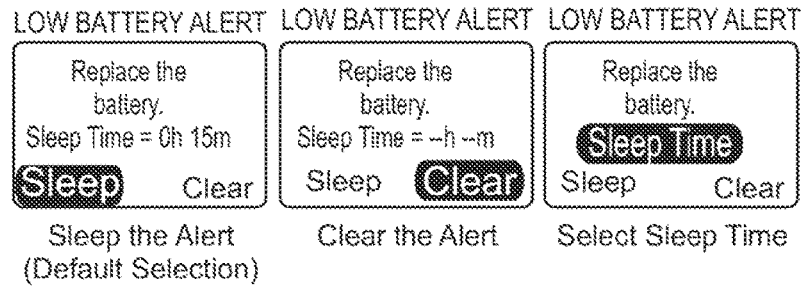
Figure 20B:
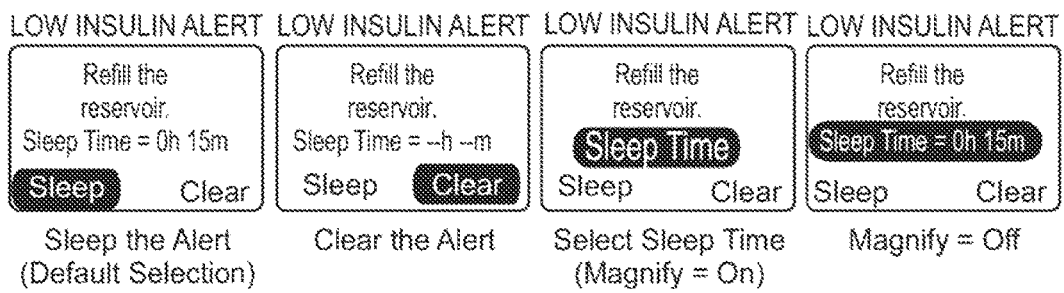
Figure 20C:
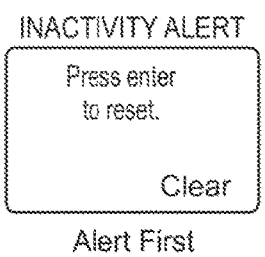
Figure 20D:
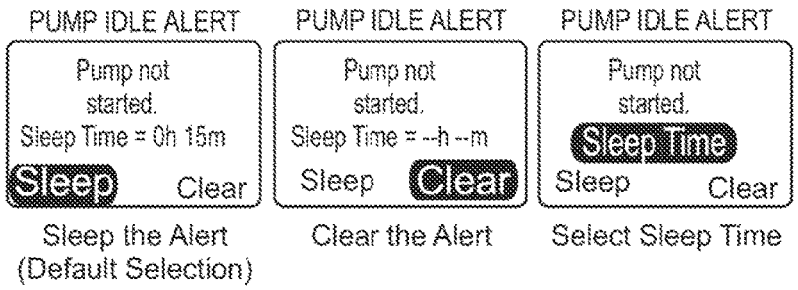
Figure 20I:
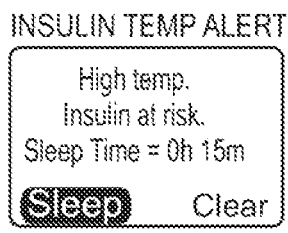

Referring now to FIG. 18A, in the exemplary embodiment, the user opens the SET SLEEP TIME edit item screen when the user accepts the Sleep Time item on an alert or reminder notification screen. The user accepts the Sleep Time item to define the period of time for which to sleep the notification. Referring now to FIG. 18B, in the exemplary embodiment, the user may program up to six reminders (however, in some embodiments, the user may program a greater number or reminders) specifying a time of day and choosing to enable or disable the reminder. The user interface generates a reminder alert for enabled reminders when the clock time changes to the user-programmed time for the reminder. The expiration time for all reminders that are "sleeping" is adjusted whenever the user change the pump clock time and/or date, so that the actual amount of time for which the alert is sleeping reflects elapsed time that matches the user-specified sleep time. When the user changes the clock time to a time later than the user-programmed expiration time for a reminder that has not expired, the reminder will be detected when the user returns to the Home screen, and the alert will be generated. Additionally, if the user changes the date forward, the pump user interface generates an alert for all enabled reminders that are not "sleeping" when the user returns to the Home screen.

For a bolus reminder, if the start of the normal bolus delivery (either a normal bolus, or the normal bolus portion of a dual bolus) occurred within 2 hours of an enables bolus reminder time, the user interface clears the bolus reminder alert. If the start of a normal bolus has not occurred within 2 hours of the programmed bolus reminder time, the user interface displays the reminder alert at the programmed time.

For a bolus reminder, if the start of a normal bolus delivery (either a normal blus, or the normal bolus portion of a dual bolus) occurred with 2 hours of an enabled bolus reminder time, the user interface clears the bolus reminder alert. If the start of the normal bolus has not occurred within 2 hours of the programmed bolus reminder time, the user interface displays the reminder alert at the programmed time.

In the exemplary embodiment, clearing a reminder does not disable the reminder. The alert condition will be detected again when the reminder expires (when the clock changes to the user-programmed time for the enabled reminder, or a time/date change causes the reminder to expire). The user interface will generate the reminder alert notification until the user disables the reminder through the ALARM SETUP: REMINDERS screen.

The user interface generates a reminder alert notification once a day for all user-programmable reminders that are enabled, provided the user does not change the clock time to a time earlier than the reminder after the reminder already expired; or does not change the date. When the user enables a reminder alert, if the user programmed time is later than the current clock time, the user interface generates the reminder alert notification before the end of the current 24-hour period. Conversely, when the user enables a reminder, if the user-programmed time for the reminder is earlier than the current time within the current 24-hour period, the user interface does not generate the reminder alert until the next day.

Referring to FIGS. 19A-19E, in the exemplary embodiment, with respect to alarm conditions, these include, but are not limited to: "OCCLUSION ALARM", "RESERVOIR ALARM", "BAD BATTERY ALARM", "NO INSULIN ALARM", and "INACTIVITY ALARM".

Referring to FIGS. 20A-20I, in the exemplary embodiment, with respect to alert conditions, these include, but are not limited to: "LOW BATTERY ALERT", "LOW INSULIN ALERT", "INACTIVITY ALERT", "PUMP IDLE ALERT", "STOPPED ALERT", "CANCELLATION ALERT" (i.e., when the device times out after a value has been changed but not saved), "CHECK BG ALERT" (when the CHECK BG care comment is enabled, this alert is generated by the user interface when 2 hours has elapsed since the last cannula prime), "SITE CHANGE ALERT" alert (when this user-programmable care comment is enabled by the user, the user interface generates this alert when the amount of time between the last cannula prime and the time specified by the user-programmable setting for the SITE CHANGE care comment Frequency item elapses), and "INSULIN TEMP ALERT" (when this user-programmable care comment is enabled, the user interface generates an INSULIN TEMP ALERT notification when the internal temperature of the Pump exceeds a threshold preset temperature, or is less than a threshold, preset temperature, which, in the exemplar embodiment is 96.8+/−3.6 degrees Fahrenheit (36+/−2 degrees Celsius) and 37.0+/−3.6 degrees Fahrenheit (2.8+/−2 degrees Celsius) respectively. In the exemplary embodiment, the infusion pump includes at least one temperature sensor inside the pump housing or pump body (and either in the reusable portion or the disposable portion of one embodiment of the infusion pump). In some embodiments, the infusion pump includes more than one temperature sensor. In some embodiments, the user interface may display a warning to the user when the temperature sensor indicates that a temperature change, above a predetermined threshold, has occurred. In some embodiments, a warning may indicate to the user, or in some embodiments, there may be an alert or alarm. In various embodiments, depending on whether the temperature change was an increase or a decease, there may be an indication to the user that an unintentional delivery or a delivery interruption may have occurred and that the user should follow their blood glucose levels accordingly. In some embodiments of some infusion pumps, where the pump is exposed to large temperature changes, a small amount of additional insulin or other fluid infusion or interruption of delivery may take place due to thermal expansion or contraction of the insulin or fluid volume. To minimize this condition and maintain pump delivery accuracy, the user may be warned to avoid large temperature changes with respect to the pump. The resulting insulin/fluid delivery or interruption in delivery more greatly affects users who use low basal rates.

As discussed above, Reminders may be user-programmed by the user into the user interface. In the exemplary embodiment, six reminders may be programmed, however, in other embodiments; a greater number of Reminders may be user-programmed. Each Reminder includes specified time for the reminder, a message and an indication of whether the Reminder is "on" or "off". Thus, the user may set up different Reminders in the six Reminder screens and save those settings, whether or not any of the Reminders are turned on. On any given day, the user may turn on or off any of the six reminders.

Figure 21A:
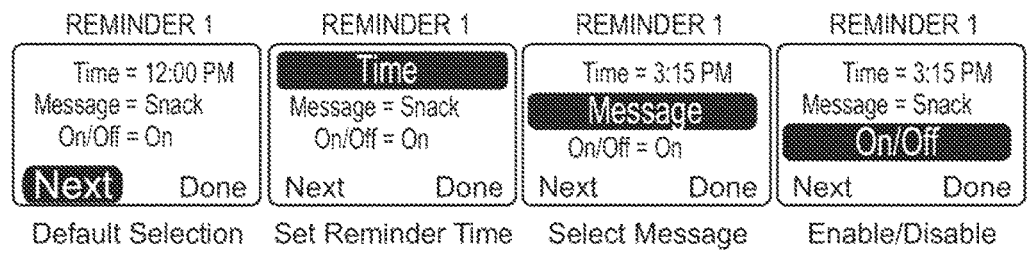
FIGS. 21A-21B show exemplary embodiments of at least a selection of REMINDER screens.
Figure 21B:
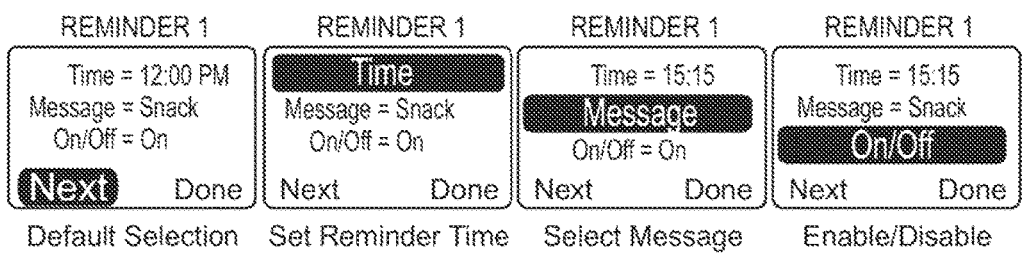

In the exemplary embodiment, the user interface presents a list of programmable values for the Message item, which include, but are not limited to: "Check BG", "Wakeup", "Basal", "Bolus", "Exercise", "Meeting", "Pickup", "Snack", "Meds". Referring now to FIGS. 21A-21B, an example of the REMINDER format screens are shown for both the 12-hour Time Format and the 24-Hour Time Format respectively.

In the exemplary embodiment, Care Comments, for example, "INSULIN TEMP", "SITE CHANGE", "CHECK BG", may be individually enabled or disabled by the user. The Care Comments generate a CARE COMMENT ALERT at the specified time. With respect to INSULIN TEMP, as discussed above, once this Care Comment is enabled, a CARE COMMENT ALERT will be generated when the temperature inside the pump either exceeds or goes below the set threshold. With respect to CHECK BG, this Care Comment, when enabled, will ALERT 2 hours following a cannula prime.

Figure 22:
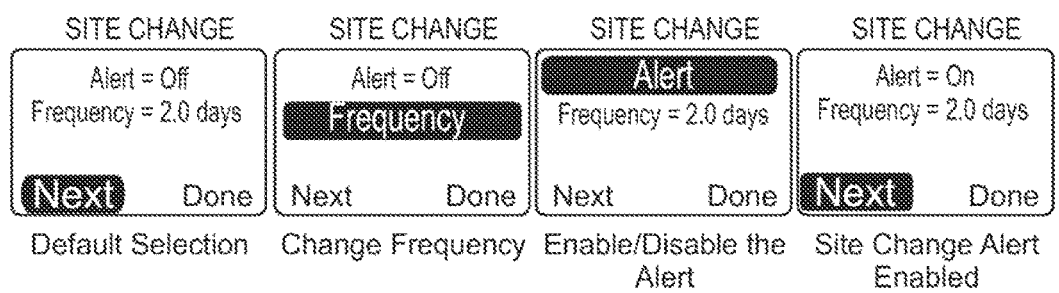
FIG. 22 shows an exemplary embodiment of at least a selection of screens for setting the Frequency of a SITE CHANGE Care Comment.

Referring now to FIG. 22, with respect to the SITE CHANGE, this Care Comment requires the user to select the Frequency based on the last cannula prime. For example, if the user sets the Frequency to "3.0 days", when the SITE CHANGE care comment is enabled, the pump with SITE CHANGE ALERT 3.0 days following the latest in time cannula prime.

With respect to the Care Comments, in the exemplary embodiment, the user interface provides a "Disable All" option that allows the user to disable all Care Comment alerts. When the "Disable All" items on the OPTIONS screen is set to "Yes", this setting overrides the individual settings for the INSULIN TEMP, SITE CHANGE and CHECK BG Care Comment settings.

Basal and Pump Idle

In the exemplary embodiments, the infusion pumps may deliver a "basal" of fluid or insulin, in the exemplary embodiment. In the exemplary embodiments, the term "basal" takes on its accepted meaning of a doss of insulin or other fluid delivered at a "rate", typically, Units/Hour. The infusion pump may be placed in an "IDLE" mode by the user through the "STOP BASAL" function of the user interface. Also, as discussed herein, the pump may place itself into IDLE mode in some circumstances. Thus, IDLE is a mode in which the pump stops delivery of the basal rate. Additionally, in IDLE mode, the pump, in the exemplary embodiment, can not deliver any insulin, thus, the pump's delivery is suspended or "idle".

In the exemplary embodiments, IDLE mode is required for functions where there delivery may be affected. Those functions may include, but are not limited to: change to the date and/or time; change of hardware, i.e., reservoir or battery; and/or a change in the currently active basal rate; and/or change to basal limits.

In the exemplary embodiment, once the pump is placed into IDLE mode, the pump will alert the user at an interval, e.g., every 5 minutes. This is a safety measure to ensure the user is aware the pump is not delivering. Thus, the IDLE mode is instigated by the user, and therefore, the user is aware the pump is not delivering. As the pump will remind the user of the IDLE mode, this ensures the user is continuously aware the pump is not delivering.

With respect to power, in the exemplary embodiment, where the pump senses there is no power, the pump will notify the user as the pump will assume there has been a battery failure. However, where a user is changing the battery (i.e., changing the power source), the user is aware that there will not be power for the time it takes to replace the battery. In the exemplary embodiment, the user may place the pump into IDLE while changing the battery. Thus this tells the pump that the power failure is expected. Thus, this failure analysis feature assists the pump in distinguishing between a power failure and an intended power supply removal.

In this way, the pump only allows a silent shutdown (a shutdown not accompanied by a notification from the pump) when the user places the pump in IDLE before removing the battery. As a safety, however, in the exemplary embodiments, the pump will continue its IDLE TIMER, and will alert the user at an interval, that the pump remains in idle. This also will occur where the battery or power source has been removed, as in the exemplary embodiment; the infusion pump includes a super capacitor back-up power supply that will prevent the infusion pump from having a silent shutdown as the infusion pump will have the power to alert the user of the shutdown. Further, the super capacitor/back-up power supply allows the infusion pump to notify the user at intervals during IDLE mode, even when the power supply has been removed and before a power supply has been replaced.

Bolus

In the exemplary embodiments, the term "bolus" takes the meaning of a volume of insulin delivered upon request. The term "normal" bolus equates to a bolus where delivery commences upon request. The term "extended bolus" refers to a volume of insulin delivered over a user-programmed period of time. Thus, for example, a "normal" bolus may be 5.5 U, where delivery is commenced at request. An "extended" bolus or 5.5 U may be delivered over 2 hours. A "dual" bolus is a combination of a normal bolus and an extended bolus, where the user specifies the units to be delivered as a normal bolus, and the time over which the extended bolus is to be delivered. For example, a dual bolus of 6.5 U may be delivered as follows: 1 U delivered as a normal bolus, and 5.5 U delivered over 2 hours. Additionally, in the exemplary embodiment, a bolus termed a "Qbolus" refers to a QUICK BOLUS, which is a normal bolus in which the user interface immediately brings the user to a screen where the user simply scrolls to enter the Units for the normal bolus.

Figure 23A:
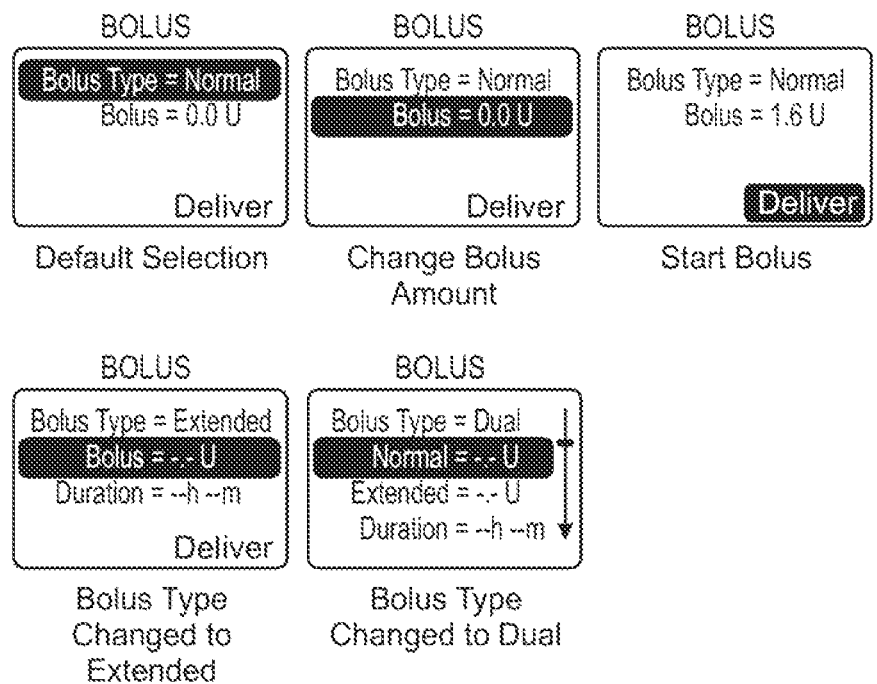
FIGS. 23A-23B, show exemplary embodiments of at least a selection of BOLUS screens.
Figure 23B:
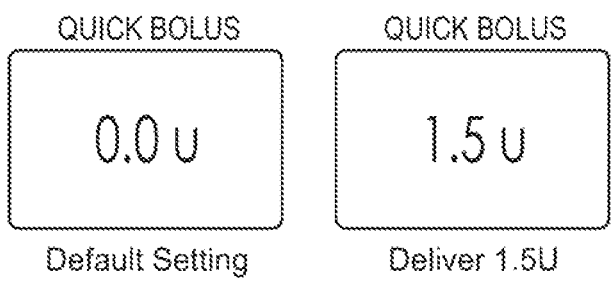

Referring now to FIGS. 23A-23B, a selection of at least some BOLUS screens are shown. Referring first to FIG. 23A, one of the methods of programming and delivering a normal bolus is by selecting the MANUAL item on the BOLUS MENU screen, which displays the BOLUS select item for edit screen. Through the BOLUS screen, the user may program a Normal, Extended or Dual bolus. The values that appear on the screen vary depending on the bolus type that the user selects.

The Extended bolus features allow the user to deliver a bolus over a longer period of time by specifying a length of time over which the bolus should be delivered. When programming an Extended bolus without using a bolus calculator, the Bolus item is set to dashes. When using the Food only calculator, the Bolus item is set to the calculated Carb Insulin value; for a Food and Correct or Food & Correction bolus, the Bolus item is set to the calculated Carb Insulin value minus the IOB amount. For any calculated bolus, the bolus amount is based on the pump delivery resolution (which may vary between pump embodiments) regardless of the user-programmable bolus increment. However, when the user makes a change to a calculated value on the BOLUS screen, the user-programmed bolus increment is used. For example, if the calculated value was 0.55 U, and the bolus increment settings is 1.0 U, when the user edits the Bolus value, a downward increment changes the value to 0.0 U, and an upward incrememt changes the value to 1.0 U.

Also, in the exemplary embodiment, if the user changes the Bolus amount for an extended bolus to 0.0 U, the Duration item is removed from the BOLUS screen. The user is allowed to accept Deliver for a 0.0 U bolus, but no bolus history is generated for a 0 bolus.

A dual bolus allows the user to program and deliver a bolus that consists of a normal bolus that is delivered immediately, and an extended bolus that is delivered over an extended (user-defined) period of time. When an extended bolus is currently running, the user is not allowed to program a dual bolus. If the user changes the Extended amount of 0.0 U, the Duration item is removed from the BOLUS screen. The user is allowed to accept Deliver for a 0.0 I bolus, but no bolus history is generated for a 0 bolus.

Referring now to FIG. 23B, QUICK BOLUS screens are shown. A QUICK BOLUS, or

QBOLUS screen displays a programmable number, allowing the user to quickly program a normal bolus, bypassing the screen on which the bolus type is selected. In the exemplary embodiment, a QUICK BOLUS is delivered as a Normal bolus.

In the exemplary embodiment, while the pump is in IDLE, a bolus may not be delivered. If a user requests a bolus delivery and the pump is in IDLE, the user interface will remind the user to "Stan Basal before blousing". This serves as a reminder to the user that the pump is in IDLE, and thus, the user must start basal prior to blousing.

Additionally, in the exemplary embodiment, while the pump is delivering an extended bolus, if the user requests a second extended bolus, the user interface will display a WARNING "Extended Bolus already in progress". This serves to remind the user they have already programmed an extended bolus.

A correction bolus is a bolus calculated using the 1 U DROP value discussed above, and used to calculate how much insulin to deliver to bring the user's blood glucose value to a desired level. In the exemplary embodiment, when CORRECTION is selected from the BOLUS, if this is done within 2 hours of the last bolus when the Insulin Profile Type setting is Rapid, or 3 hours of the lat bolus when the Insulin Profile Type setting is Short, the user interface displays the "Less than ⅔ hours since last bolus" WARNING. The user may still continue programming a correction bolus after accepting "OK". This WARNING screen serves to inform the user of the duration since their last bolus before they proceed with requesting a correction.

Figure 24A:
FIGS. 24A-24D shows exemplary embodiments of at least a selection of WARNING and CONFIRM screens.

Referring now to FIG. 24A, in the exemplary embodiment, when bolus data is not available for the entire action time period, the user interface displays the IOB value on the Home screen with a greater than or equal symbol, and generated the "IOB may not include all boluses" WARNING when one or more of the following are true, which include, but are not limited to:

1) When less time than the user-programmed action time has elapsed since the bolus log was initialized, and the user accepts the Next action selection on the BLOOD GLUCOSE screen (in the exemplary embodiment, the bolus log is initialized when the pump is without power for at least 15 minutes and the time and date is set to dashes at power up);
2) When the number of boluses in the bolus history that occurred with the user-programmable action time exceeds 10, or the IOB amount is greater than 300, and the user accepts Next action selection on the BLOOD GLUCOSE screen.
3) When there is no bolus history due to loss of time and date, and the user accepts then Next action selection on the BLOOD GLUCOSE screen.
4) When the user presses the back button on the BOLUS screen that was populated with a calculated Insulin value from the BLOOD GLUCOSE screen, and the IOB value is displayed on the BG CALC DETAILS screen with a question mark.

Figure 24B:
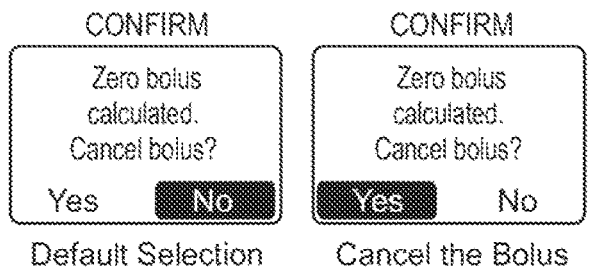

Referring to FIG. 24B, in the exemplary embodiment, with respect to programming a bolus using one or both calculators (correction calculator or food and correct calculator), if the Bolus amount calculates to a value less than or equal to 0.0 U, the user interface displays the "Zero bolus calculated. Cancel bolus?" CONFIRM screen.

Figure 24C:
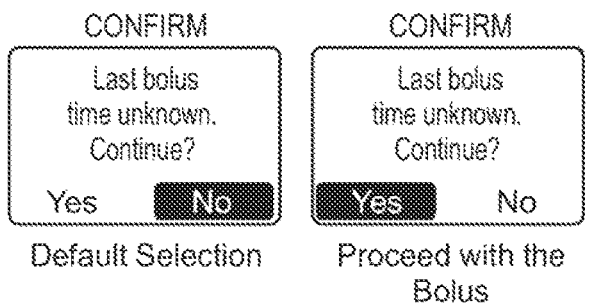

Referring to FIG. 24C, when a bolus history has been established (which, in the exemplary embodiment, is established when at least one bolus has been delivered); the user interface calculates the amount of IOB that is still active to subtract from the calculated insulin amount for a Correction bolus. When there is no bolus history and at least 2 hours (when insulin profile setting is Rapid) or 3 hours (when insulin profile setting is Short) have not yet elapsed since the bolus log was initialized, if the user programs a bolus using the Correction calculator, the user interface displays the "Last bolus time unknown. Continue?" CONFIRMATION screen, when the user accepts the FOOD & CORRECT or just CORRECTION item on the BOLUS MENU screen.

Figure 24D:
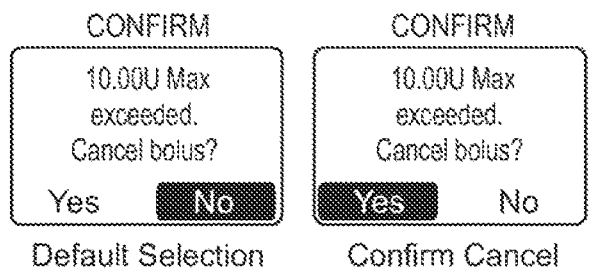

Referring now to FIG. 24D, in the exemplary embodiment, the user interface imposes a maximum bolus for all types of boluses, defined by the user-programmable setting, Bolus Limits Maximum (SETUP:BOLUS LIMITES). The user interface displays the "Maximum bolus of [nn.nn] U exceeded. Cancel Bolus?" CONFIRMATION screen when the user does at least, but not limited to, any one of the following:

1) Programs a bolus using either the Correction or Food calculator, and attempts to deliver a bolus with a calculated insulin value that is greater than the maximum bolus limit. In the confirmation message text, [nn.nn] U is the value of the maximum bolus limit setting (SETUP: BOLUS LIMITS). The user interface displays the confirmation screen when the user selects "Next" on the FOOD or BLOOD GLUCOSE, and the bolus value calculation is greater than the user-programmable setting for bolus maximum limit.
2) Programs a dual bolus and the total bolus amount for the combined Normal and Extended exceeds the maximum bolus amount. The user interface displays the confirmation screen when the user selects Deliver on the Dual Bolus screen when the combined bolus amount is greater than the user-programmable setting for bolus maximum limit.

As discussed above with respect to the Home screen, the user interface includes readily available information regarding the IOB and the last bolus. In the preferred embodiment, the Units and the amount of time elapsed since the last bolus may be on the Home screen. Additionally, in the exemplary embodiment, the user interface includes a series of HISTORY screens. Referring now to FIG. 25, when the user accepts the HISTORY item on the BOLUS MENU or REPORTS MENU screen, the user interface displays the HISTORY 1 of n screen. The user may clock through history details for the 10 most recently delivered boluses. In other embodiments, more than the 10 most recently delivered boluses may be available using this feature. The HISTORY screens show records for completed boluses, including normal (which includes one-button and Qboluses), and extended boluses. The records are ordered by completion time, with the most recently completed boluses displayed first. Thus, the user interface provides easy access to the last 10 bolus records, including both the Units, the type of bolus (e.g., normal, extended, etc.) and the elapsed time since the bolus was completed.

Diary and Reports

Figure 26:
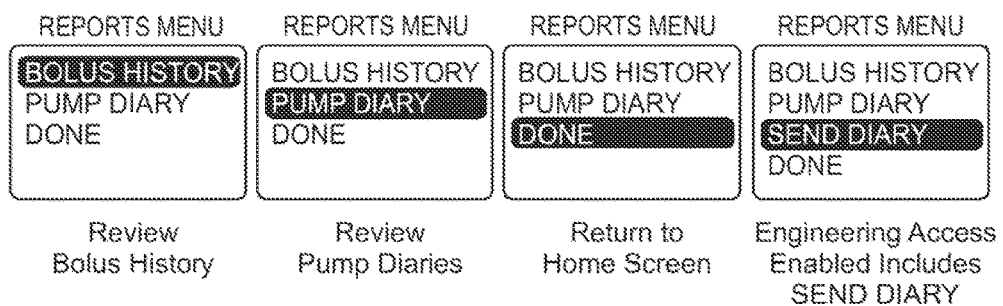
FIG. 26 shows an exemplary embodiment of at least a selection of REPORTS screens.

Referring now to FIG. 26, in the exemplary embodiment, the REPORTS MENU screens provides access to the pump diaries and the bolus history. After the pump is fully initialized, the user accesses the REPORTS MENU screen by selecting REPORTS on either the MAIN MENU screen, or the Activity-Based Home screen. On the pump, when engineering access is enabled, the REPORTS MENU screen includes a SEND DIARY option for sending pump logs to a PC. These are described with respect to FIGS. 31-34D.

Figure 27:
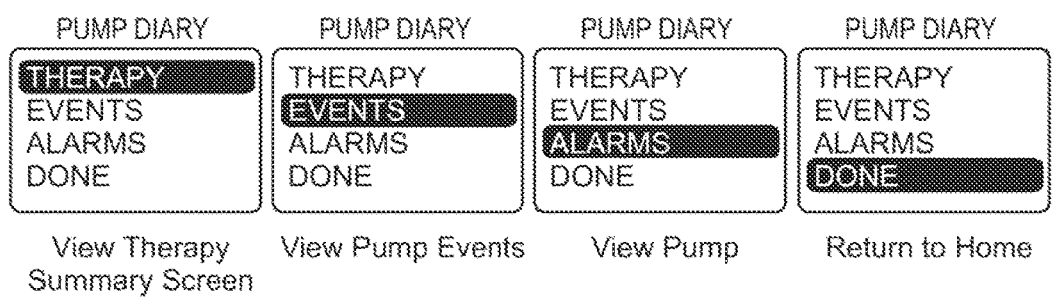
FIG. 27 shows an exemplary embodiment of at least a selection of DIARY screens.

Referring now to FIG. 27, in the exemplary embodiment, when the user selects and accepts the PUMP DIARY items on the REPORTS MENU screen, the user interface displays the PUMP DIARY screen, from which the user may select to view or send diaries.

Figure 28:
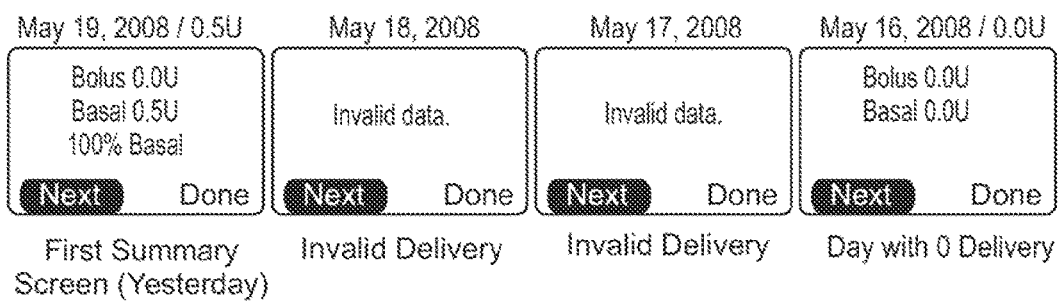
FIG. 28 shows an exemplary embodiment of at least a selection of DAILY THERAPY screens.

Referring now to FIG. 28, in the exemplary embodiment, when the user accepts the THERAPY item on the PUMP DIARY screen, the user interface displays the Daily Therapy Summary screen for the current day (the 24-hour period beginning at 12 AM in the exemplary embodiment). The Daily Therapy Summary screen shows the total daily dose, which includes all basal and boluses delivered for that 24 hour period, and excludes volume delivered through device primes. For an extended bolus that spans more than one day, the total daily dose includes that portion of the extended bolus that was delivered within the 24 hour period. The user may scroll through Daily Therapy Summary screens for up to the previous 30 days. The first entry is the current calendar day; the $30^{th}$ entry is 30 calendar days ago. For example, if the current date is Jun. 14, 2008, the first daily therapy entry is June 14 and the $30^{th}$ entry is May 16. If there is no delivery data in the therapy diary for 29 days earlier that the current date, the user interface displays Daily Therapy Summary screens for the number of days from the current date to the earliest date in the therapy diary.

The therapy diary is read from the most recent date to backwards in time. While reading the therapy diary, if the user interface encounters an entry with a later date than the last event that was read, the delivery data for that day (the day of the last event that was read) is considered complete with all entries are ignored until an earlier date is found. When there is no delivery data for a given date the total daily dose summaries for that date are 0.0 U and the % Basal item is removed form the Therapy Summary screen.

If the diary entries indicate a basal rate other than 0 when a powerup event was encountered, the summary details for that day are removed from the Therapy Summary screen, and "Invalid data" is displayed instead. If the current day is the first day of pump usage and the first basal delivery begins later than 12 AM, the period of time between 12 AM and the first basal delivery date is represented as 0.0 U/h. Similarly, the period of time between the time when the user accepted the THERAPY item on the PUMP DIARY screen and the end of the current 24-hour period also is represented as 0.0 U/h.

Figure 29A:
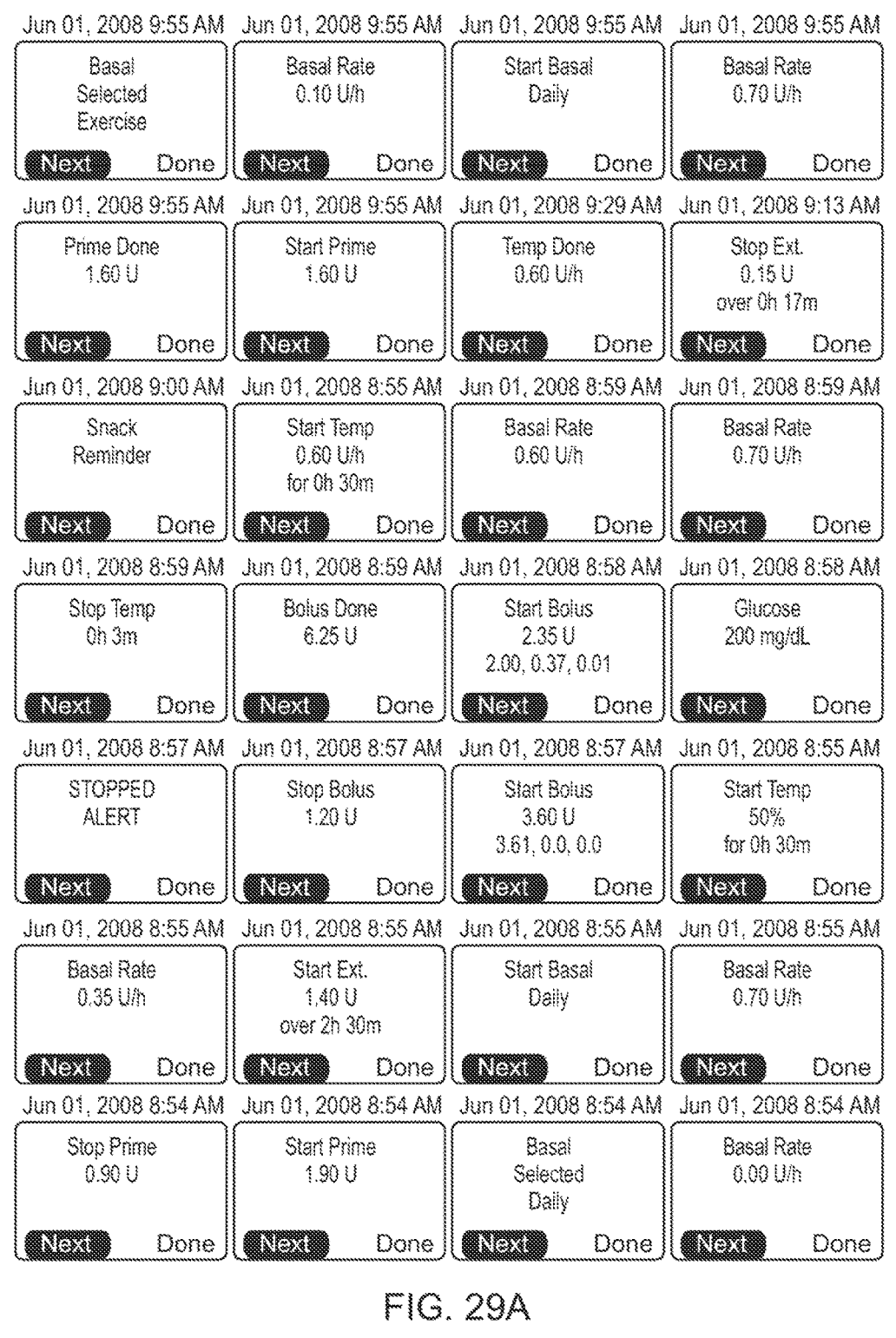
Figure 29B:
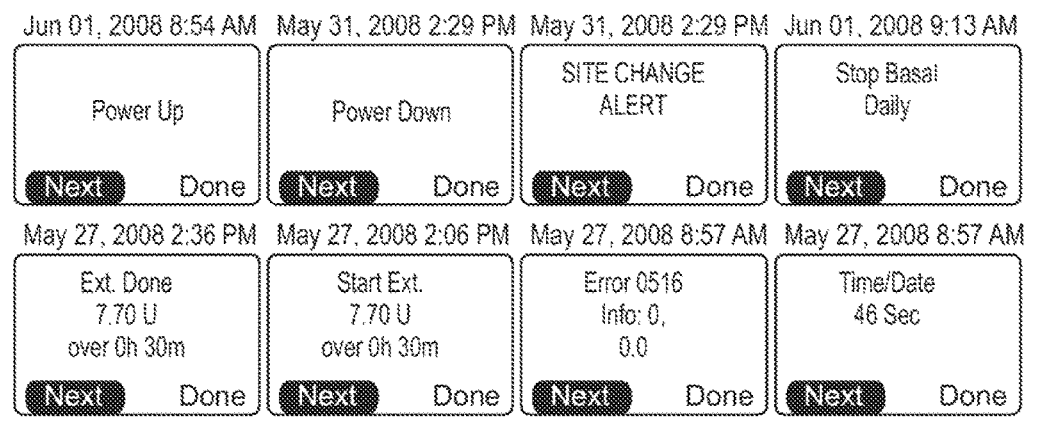

Referring now to FIGS. 29A and 29B, in the exemplary embodiment, when the user accepts the EVENTS item on the PUMP DIARY screen, the user interface displays the Event Summary screen for the pump event that occurred most recently. The Event Summary screen displays the date and time that the event occurred, a description of the event, and may or may not include additional details, depending on the event. For example, related to delivery include programmed and delivered amounts; other events such as extended boluses and temporary basals include durations. The user may review Event Summary screens for at least 150 events (however, in other embodiments, additional events, i.e., greater than 150, may be viewable), which are ordered from the event that occurred most recently (first entry) to the event that occurred farthest in the past (last entry).

Referring now to FIG. 30, in the exemplary embodiment, when the user accepts the ALARMS item on the PUMP DIARY screen, the user interface displays the Alarm Summary screens for the most recent recoverable or non-recoverable alarm. The user may scroll through Alarm Summary screens from past alarms.

Figure 31:
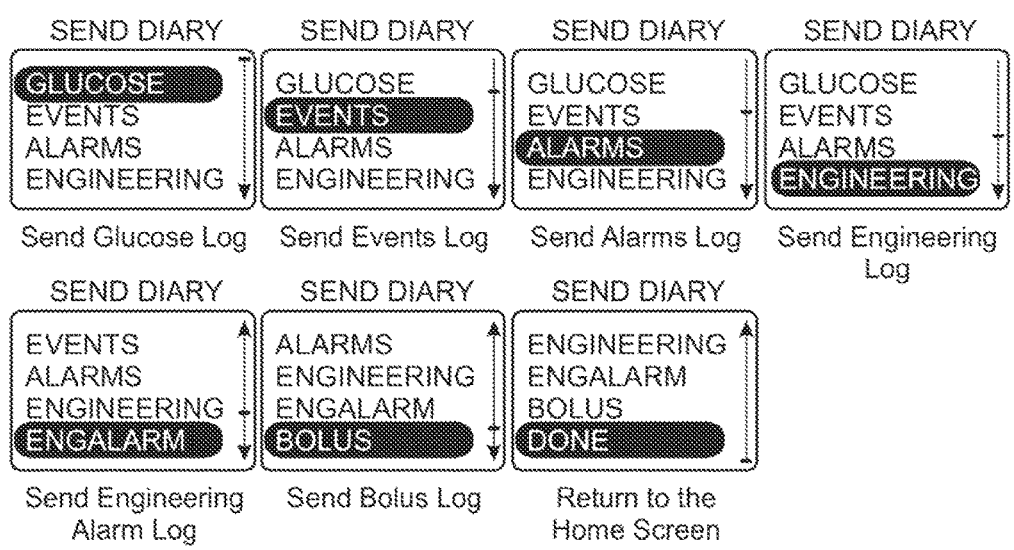
FIG. 31 shows an exemplary embodiment of at least a selection of SEND DIARY screens.

Referring now to FIG. 31, in the exemplary embodiment, when the engineering access is enabled, the REPORTS MENU screen includes a SEND DIARY item. When the user accepts the SEND DIARY item on the REPORTS menu screen, the user interface displays the SEND DIARY screen. Here, the user may select from a list of logs to send to a PC.

Figure 32:
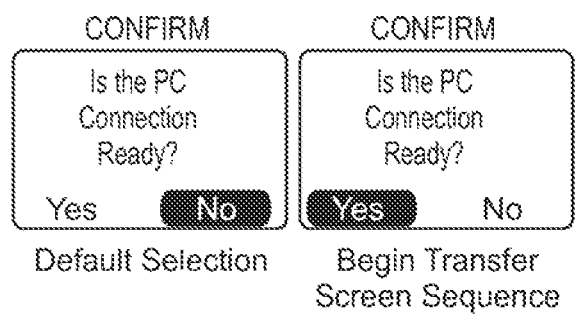
FIG. 32 shows an exemplary embodiment of at least a selection of screens related to the PC Connection.

Referring now to FIG. 32, in the exemplary embodiment, when the user accepts the SEND DIARY item on the REPORTS MENU screen, then accepts any item other than DONE on the SEND DIARY select item screen; the user interface displays the "In the PC Connection Ready?" confirmation screen. When the user interface displays the SEND DIARY screen after the user selected "Yes" on the "Transfer Another Log?" confirmation screen, and the user selects any item other than "Done", the "Is the PC Connection Ready?" screen is not displayed.

Figure 33:
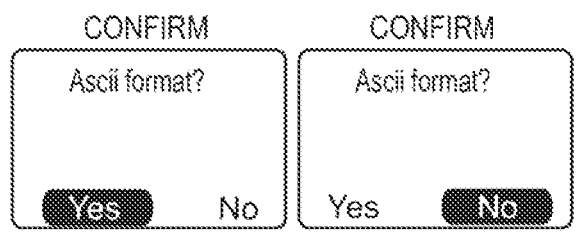
FIG. 33 shows an exemplary embodiment of at least a selection of screens related to the diary log transfer to a PC.

Referring now to FIG. 33, when engineering access is enabled, the user may send diary logs to the PC. In the exemplary embodiment, while transferring a diary log, the user may choose to write the resulting log file to the PC in ASCII format. After the user has confirmed that the PC connection is ready by selecting "Yes" on the "Is the PC Connection Ready?" confirmation screen, the user interface displays the "Ascii format?" confirmation screen.

Figure 34A:
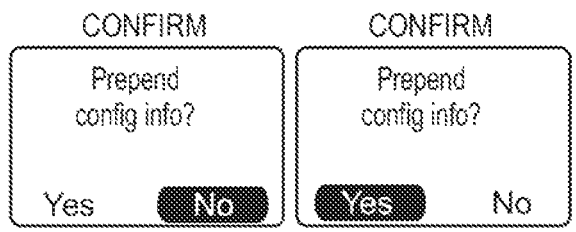
FIGS. 34A-34D shows an exemplary embodiment of at least a selection of screens related to the diary log transfer to a PC.

Referring now to FIG. 34A, in the exemplary embodiment, when engineering access is enabled, the user may send diary logs to the PC. While transferring a diary log, the user may choose to prepend configuration information in the resulting log file on the PC. After the user has selected "Yes or "No" on the "Ascii format?" confirmation screen, the user interface displays the "Prepend config info?" confirmation screen.

Figure 34B:
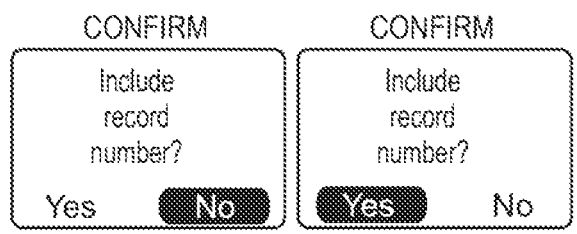

Referring next to FIG. 34B, in the exemplary embodiment, when engineering access is enabled, the user may send diary logs to the PC. While transferring a diary log, the user may choose whether to include record numbers in the resulting log file on the PC. After the user has selected "Yes or "No" on the "Prepend config info?" confirmation screen, the user interface displays the "Include record number?" confirmation screen.

Figure 34C:
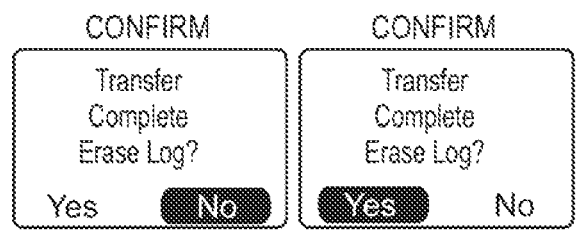

Referring now to FIG. 34C, in the exemplary embodiment, when engineering access is enabled, the user may send diary logs to the PC. While transferring a diary log, the user may choose to erase the log on the pump. The user interface transitions from the SENDING screen to the "Transfer Complete Erase Log?" confirmation screen when the data transfer has finished.

Figure 34D:
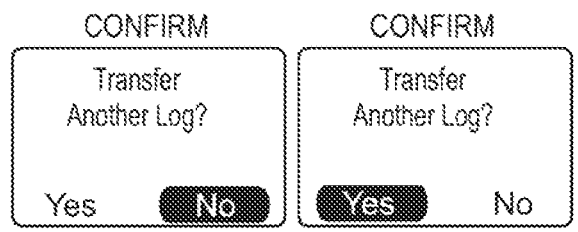

Referring now to FIG. 34D, in the exemplary embodiment, when engineering access is enabled, the user may send diary logs to the PC. Once one log has been transferred, the user interface displays the "Transfer Another Log?" screen. Where the user selects "Yes", the user interface returns to the SEND DIARY menu.

Infusion Pump System

Figure 35:
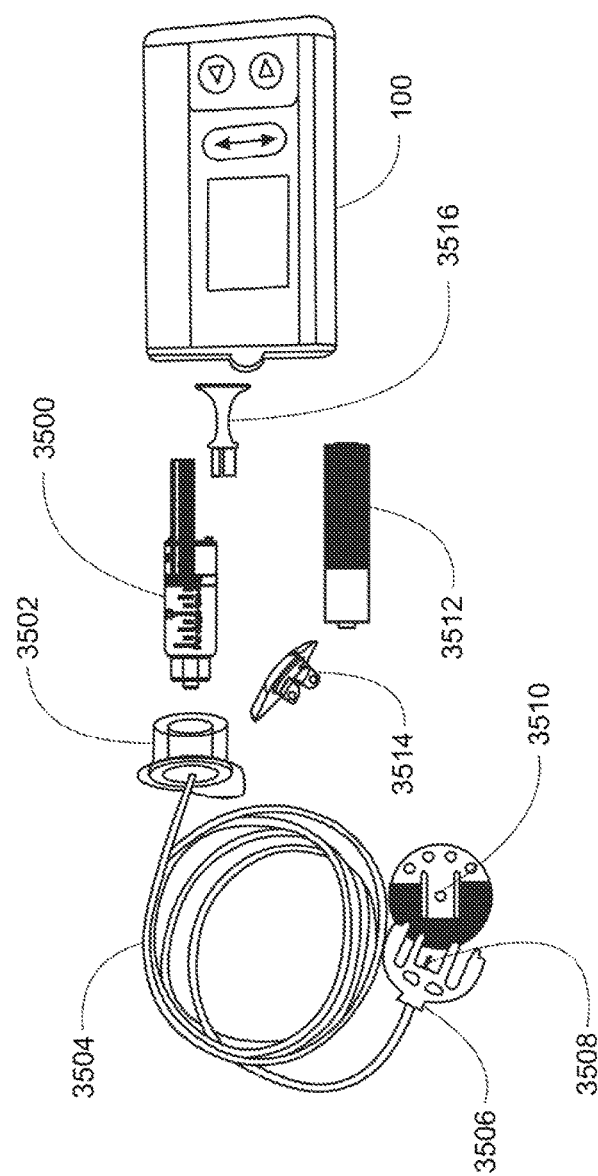
FIG. 35 shows an embodiment of an infusion pump system.
Figure 36:
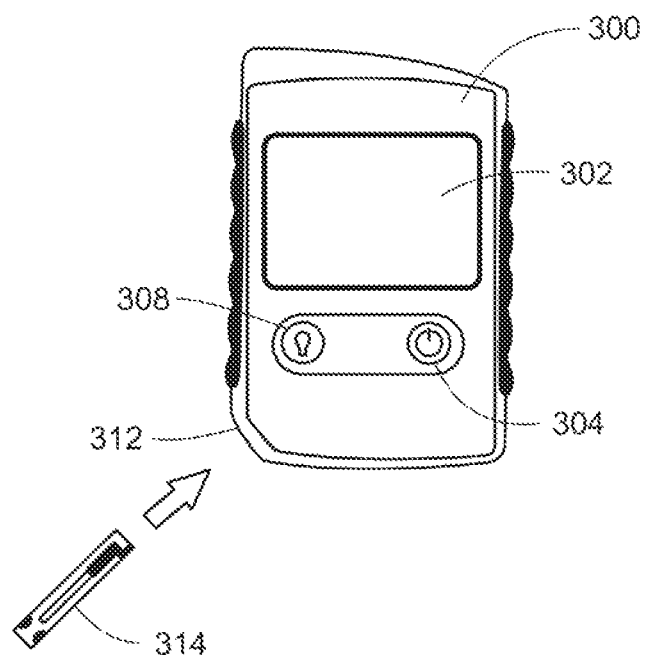
FIG. 36 shows an embodiment of a companion/remote control device.

Referring now to FIGS. 35-36, an infusion pump system may include at least one reservoir 3500 which, in some embodiments, may be a cartridge and/or a syringe like reservoir as shown in FIG. 35, which may be similar to one described and shown in U.S. patent application Ser. No. 12/249,882, filed Oct. 10, 2008 and entitled Infusion Pump Assembly (F51) which is herein incorporated by reference in its entirety. However, in some embodiments, the reservoir may be any component of the infusion pump system adapted to contain a fluid which is intended to be infused. In some embodiments, the reservoir may be one similar to those described in U.S. patent application Ser. No. 11/704,886, filed Feb. 9, 2007 and entitled Patch-Sized Fluid Delivery Systems and Methods, now U.S. Publication No. US-2007-0219480, published Sep. 20, 2007 (E72) and U.S. patent application Ser. No. 12/347,985, filed Dec. 31, 2008 and entitled Infusion Pump Assembly, now U.S. Publication No. US-2009-0299277, published Dec. 3, 2009 (G75), which are herein incorporated by reference in their entireties.

In some embodiments, the system may include at least one hub 3502 or other for connecting the infusion tubing 3504 to the reservoir 3500. In some embodiment, the infusion tubing 3504 may include a connector 3506, which in some embodiments, may include a connector needle 3508 for piercing a septum in the cannula 3510. The cannula may be any cannula known in the art or any such device for connecting infusion tubing such that fluid in a reservoir may be infused into a user/patient there through.

Still referring to FIG. 35, the system includes at least one pump 100. Again, as discussed above, the pump may be any infusion pump and in some embodiments, may be an infusion pump as shown and described with respect to FIGS. 1A-1F or FIGS. 2A-2D, or as shown and described in any of the various references incorporated by reference. However, in other embodiments, the pump may be any infusion pump. In some embodiments, the pump 100 may include a removable power supply which may include a battery 3512 and may also include a battery cap 3514. In some embodiments, the reservoir 3500 may also include a removable reservoir plunger handle 3516, some embodiments of which are described in U.S. patent application Ser. No. 12/249,882, filed Oct. 10, 2008 and entitled Infusion Pump Assembly (F51) which is herein incorporated by reference in its entirety. In some embodiments, the system may include two or more pumps that may be paired with the Companion.

Referring now to FIG. 36, an embodiment of a Companion 300 is shown. As discussed above with respect to FIG. 3, various embodiments of the Companion 300 may include a display assembly 302 and switch assemblies 304, 308. In some embodiments, the Companion 300 may also include a strip reader 312, which in some embodiments, may be a blood glucose strip reader 314. However, in some embodiments, the strip reader 312 may be adapted to be used to test/determine the presence of any analyte within a bodily fluid or other fluid. As discussed above, the Companion may additionally include a receiver for at least one continuous analyte sensor, which, in some embodiments, may be at least one continuous glucose sensor and/or one or more other sensors.

In some embodiments where the system includes both a Companion and a pump with a display, the pump and the Companion user interface may include approximately identical screens. This may be desirable as the user/caregiver learns one set of screens/one user interface and may control all aspects/functions of the pump from either or both the pump or the Companion. Additionally, the pump and Companion having approximately identical screens may also be desirable so that all functionality of the system may be accessed through either the pump or the Companion. Thus, in some embodiments, where a user may elect to wear the infusion pump under their clothing, the user may program and access all functionality of the system through the Companion. Thus, all screens/functions described herein may be accessible on both the Companion and the pump in some embodiments. However, in some embodiments, the pump may not include a display screen.

Referring now to FIG. 37A, target ranges for an analyte may be entered into the system. In some embodiments, this information may be entered into the Companion and/or the pump and/or both the Companion and the pump. As discussed above, the Companion may include a strip reader and/or may be a receiver for a continuous analyte sensor. The user/caregiver may choose to enter target ranges for the analyte, which, in some embodiments, may be blood glucose and/or interstitial glucose. In some embodiments, the target values may include a low target and/or a high target, but in other embodiments, the target values may include an average and/or a mean value and in still other embodiments, the target values may include a target for a specific event, for example, but not limited to, at least one target for a meal, exercise, illness, sleep, etc. In some embodiments, the target values may be entered into the Companion and/or the pump. In some embodiments, the targets may additionally include specificity with respect to time elapsed since an event, for example, but not limited to, 2 hours post food bolus, 1 hour after exercise, 1 hour after sleep, etc.

Figure 37B:
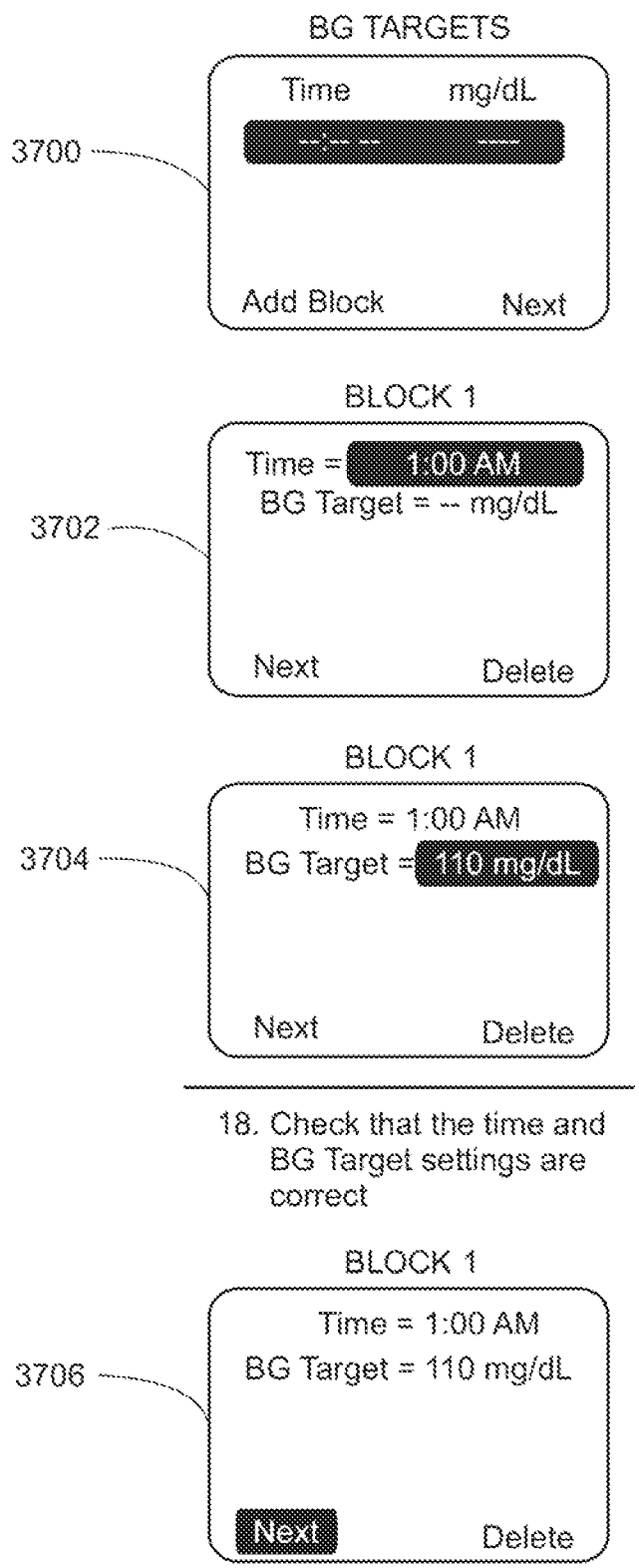

Referring now to FIG. 37B, in some embodiments, the targets may be entered with respect to time. For example, in some embodiments, at least one blood glucose ("BG") target may be entered with respect to time (see 3700-3704 in FIG. 37B). Once this information is entered by the user/caregiver, the block is completed; one embodiment of a resulting view 3706 is shown. In some embodiment, again, the targets with respect to time may be in relation to an event, i.e., elapsed time since the start of an event and or since the end of an event.

Figure 38:
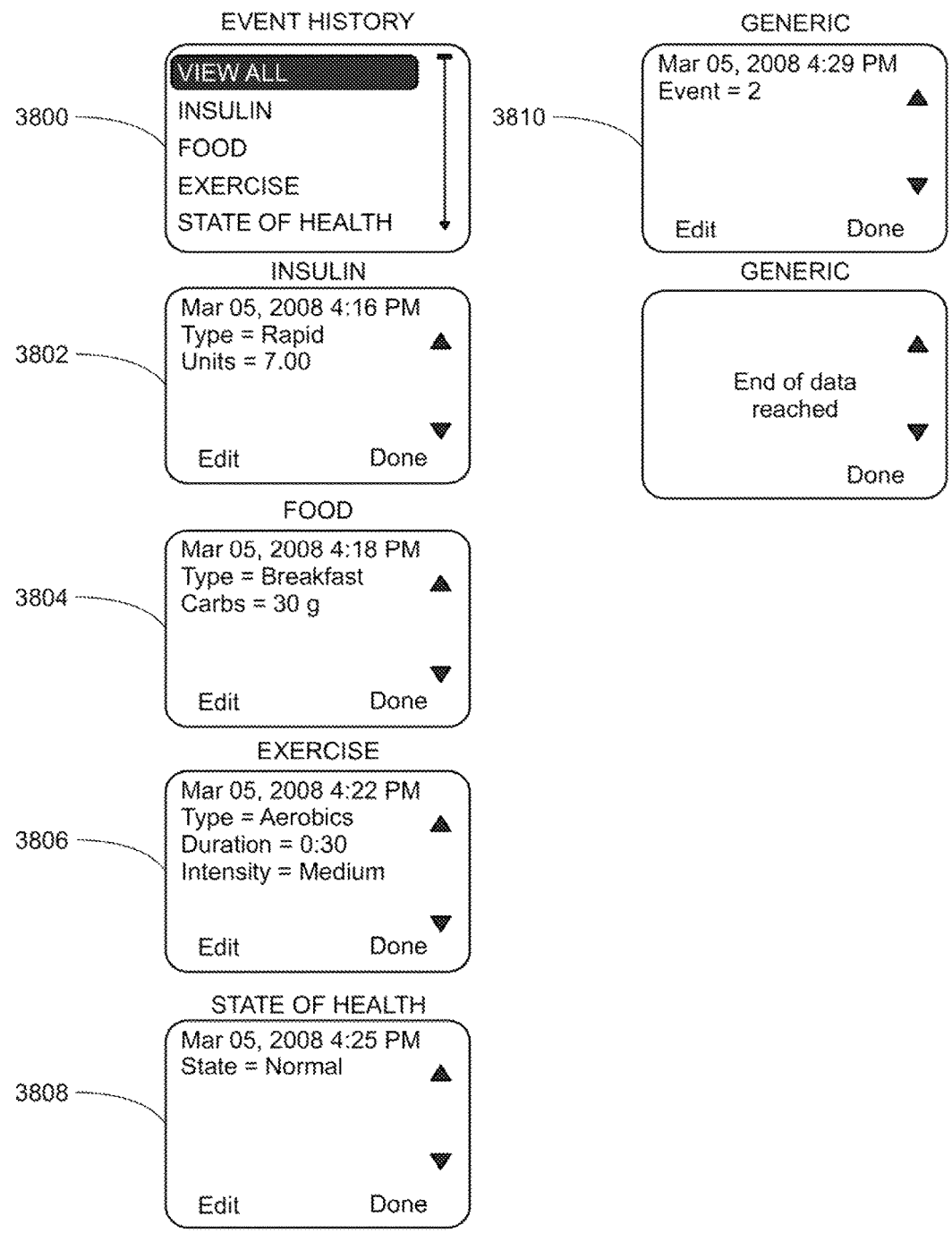
FIG. 38 shows an embodiment of event history screens.

Referring now to FIG. 38, in some embodiments, various events may be entered into the Companion and/or the pump and/or the Companion and the pump. These events may include, but are not limited to, information with respect to one or more of the following: insulin/fluid/medication, food, exercise, state of health, and/or a generic/customizable event. With respect to the user interface, the event type may be selected from an event history menu 3800 to view the history/entries related to that event. Examples of some embodiments of event history screens are shown including insulin 3802, food 3804, exercise 3806, state of health 3808 and generic 3810. In some embodiments, the event history screens include a scrolling function, thus, a historical listing including one or more previous events may be seen by scrolling. In various embodiments, the ability to enter events and information pertaining to those events may be desirable for many reasons. For example, a user/caregiver may enter the date/time, duration and type of exercise. This may be helpful to later review with respect to both the amount of fluid infused and analyte/glucose data for the time before, during and after the events. Thus, event logging may be helpful in reviewing therapy and outcomes and for recommending therapy changes. With respect to the various embodiments of this system, in some embodiments where the Companion receives both glucose data and either controls an insulin pump or may control an insulin pump, the information relating to both glucose and insulin delivery may be very desirable to a user and may provide a means for improved health or more convenient therapy to the user.

Figure 39A:
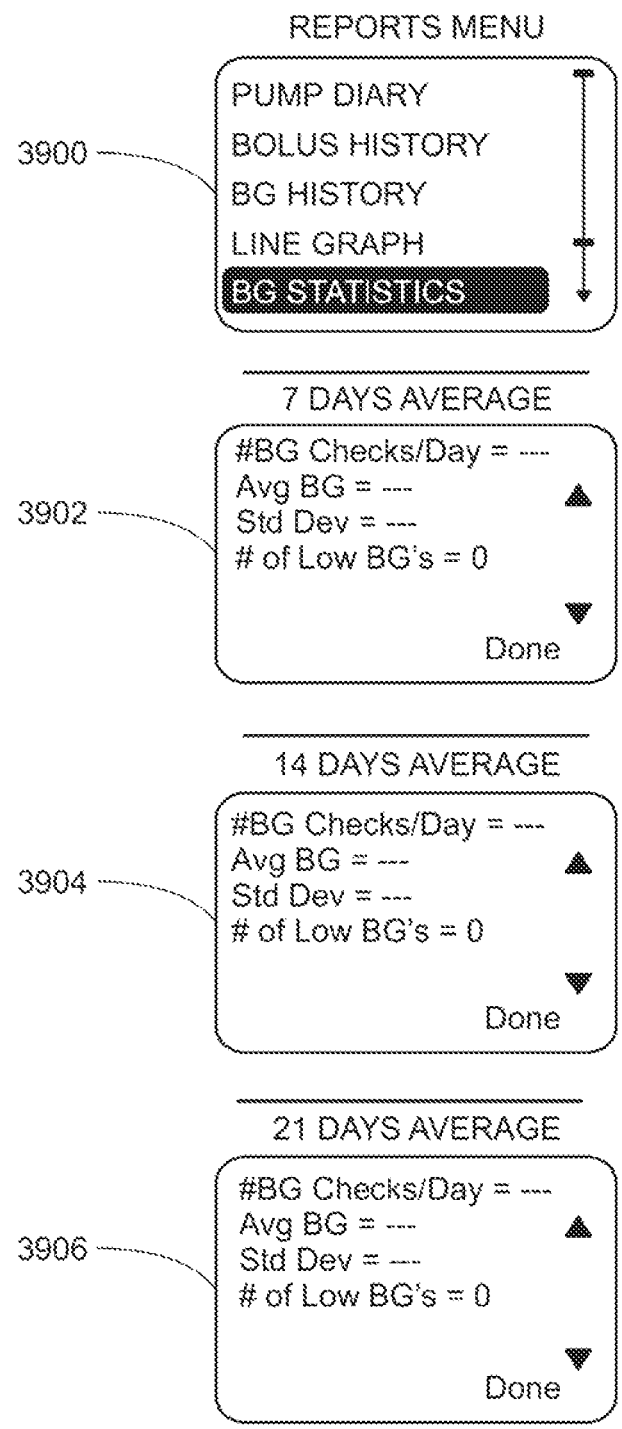
FIGS. 39A-39C show embodiments of report screens.

In addition to those embodiments described above with respect to Reports Menu, referring now to FIG. 39A, the Companion and/or the pump may include additional embodiments in the Reports Menu 3900 including but not limited to BG HISTORY, LINE GRAPH and BG STATISTICS. In some embodiments, and as shown in FIG. 39A, highlighting the report desired serves to select the report. In various embodiments, where BG or glucose may not be the analyte sensed or detected, the Reports may include those for additional or other analytes. However, regardless of the type of analyte, one or more embodiments of Reports shown in FIGS. 39A-39C may be used. In other embodiments, additional reports may be available with respect to the one or more continuous analyte/glucose sensors.

Referring to FIG. 39A, in some embodiments, a BG STATISTIC report may be available. The statistics report may include, but is not limited to, the number of blood glucose checks/day, average blood glucose, standard deviatuion and/or number of low blood glucose readings, number of high blood glucose readings, etc. Additionally, in some embodiments, similar statistics may be available with respect to the one or more continuous glucose sensors, and/or in various embodiments, a sensor which transmits data to the Companion. In some embodiments, and as shown in FIG. 39A, the statistics may be presented to the user/caregiver based on the average over a predetermined number of days, for example, but not limited to, 7 days 3902, 14 days 3904, 21 days 3906. However, in some embodiments, there may be additional or different day values and/or the number of days may be customized/requested by the user/caregiver, i.e., the number of days may be an input or may be preprogrammed as a user customizable feature at setup or other.

Figure 39B:
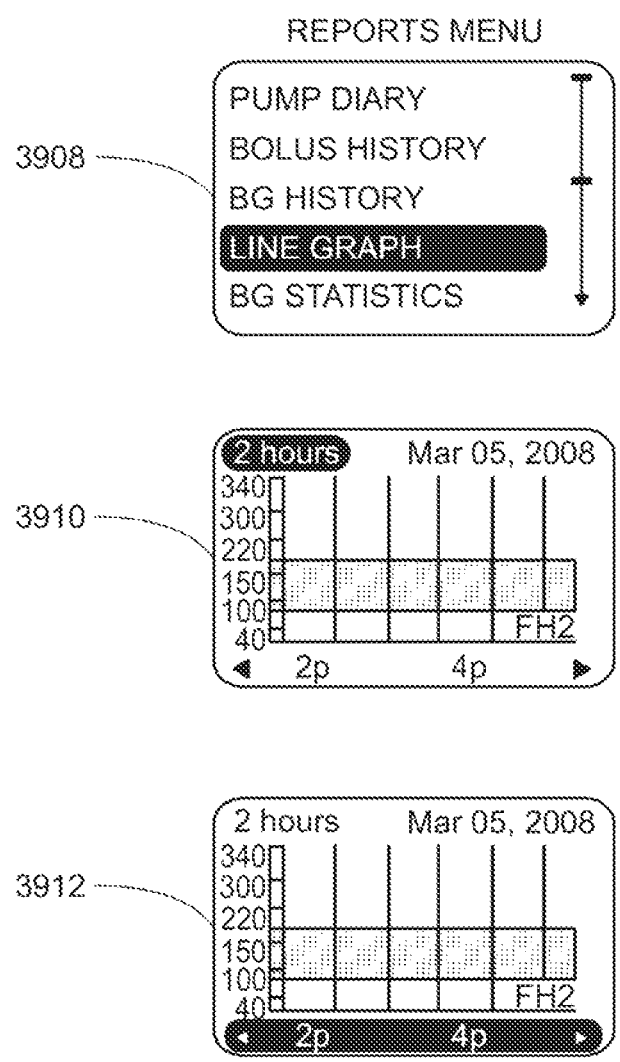

Referring now to FIG. 39B, in some embodiments, a LINE GRAPH report may be selected 3908. In some embodiments, the duration of time, e.g., 2 hours, 4 hours, 6 hours, etc., may be selected and the date may be selected 3910. Additionally, in some embodiments, the time if day, e.g., 3 pm, may be selected 3912 and scrolled through, thus, a single screen may show both a selected/specified duration of time, e.g., 2 hours, during a specific time of day shown in FIG. 39B. In various embodiments, the line graph may vary. However, in various embodiments, the line graph may be useful to the user/caregiver to yield trend data.

Figure 39C:
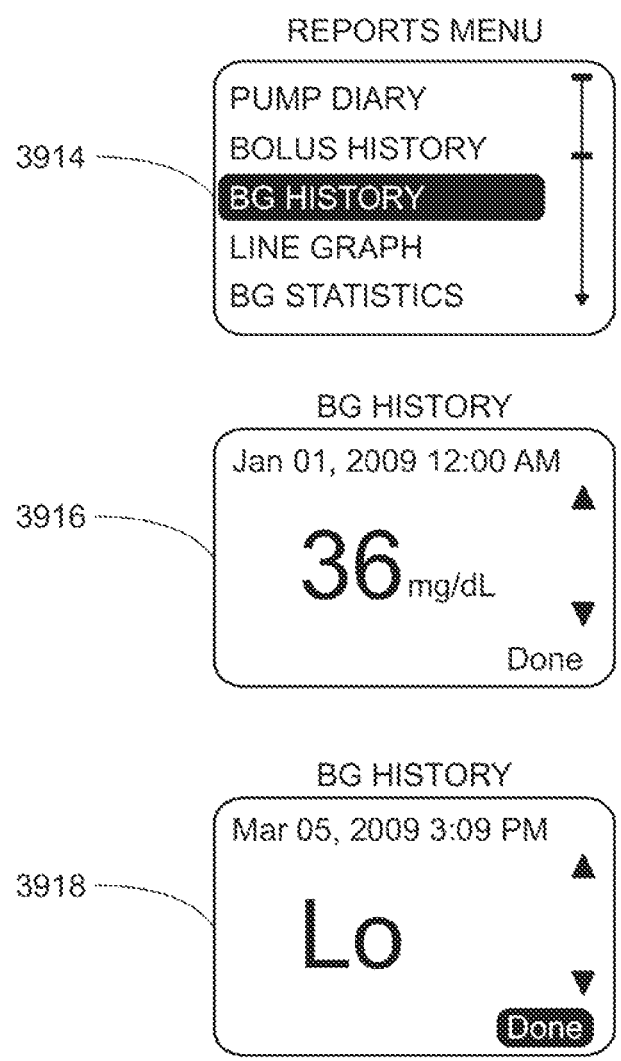

Referring now to FIG. 39C, in some embodiments, a BG HISTORY report may be selected 3914. In some embodiments, a predetermined number of days may be saved on the Companion and/or the pump at any given time. Thus, in some embodiments, an extended history may be uploaded to another device, e.g., a PC. In some embodiments, the BG HISTORY may display one blood glucose/test strip reading per screen and include the date and time 3916. In some embodiments, the BG HISTORY includes a scrolling feature, where the various blood glucose readings may be scrolled through either in chronological order or reverse chronological order.

Still referring to FIG. 39C, in some embodiments, where a blood glucose reading was either lower than a preset target, or higher than a preset target, the BG HISTORY may include an indication of same 3918. In some embodiments, following a blood glucose test, the user may be prompted to enter a comment regarding the reading which may appear on the BG HISTORY. This may include, but is not limited to, one or more of the following: high, low, exercise, stress, illness, menses, different food, etc. In some embodiments, these comments may be customized, thus, the user may enter any comment. In some embodiments, the character length of the comment may be limited, in other embodiments, the character length may not be limited.

Again, the availability of the analyte sensor/analyte value/ strip reader data in the same location as the infused fluid data as well as the event data may improve the safety, ease and quality of therapy a user administers and thus, this system may be an infusion pump system with improved efficiency, efficacy and safety.

Figure 40:
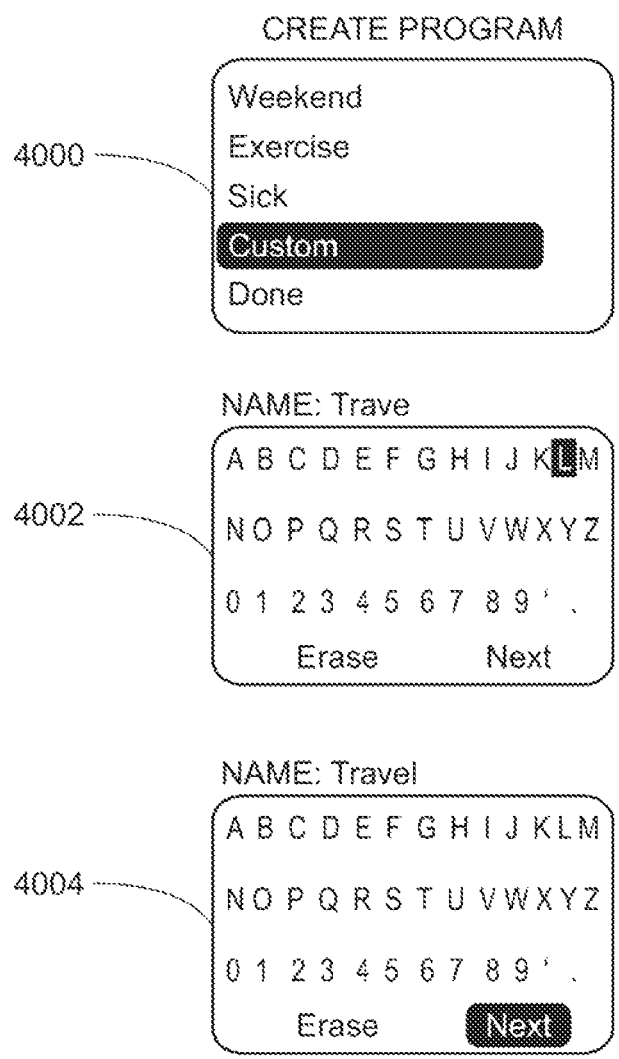
FIG. 40 shows an embodiment of custom entry screens.

Referring now to FIG. 40, as discussed above, in some embodiments, various components of the system may be customizable. An example of one embodiment for customization is shown in FIG. 40. In some embodiments, the system may include a menu item similar to a "CREATE PROGRAM" menu option. This option may be used to enter into the customizable function. In some embodiments, for example, basal programs/basal profiles may include customizable names. In some embodiments, "CUSTOM", or a similar menu option 4000 may indicate that the user/caregiver desires to program a name into the system. In some embodiments, the system may include a textual/numbers input screen 4002 allowing the user to select the number/ letter combination for the customized name 4004.

In various embodiments, one or more menus may invite the user to select "CUSTOM" and/or allow the user to customize the comment and/or name. These include, but are not limited to, bolus comments, exercise comments, illness comments, stress comments, and/or comments associates with a particular analyte value/blood glucose reading/continuous analyte/glucose monitor value or selected time. The ease of entering comments into the system may improve therapy as the user may easily and readily customize the entry and thus, where "exercise", "different food" and/or "stress" may be preprogrammed into the pump as comments for glucose values, the user may elect to enter "skiing", "pizza" and/or "finals", which are more descriptive/indicative of the user's life and thus may be more useful for the user/caregiver when studying trends and recommending/ identifying changes to therapy. The system allows textual input for comments, profile/program names, etc.

Customizable names may improve the quality of care to the user. For example, where the user may preprogram basal rates/programs for a specific exercise, day of the week and/or time of the month, the user may easily associate that which works best for their therapy for a particular event and/or time and quickly and easily select that basal program in the future through naming the program in a way that makes sense to the user. As an example, rather than a basal program named "Weekend" as may be available in the generic menu, the user may preprogram specific basal rates for "Ski Weekend", "Camp Weekend", "Winter Weekend", all which may include a different basal rate/program.

Referring to FIG. 41, in some embodiments, adding an event may be an option on a main menu, which may be easily accessed from the home screen. This may be desirable in some embodiments, for, as discussed above, adding events may improve therapy, thus, the ease at which events may be entered, e.g., the user/caregiver may quickly and conveniently access a point where comments may be entered, may contribute to the frequency the user/caregiver enters events. Thus, ease of access may encourage the user/caregiver to exhibit that behavior which may be best for therapy.

Figure 42:
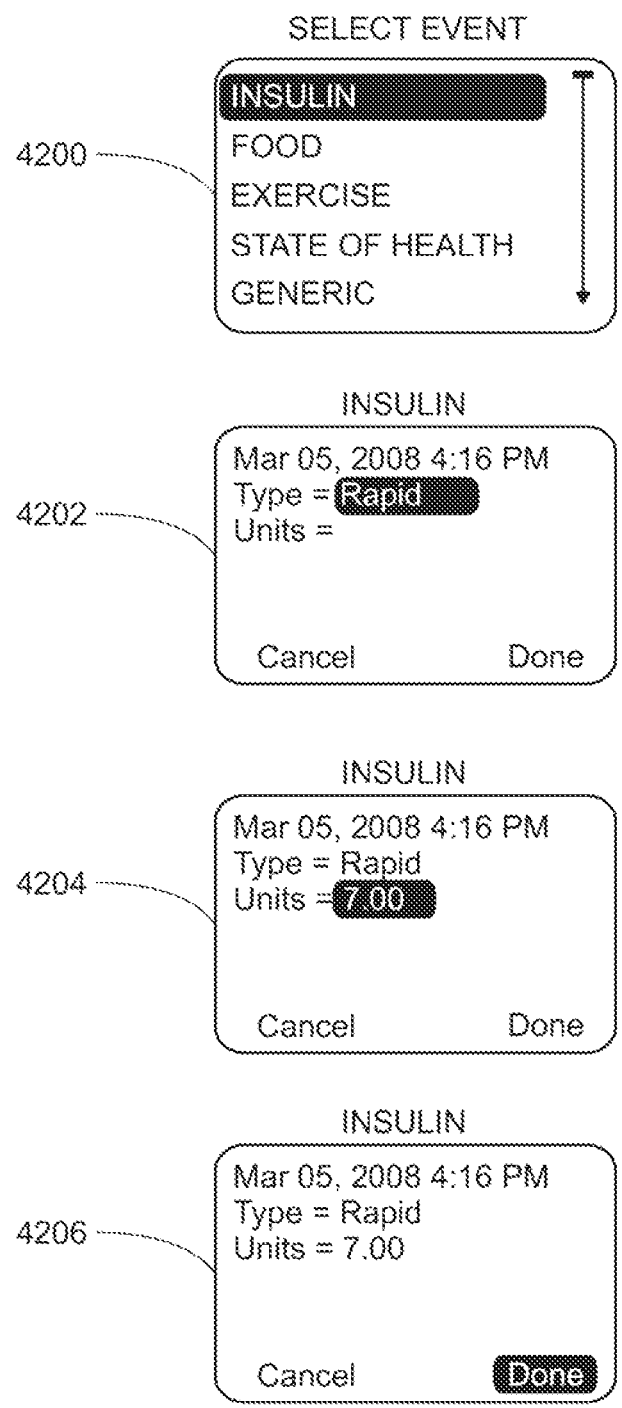
FIG. 42 shows an embodiment of adding medication event screens.

Referring now to FIG. 42, in some embodiments, the system may accommodate the user/caregiver entering a medication event, which, in the exemplary embodiment, as shown in FIG. 42, may be an "insulin event" 4200. However, in some embodiments, the name of the medication may vary depending on the system uses and/or the user preferences. In some embodiments, the event menu 4200 may include additional, and in some embodiments, customizable, categories of medication. In some embodiments, the menu 4200 may include a "medication event" option.

In some embodiments, where a medication event is selected from the event menu 4200, the user/caregiver may be prompted to enter the type and amount (in the case of insulin, the type and "units") 4202, 4204 however, in embodiments where, e.g., the user is entering that a pill was taken, the user may customize the screen to, for example, enter the number of pills taken. In some embodiments, the user may elect "done" to save the entry 4206.

In various embodiments of the system, where the pump is an insulin pump, the insulin delivered is delivered either as a basal or a bolus, and fluid pumped by the pump is tracked and logged automatically, the various history and diary features having been described herein. However, in some cases, the user may inject insulin, e.g., the user may use the pump for bolus deliveries and use injections for basal deliveries or vice versa or the user may use the Companion as a blood glucose meter and/or receiver for a continuous glucose sensor, but may receive insulin therapy through multiple daily injections. In these cases, it may be desirable for the user/caregiver to enter the type and units/volume injected. In some embodiments, the system may include an option for the insulin injected and entered into the system to be documented in a similar fashion from insulin delivered by the pump. For example, in some embodiments, where the user injects bolus insulin and enters the time, amount and type of insulin into the system, where the type is rapid, for example, the system may use the entry in the insulin on board calculation. Further, in some embodiments, where a user is injecting basal insulin, for example, NPH or LANTUS, the system may alert the user to the time for the next delivery, e.g., 12 or 24 hours after an injection of basal insulin.

Figures 43A, 43B, 43C:
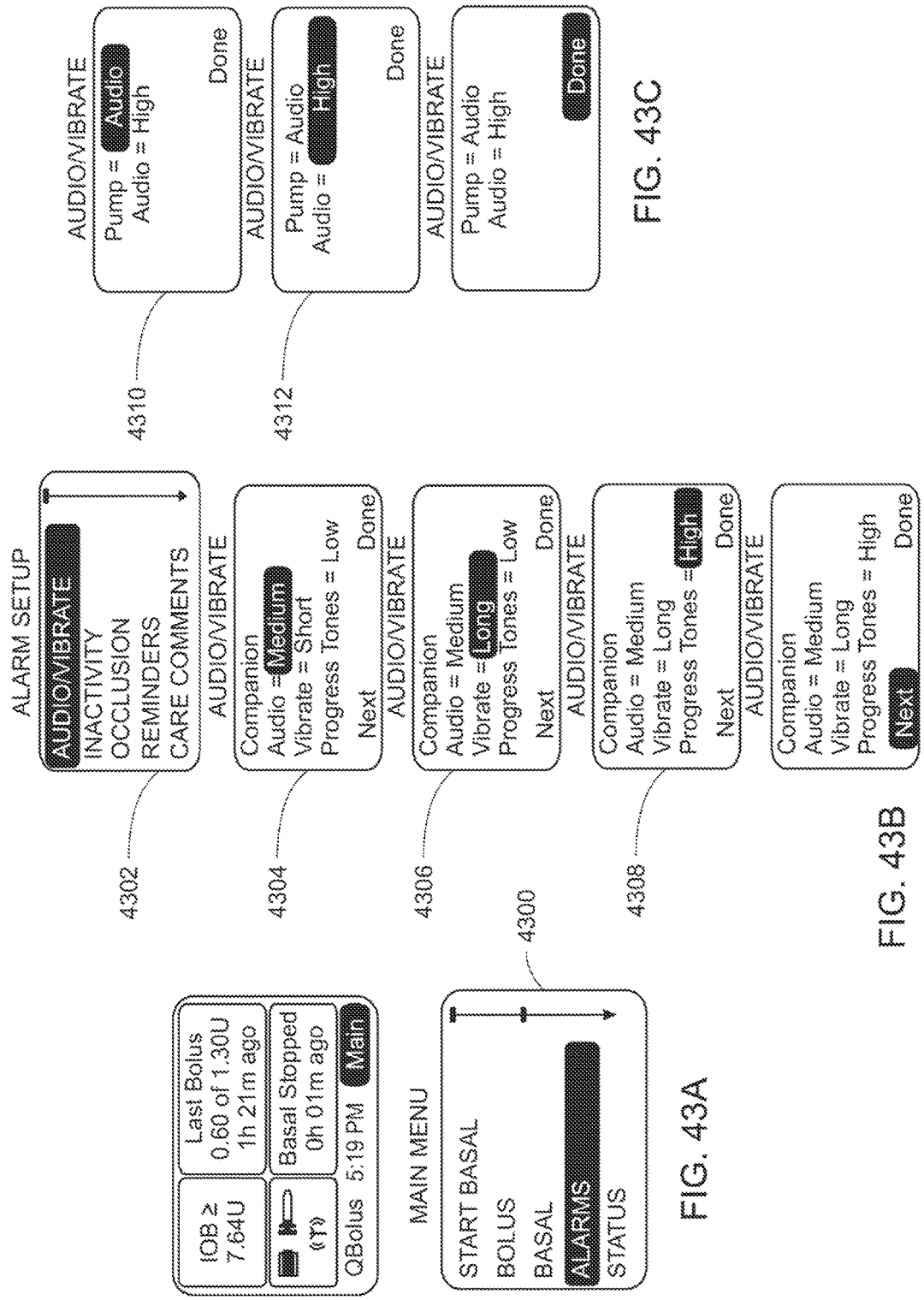
FIGS. 43A-43C show an embodiment of screens for the alarm setup.

Referring now to FIGS. 43A-43C, in some embodiments of the system, a menu for alarm settings may be included 4300. In some embodiments, the alarm settings may be the same or different with respect to the Companion and the pump. In some embodiments, the settings for the Companion alarms may be separate from the settings for the pump alarms. In some embodiments, either the Companion or the pump may include more options and/or different options. This may be desirable for it may be useful, in some embodiments, for the alarm sound and/or vibration itself to be indicative of the nature of the alarm.

Referring now to FIG. 43B, in some embodiments, the Companion alarms may be set separate from the pump alarms. As shown in FIG. 43B, in some embodiments, the alarms may include, but are not limited to, one or more of the various categories shown in the alarm setup screen 4302, which may include, but are not limited to, audio/vibrate, inactivity, occlusion, reminders and/or care comments.

With respect to the audio/vibrate alarm setup, in some embodiments, the Companion and/or pump alarms may include, but are not limited to, audio, vibrate and progress tones 4304. In some embodiments, each of these alarms may include one or more options, which in some embodiments, may include, but are not limited to, low, medium, high, short, long 4306, 4308. Although the embodiments shown in FIG. 43B refer to the Companion, in some embodiments, the same alarm setups may be applicable to the pump and in some embodiments, the same alarm setups may be applicable to another device. In some embodiments, once the alarm setup is complete, the alarm setup may apply to all devices within the system.

Referring now to FIG. 43C, in some embodiments, the pump and/or the Companion alarm/vibrate options may be different. In some embodiments, they may vary from device to device. For example, in some embodiments, the alarm/vibrate menu may include a pump alarm and an option of whether high or low 4310, 4312. However, in other embodiments of these embodiments, the pump alarm/vibrate may include additional options.

Referring now to FIG. 44, in some embodiments, the user/caregiver may select preferences from one or more options with respect to the system. In some embodiments, the preferences may be related to the display and/or the home screen. There may be many options for the display, including, but not limited to, timeout (e.g. in seconds), cursor (e.g., highlight or magnify), home screen, contrast, organization, color, picture, etc. Thus, the system, in some embodiments, allows the user to select various display options based on preference.

With respect to the home screen, options may be desirable as various users may prefer varying information on the home screen. There are many options for home screens, and in some embodiments, may include, but are not limited to, presentation of one or more, but not limited to, of the following: time, date, quick bolus, food bolus, main menu selection, last bolus, last blood glucose value or strip reader value (or most recent strip reader value, which in some embodiments, may also include the time elapsed since the last value), line graph of strip reader values/blood glucose values, basal stopped, bolus stopped, bolus progress, line graph for continuous glucose sensor/continuous analyte sensor, current basal rate, insulin on board, total daily bolus, total daily basal, battery indicator, communication indicator, reservoir volume indicator and/or basal profile. In some embodiments, the user may select both the information for the home screen and/or the color/presentation of the home screen.

Referring again to FIGS. 3 and 36, in some embodiments, at least one of the switch assemblies 304, 308 may be used as a "bolus button". In some embodiments, another input device may be used as a bolus button. The bolus button, in some embodiments, may be similar to those described in U.S. patent application Ser. No. 12/249,882, filed Oct. 10, 2008 and entitled Infusion Pump Assembly (F51) and U.S. patent application Ser. No. 12/347,985, filed Dec. 31, 2008 and entitled Infusion Pump Assembly, now U.S. Publication No. US-2009-0299277, published Dec. 3, 2009 (G75), both of which incorporated herein by reference in their entireties.

In some embodiments, while programming a food bolus or a bolus which includes an insulin to carbohydrate ratio ("I:CHO"), the user interface may prompt the user to confirm the I:CHO. For an example, referring to FIG. 45, to program a food bolus, in some embodiments, the user may select "bolus" from the main menu 4500 and then "food" from the bolus menu 4502. The user may then enter the grams of carbohydrates 4504. In some embodiments, the user may select "details" rather than "next" once the carbohydrates are entered 4508. The user is then prompted to accept or change the current I:CHO. This may be desirable for the user has the option to easily and conveniently both review the current I:CHO and change the I:CHO for the current food bolus. In some embodiments, altering the I:CHO during a food bolus may not reprogram any already preprogrammed I:CHO, rather, the altered I:CHO may only be used for the current food bolus calculation.

This embodiment of the food bolus may lead to more accurate therapy recommendations by the bolus calculator. In some embodiments, the I:CHO is preprogrammed and in some embodiments, multiple I:CHO may be preprogrammed based on time. However, in some circumstances, the user may decide to alter the I:CHO for a given food bolus based on an event. Thus, where the user may desire to alter the I:CHO for a given event, in some embodiments, the user may be required to navigate through a different menu, change the I:CHO for the given time frame, then return to the food bolus. However, changing the I:CHO for an intended one time bolus may have the effect of changing the I:CHO for the given time frame. Thus, where a user does not change the I:CHO back to the previous value, this may lead to an over/under future delivery as the calculation by the bolus calculator will be based on the saved value.

Further, where a user may wish to avoid changing the saved I:CHO value, the user may be reluctant to change the I:CHO for the food bolus. Thus, the user may be inclined to either perform a manual bolus or alter the amount of insulin recommended. Again, this may lead to an over/under delivery.

Figure 45:
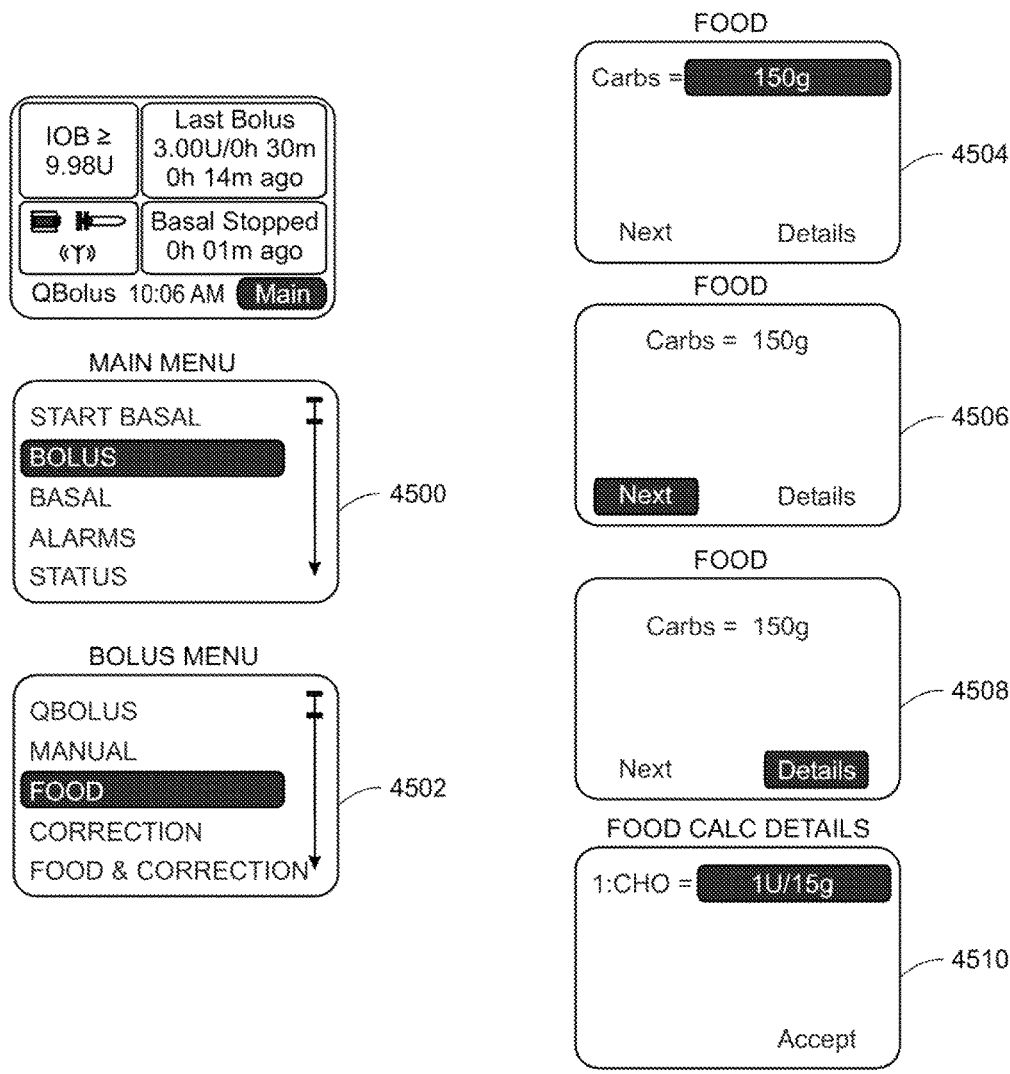
FIG. 45 shows an embodiment of food bolus screens.

However, in the embodiment shown in FIG. 45, the user may alter the I:CHO for a single food bolus, and thus, this may be a more convenient and safe method of altering the I:CHO for accuracy for a single food bolus without altering the preprogrammed I:CHO values. This method may prevent over/under delivery due to accidental changing of a previously saved I:CHO value.

Figure 46:
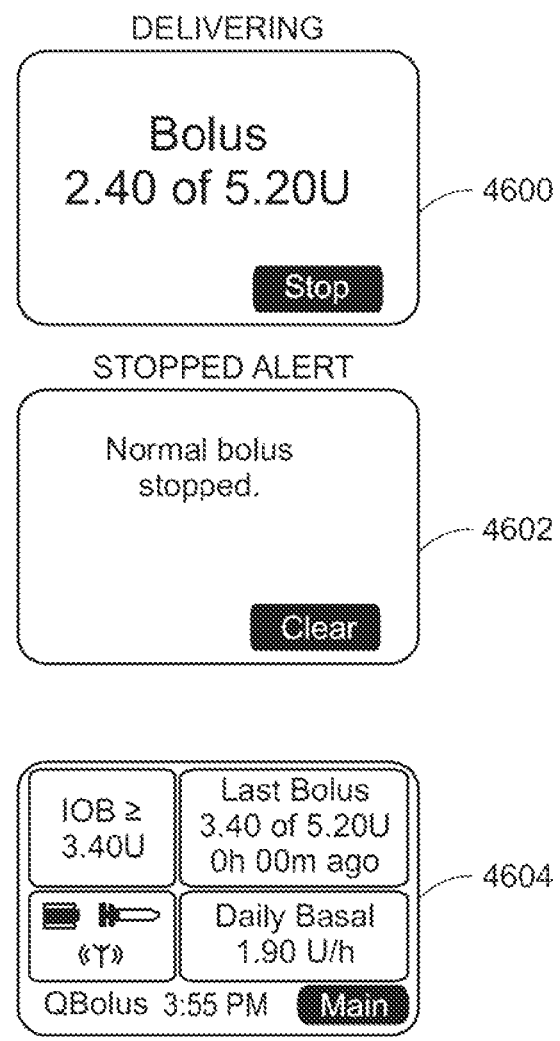
FIG. 46 shows an embodiment of a stop bolus method.

Referring now to FIG. 46, in some embodiments, once a bolus is programmed, a "delivering" screen 4600 appears. In some embodiments, the delivering screen may indicate the progress of the bolus, indicating, in some embodiments, a real-time progress of the volume delivered, and in some embodiments, includes an indication of the total requested bolus. As shown in FIG. 46, in some embodiments, the delivering screen 4600 may indicate the volume of the bolus delivered, e.g., 2.50, as well as the amount requested, e.g., 5.20 U. Thus, the user/caregiver is informed as to the progress of the bolus delivery.

In some embodiments, the delivering screen 4600 also includes a "stop" option. In some embodiments, and as shown in FIG. 46, the "stop" option may be highlighted such that, were a user/caregiver to elect to cancel or "stop" a bolus in progress, in some embodiments, any input device of the pump and/or Companion may "stop" the bolus. This may be desirable in some embodiments for where a programmed bolus volume is unwanted, this embodiment enables the user/caregiver to quickly stop/cancel the bolus using any input device on the pump and/or Companion.

In the case where a bolus in progress is stopped/cancelled, in some embodiments, a "stopped alert" screen 4602 indicates same to the user/caregiver. The screen, in some embodiments, alerts the user/caregiver that the bolus, and in the embodiments shown in FIG. 46, a normal bolus, was stopped. In some embodiments, the user/caregiver may select "clear" to exit the alert screen. As with any alert, in some embodiments, the alert screen may be accompanied by an audio and/vibratory indication. In some embodiments, the user/caregiver may select, as part of the user preferences, the audio and/or vibratory indication to accompany alert screens.

In some embodiments, and as shown in FIG. 46, where the alert is cleared, the display may return to the home screen 4604. As shown in the embodiments of FIG. 46, the home screen may indicate the last bolus. In this case, as shown in FIG. 46, where a bolus was stopped/cancelled, the home screen may indicate the amount delivered as well as the original amount requested. As shown in FIG. 46, the home screen 4604 indicates "Last Bolus 3.40 of 5.20 U 0 h 00 m ago". Thus, in some embodiments, this indication clearly informs the user/caregiver that a bolus was stopped as well as clearly indicates the total amount delivered in the last bolus. As well, in some embodiments, and as shown in FIG. 46, the insulin on board is indicated as greater than or equal to 3.40 U. This embodiment may be desirable for the user/caregiver is presented with an alert where a bolus is stopped, prompting the user to "clear", as well, fully indicates the status of the last bolus on the home screen. Therefore, if, in some situations, a user/caregiver accidentally stops a bolus in progress, they will be alerted of the fact that the bolus was stopped and the total amount delivered may be indicated on the home screen. This may be a safe method for fully informing the user/caregiver of the fact that a bolus was stopped, as well, of the total amount delivered before the bolus was stopped.

Referring now to FIG. 47, in some embodiments, an extended bolus may be programmed. Once programmed, in some embodiments, the home screen 4700 may indicate the progress of the extended bolus, for example, "Ext. Bolus 0.10 of 2.000 0 h 02 m". In some embodiments, an extended bolus may be in progress for a period of time, e.g. 2 hours, and thus, a readily visible indicator of the progress may be desirable. Additionally, an indication of the total amount to be delivered may be desirable for the user/caregiver when making therapy decisions during the time of the extended bolus.

Still referring to FIG. 47, in some embodiments, where a user/caregiver desires to stop or cancel the extended bolus in progress, the user/caregiver may navigate to the main menu 4702, and in some embodiments, as shown in FIG. 47 on the home screen 4700, navigation to the main menu may be accomplished through an input device, the "main" being highlighted thus easily selectable.

Once at the main menu 4702, in some embodiments, the first highlighted option in the menu menu 4702 is "Stop". Selecting "Stop" navigates to a "Confirm" screen 4704. In some embodiments, the bottom of the confirm screen 4704 may include a "yes" and "no" option. In some embodiments, such as the one shown in FIG. 47, the "yes" is highlighted.

If "yes" is selected in the confirm screen, the extended bolus is stopped. In some embodiments, the home screen 4700 may be updated to indicate the last bolus being an extended bolus where, e.g., 0.10 of 2.00 was delivered. In some embodiments, this is similar to the method above with respect to a cancelled bolus. If the user chooses to navigate to "no" and select "no", in some embodiments, the home screen 4700 will appear and the extended bolus will continue as programmed.

Thus, in some embodiments, where the user/caregiver desires to stop and extended bolus, through one of the input devices, two selection, e.g., two depressions of a switch, will navigate to the confirm screen. This maybe desirable giving ease to the user/caregiver for cancelling an extended bolus. Additionally, the confirm screen ensure that the user/caregiver is aware that they are in the "stop" menu and that by selecting "yes" the extended bolus will stop. Further, in some embodiments, the user/caregiver must select "yes" in the confirm menu to stop and extended bolus. In these embodiments, this may be desirable for it may reduce accidental stopping or cancelling of extended bolus delivery.

Figures 48A, 48B:
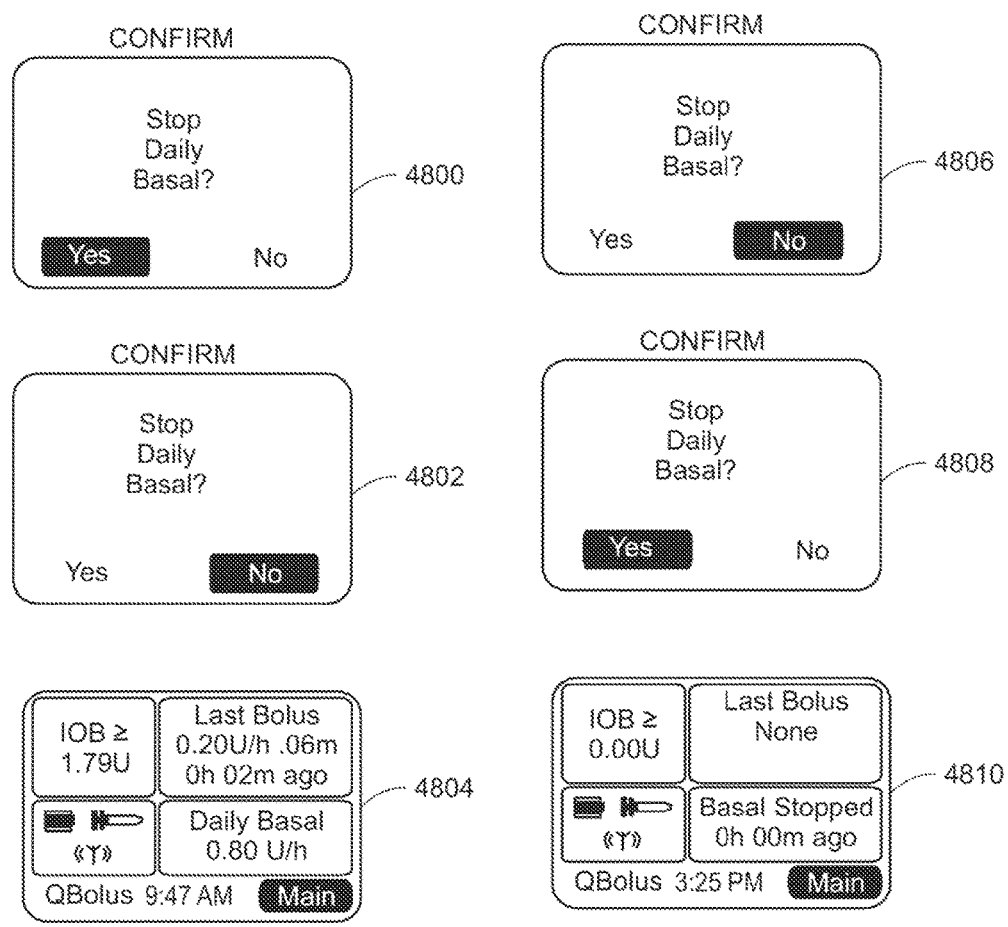
FIGS. 48A-48B show embodiments of stop basal methods.

Referring now to FIGS. 48A and 48B, various embodiments of the method for stopping basal are shown. In some embodiments, navigation to stop basal may be through the main menu, stop option (see FIG. 47, 4702). As shown in FIG. 48A, in some embodiments, the confirm screen 4800 may include a highlight to the "yes" option, prompting the user/caregiver to navigate to the "no" option. As shown in FIG. 48A, where the "no" option is selected, in some embodiments, the home screen 4804 is shown.

Referring now to FIG. 48B, in some embodiments, navigation to stop basal may be through the main menu, stop option (see FIG. 47, 4702). As shown in FIG. 48B, in some embodiments, the confirm screen 4806 may include a highlight to the "no" option, prompting the user/caregiver to navigate to the "yes" option. As shown in FIG. 48B, where the "yes" option is selected 4808, in some embodiments, the home screen 4810 is shown. As shown in the home screen 4810, where the basal is stopped, the home screen 4810, in some embodiments, includes a "basal stopped 0 h 00 m ago" message.

Thus, in some embodiments, this indication on the home screen 4810 clearly informs the user/caregiver that a basal was stopped as well as clearly indicates the total time elapsed since basal delivery was stopped. This embodiment may be desirable for the user/caregiver is presented with a confirm screen when "stop daily basal" is selected, prompting the user to navigate to select "yes" 4808. Therefore, in these embodiments, it may be difficult to accidentally stop basal delivery for the user/caregiver must navigate to the "yes" option to confirm they wish basal delivery to stop. Additionally, where basal delivery was intentionally stopped, in some embodiments, the home screen 4810 may indicate this information as well, indicate the amount of elapsed time since basal delivery stopped. This may be a safe method for fully informing the user/caregiver of the fact that basal delivery was stopped, as well, of the total amount of time since basal delivery stopped. Thus, the user/caregiver may be better able to determine future therapy based on this easily and fully accessible status information.

Further, in some embodiments, as those shown in FIG. 48B, the user/caregiver must select "yes" in the confirm menu 4806 to stop basal delivery. In these embodiments, this may be desirable for it may reduce accidental stopping or cancelling of basal delivery. Also, in the embodiments where the system is used to deliver insulin to users with diabetes, stopping the basal delivery may be harmful to the user. Thus, it may be desirable to ensure the user is fully informed of this occurrence and that stopping basal is not easily accomplished accidentally. In some embodiments, where stopping the basal delivery has been selected, if there is an extended bolus in progress, the system may require the user/caregiver to stop the extended bolus before the system will allow the user to stop the daily basal. This may be desirable in some embodiments, where a user/caregiver desires to stop daily basal, i.e., stop all regular delivery of fluid, it may be the case that the user/caregiver does not realize an extended bolus is in progress. Thus, in some embodiments, as a safety step, the system may require the user to stop any extended bolus prior to allowing the user to stop daily basal delivery. This may prevent over delivery or unintended delivery of fluid and, in some embodiments, where the pump is an insulin pump, may prevent unintended over delivery of insulin.

Figures 49A, 49B:
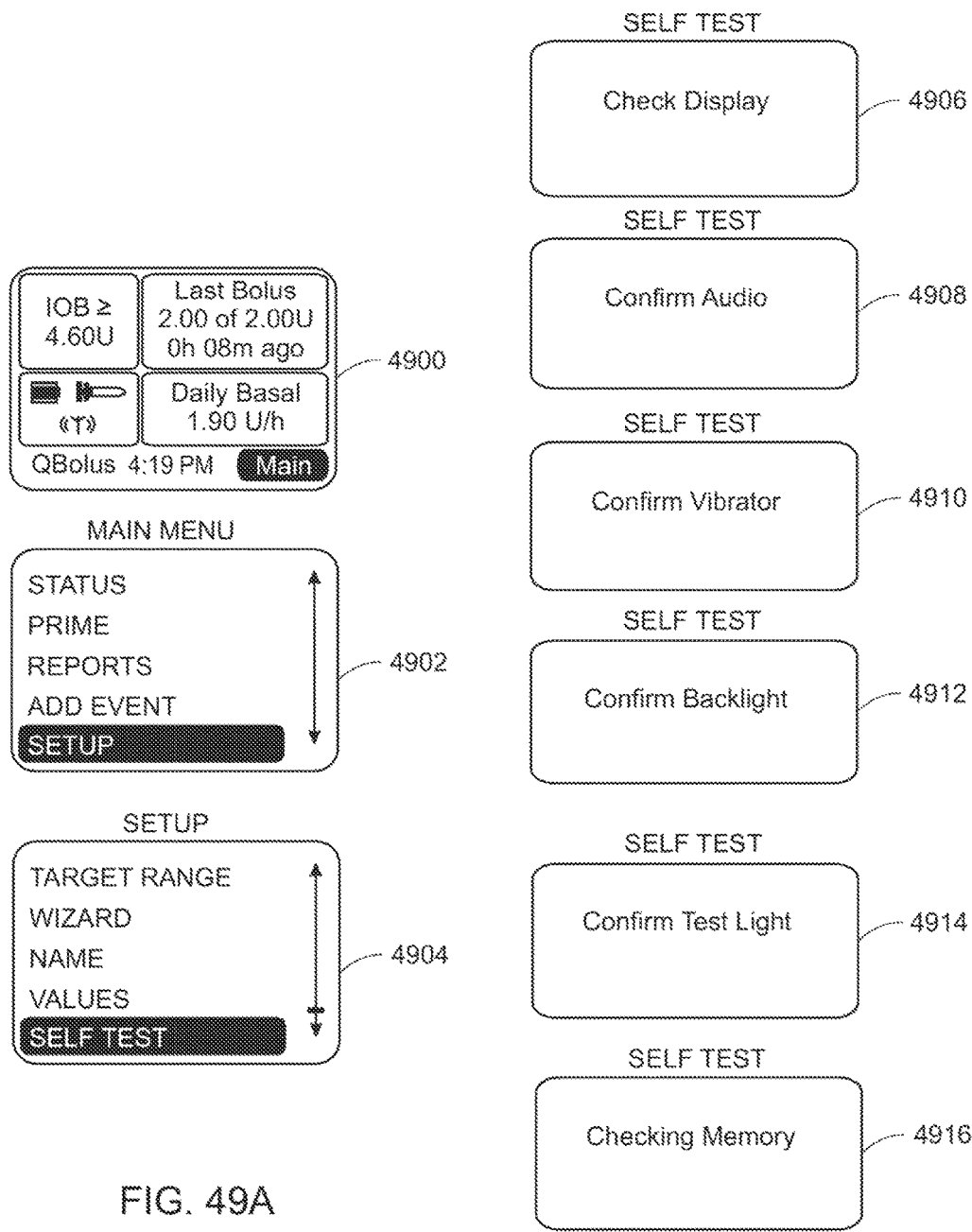
FIGS. 49A-49B show an embodiment of a companion self test.

Referring now to FIGS. 49A and 49B, embodiments of a Companion self test are shown. In some embodiments, a Companion self test may be run upon user/caregiver command. However, in some embodiments, the Companion self test may run on a preprogrammed schedule, for example, but not limited to, one or more of the following: upon pairing with a new pump, on the initial use, after battery re-charge or upon replacement of a battery and/or on a pre-programmed time schedule, e.g., every 10 days or every day or every month. The self test may be performed to ensure that the Companion is functioning properly. For example, to verify that one or more components are functioning as expected, where the components may include, but are not limited to, one or more of the following: display, audio, vibrator, backlight, test light and memory functions. Thus, the self test may be desirable in some embodiments to ensure safety of the user as the self test may diagnose or anticipate a Companion failure.

Referring now to FIG. 49A, in some embodiments, the user may command the Companion to undergo a self test through navigating from the home screen 4900 to the main menu 4902. In some embodiments, the main menu may include a "self test" option. The user may navigate to the self test option and select 4904. Referring now to FIG. 49B, one embodiments of a self test is shown. In some embodiments, as the Companion undergoes the self test, the Companion display may indicate the step of the self test the in progress, e.g., "check display" 4906, "confirm audio" 4908, "confirm vibrator" 4910, "confirm backlight" 4912, "confirm rest light" 4914, "checking memory" 4916. In various embodiments, the steps of the self test may vary and may include less or additional steps. In some embodiments, the user may elect to command a self test on suspicion that a component of the Companion may not be functioning as expected. Thus, the self test provides an easy and efficient method for diagnosing potential or occurring failures and to notify the user/caregiver in an efficient manner.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. An infusion pump system comprising:
   at least one infusion pump;
   a companion device, the companion device in wireless communication with the at least one infusion pump; and
   a user interface on the companion device, the user interface comprising a touch screen display, the touch screen display adapted to display a plurality of user-selectable, single-character inputs, wherein the touch screen display is configured to receive a plurality of user selections of the user-selectable, single-character inputs,
   wherein the user interface further comprising a home screen comprising visual indication of a gauge to the action of the insulin currently in the user and last bolus delivered, the last bolus delivered comprising the time elapsed since delivery completed and the amount delivered.

2. The system of claim 1 wherein the received plurality of user selections of the user-selectable, single-character inputs comprises a customized name for at least one basal profile.

3. The system of claim 1 wherein the received plurality of user selections of the user-selectable, single-character inputs comprises at least one customized comment.

4. The system of claim 1 wherein the received plurality of user selections of the user-selectable, single-character inputs comprises at least one customized event.

5. The system of claim 1 wherein the user interface further comprises a pairing mode for pairing the companion device with the at least one infusion pump, the pairing mode enables wireless communication between the at least one infusion pump and the companion device, wherein the user interface requires both the at least one infusion pump and the companion device to be in the pairing mode simultaneously.

6. The system of claim 1 wherein the at least one infusion pump comprising a display.

7. The system of claim 1 wherein the user interface includes at least one alarm setting for the at least one infusion pump and the companion device, the at least one alarm setting may be selected using the user interface and wherein the at least one alarm setting for the at least one infusion pump and the companion device may be different.

8. The system of claim 1 further comprising a second user interface residing on the at least one infusion pump.

9. The system of claim 1, wherein the plurality of user-selectable, single-character inputs includes at least one single-letter input.

10. The system of claim 1, wherein the plurality of user-selectable, single-character inputs includes at least one single-numeric input.

11. The system of claim 1, wherein the plurality of user-selectable, single-character inputs includes at least one single-punctuation-mark input.

12. The system according to claim 1, wherein the plurality of user-selectable, single-character inputs defines at least one of a bolus comment, an exercise comment, an illness comment, and a stress comment.

13. The system according to claim 1, wherein the plurality of user-selectable, single-character inputs defines an analyte value.

14. The system according to claim 1, wherein the plurality of user-selectable, single-character inputs defines a blood glucose reading.

15. The system according to claim 1, wherein the plurality of user-selectable, single-character inputs defines a glucose monitor value.

16. The system according to claim 1, wherein the plurality of user-selectable, single-character inputs defines a customized name.

17. The system according to claim 1, wherein the plurality of user-selectable, single-character inputs corresponds to preprogrammed basal rates that correspond to a specific exercise.

18. The system according to claim 1, wherein the user interface comprising visual indication of a bolus delivery in progress comprising an amount delivered and a total amount requested.

19. The system of claim 18, further comprising wherein when the bolus delivery is stopped, the user interface further comprising a visual indication of delivery stopped comprising indication of the amount delivered and the total amount requested.

* * * * *